(12) United States Patent
Amberg et al.

(10) Patent No.: US 6,670,367 B1
(45) Date of Patent: *Dec. 30, 2003

(54) AZINYLOXY, AND PHENOXY-DIARYL-CARBOXYLIC ACID DERIVATIVES, THEIR PREPARATION AND USE AS MIXED ETA/ETB ENDOTHELIN RECEPTOR ANTAGONISTS

(75) Inventors: Wilhelm Amberg, Schwetzingen (DE); Rolf Jansen, Mannheim (DE); Andreas Kling, Mannheim (DE); Dagmar Klinge, Heidelberg (DE); Hartmut Riechers, Neustadt (DE); Stefan Hergenröder, Mainz (DE); Manfred Raschack, Weisenheim (DE); Liliane Unger, Ludwigshafen (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,137

(22) PCT Filed: Mar. 2, 1997

(86) PCT No.: PCT/EP97/04688
§ 371 (c)(1),
(2), (4) Date: Mar. 1, 1999

(87) PCT Pub. No.: WO98/09953
PCT Pub. Date: Mar. 12, 1998

(30) Foreign Application Priority Data

Sep. 5, 1996 (DE) .......................................... 196 36 046

(51) Int. Cl.[7] ..................... C07D 239/34; C07D 239/46; A61K 31/505; A61P 9/04; A61P 9/12
(52) U.S. Cl. ..................... 514/269; 544/298; 544/299; 544/309; 544/310
(58) Field of Search ................................. 544/298, 299, 544/309, 310; 514/269

(56) References Cited

U.S. PATENT DOCUMENTS

| | | | | |
|---|---|---|---|---|
| 5,661,106 A | * | 8/1997 | Baumann et al. | 544/216 |
| 5,703,017 A | * | 12/1997 | Baumann et al. | 544/219 |
| 5,932,730 A | * | 8/1999 | Riechers et al. | 544/298 |
| 5,969,134 A | * | 10/1999 | Riechers et al. | 544/298 |

FOREIGN PATENT DOCUMENTS

| | | |
|---|---|---|
| AU | 38045/95 | 5/1996 |
| DE | 43 35 950 | 4/1995 |
| DE | 195 33 023 | * 4/1996 |
| WO | 94 25442 | * 11/1994 |
| WO | 95/26716 | 10/1995 |
| WO | 96/11914 | 4/1996 |
| WO | 97/12878 | 4/1997 |

OTHER PUBLICATIONS

J. Med. Chem. 1996, 39, 2123–2128, Riechers et a. Inhibitors of Endothelin, Webb et al.,002–052.

\* cited by examiner

Primary Examiner—Richard L. Raymond
Assistant Examiner—Venkataraman Balasubramanian
(74) Attorney, Agent, or Firm—Wood, Phillips, Katz, Clark & Mortimer

(57) ABSTRACT

The invention relates to carboxylic acid derivatives of the formula I

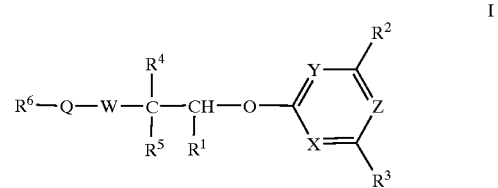

where the radicals have the meanings stated in the description, and to their use as drugs.

5 Claims, No Drawings

AZINYLOXY, AND PHENOXY-DIARYL-CARBOXYLIC ACID DERIVATIVES, THEIR PREPARATION AND USE AS MIXED ETA/ETB ENDOTHELIN RECEPTOR ANTAGONISTS

The present invention relates to novel carboxylic acid derivatives, their preparation and use.

Endothelin is a peptide which consists of 21 amino acids and is synthesized and released by vascular endothelium. Endothelin exists in three isoforms, ET-1, ET-2 and ET-3. "Endothelin" or "ET" hereinafter means one or all isoforms of endothelin. Endothelin is a potent vasoconstrictor and has a great effect on vessel tone. It is known that this vasoconstriction is caused by binding of endothelin to its receptor (Nature, 332, 1988, 411–415; FEBS Letters, 231, 1988, 440–444 and Biochem. Biophys. Res. Commun., 154, 1988, 868–875).

Increased or abnormal release of endothelin causes persistent vasoconstriction in peripheral, renal and cerebral vessels, which may lead to disorders. As reported in the literature, endothelin is involved in a number of disorders. These include: hypertension, acute myocardial infarct, pulmonary hypertension, Raynaud's syndrome, cerebral vasospasms, stroke, benign prostate hypertrophy, atherosclerosis and asthma (J. Vascular Med. Biology 2, (1990) 207, J. Am. Med. Association 264, (1990) 2868, Nature 344, (1990) 114, N. Engl. J. Med. 322, (1989) 205, N. Engl. J. Med. 328, (1993) 1732, Nephron 66, (1994) 373, Stroke 25, (1994) 904, Nature 365, (1993) 759, J. Mol. Cell. Cardiol. 27, (1995) A234; Cancer Research 56, (1996) 663).

At least two endothelin receptor subtypes, $ET_A$ and $ET_B$ receptors, have been described in the literature (Nature 348, (1990) 730, Nature 348, (1990) 732). Accordingly, substances which inhibit the binding of endothelin to the two receptors ought to antagonize the physiological effects of endothelin and therefore be valuable drugs.

WO 96/11914 describes carboxylic acid derivatives which, however, bind with high affinity to the $ET_A$ receptor and with considerably less affinity to the $ET_B$ receptor (called $ET_A$-specific antagonists).

$ET_A$-specific antagonists mean here those antagonists whose affinity for the $ET_A$ receptor is at least twenty times higher than their affinity for the $ET_B$ receptor.

It is an object of the present invention to provide endothelin receptor antagonists which bind with approximately the same affinity to the $ET_A$ and $ET_B$ receptors (called mixed antagonists).

Approximately the same affinity for the receptors means that the $ET_A$:$ET_B$ affinity ratio is greater than 0.1 and less than 20, preferably less than 10.

We have found that this object is achieved by carboxylic acid derivatives of the formula I

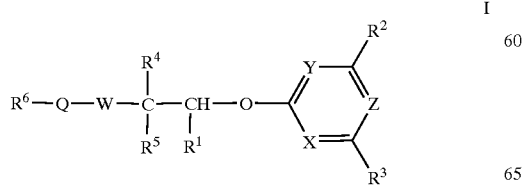

where $R^1$ is tetrazole [sic] or a group

where R has the following meaning:
a) a radical $OR^7$ where $R^7$ is:
hydrogen, the cation of an alkali metal, the cation of an alkaline earth metal, a physiologically tolerated organic ammonium ion such as $C_1$–$C_4$-alkylammonium or the ammonium ion;
$C_3$–$C_8$-cycloalkyl, $C_1$–$C_8$-alkyl, $CH_2$-phenyl which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, carboxyl, $NH(C_1$–$C_4$-alkyl), $N(C_1$–$C_4$-alkyl)$_2$;
$C_3$–$C_6$-alkenyl or $C_3$–$C_6$-alkynyl, it being possible for these groups in turn to carry one to five halogen atoms;
$R^7$ can furthermore be a phenyl radical which may carry one to five halogen atoms and/or one to three of the following radicals, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)$_2$;
b) a 5-membered heteroaromatic system which is linked via a nitrogen atom, such as pyrrolyl, pyrazolyl, imidazolyl and triazolyl, which may carry one to two halogen atoms or one to two $C_1$–$C_4$-alkyl or one to two $C_1$–$C_4$-alkoxy groups;
c) a group

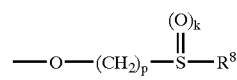

where k is 0, 1 and 2, p is 1, 2, 3 and 4 and $R^8$ is $C_1$–$C_4$-alkyl, $C_3$–$C_8$-cycloalkyl, $C_3$–$C_6$-alkenyl, $C_3$–$C_6$-alkynyl or phenyl which can be substituted by one or more, eg. one to three, of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, carboxyl, $NH(C_1$–$C_4$-alkyl), $N(C_1$–$C_4$-alkyl)$_2$;
d) a radical

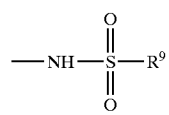

in which $R^9$ is:
$C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, it being possible for these radicals to carry a $C_1$–$C_4$-alkoxy, $C_1$–$C_4$-alkylthio and/or a phenyl radical as mentioned under c);
phenyl, unsubstituted or substituted, in particular as mentioned above, e) $R^1$ can furthermore be

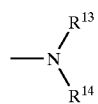

where $R^{13}$ and $R^{14}$ can be identical or different and have the following meanings:

hydrogen, $C_1$–$C_8$-alkyl, $C_3$–$C_8$-cycloalkyl, $C_3$–$C_8$-alkenyl, $C_3$–$C_8$-alkynyl, benzyl, phenyl which may carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, NH($C_1$–$C_4$-alkyl), N($C_1$–$C_4$-alkyl)$_2$, or $R^{13}$ and $R^{14}$ together form a $C_4$–$C_7$-alkylene chain which is closed to form a ring and which may be substituted by $C_1$–$C_4$-alkyl and in which an alkylene group may be replaced by oxygen, sulfur or nitrogen, such as —(CH$_2$)$_4$—, —(CH$_2$)$_5$—, —(CH$_2$)$_6$—, —(CH$_2$)$_2$—O—(CH$_2$)$_2$—, —(CH$_2$)$_7$—, —CH$_2$—S—(CH$_2$)$_2$—, —CH$_2$—NH—(CH$_2$)$_2$—, —(CH$_2$)$_2$—N—(CH$_2$)$_2$—;

$R^2$ hydrogen, hydroxyl, NH$_2$, NH($C_1$–$C_4$-alkyl), N($C_1$–$C_4$-alkyl)$_2$, halogen, $C_1$–$C_4$-alkyl, $C_2$–$C_4$-alkenyl, $C_2$–$C_4$-alkynyl, $C_1$–$C_4$-hydroxyalkyl, $C_1$–$C_4$-haloalkyl, $C_1$–$C_4$-alkoxy, $C_1$–$C_4$-haloalkoxy or $C_1$–$C_4$-alkylthio, or $CR^2$ is linked to $CR^{10}$ as indicated below to give a 5- or 6-membered ring.

X nitrogen or methine.

Y nitrogen or methine.

Z nitrogen or $CR^{10}$, where $R^{10}$ is hydrogen or $C_1$–$C_4$-alkyl, or $CR^{10}$ forms together with $CR^2$ or $CR^3$ a 5- or 6-membered alkylene or alkenylene ring which may be substituted by one or two $C_1$–$C_4$-alkyl groups and in which in each case one or more methylene groups can be replaced by oxygen, sulfur, —NH or N($C_1$–$C_4$-alkyl)$_2$.

At least one of the ring members X, Y or Z is nitrogen.

$R^3$ hydrogen, hydroxyl, NH$_2$, NH($C_1$–$C_4$-alkyl), N($C_1$–$C_4$-alkyl)$_2$, halogen, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, $C_1$–$C_4$-haloalkoxy, $C_1$–$C_4$-hydroxyalkyl or $C_1$–$C_4$-alkylthio, or $CR^3$ is linked to $CR^{10}$ as indicated above to give a 5- or 6-membered ring.

$R^4$ and $R^5$ (which may be identical or different):

phenyl or naphthyl, which may be substituted by one or more of the following radicals: halogen, nitro, cyano, hydroxyl, mercapto, $C_1$–$C_4$-alkyl, $C_2$–$C_4$-alkenyl, $C_1$–$C_4$-hydroxyalkyl, $C_2$–$C_4$-alkynyl, $C_1$–$C_4$-haloalkyl, $C_1$–$C_4$-alkoxy, phenoxy, carboxyl, $C_1$–$C_4$-haloalkoxy, $C_1$–$C_4$-alkylthio, amino, NH($C_1$–$C_4$-alkyl), N($C_1$–$C_4$-alkyl)$_2$ or phenyl which can be substituted one or more times, eg. one to three times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or phenyl or naphthyl, which are linked together in the ortho positions by a direct linkage, a methylene, ethylene or ethenylene group, an oxygen or sulfur atom or an SO$_2$, NH or N-alkyl group;

$C_3$–$C_8$-cycloalkyl.

$R^6$ $C_3$–$C_8$-Cycloalkyl, it being possible for these radicals in each case to be substituted one or more times by: halogen, hydroxyl, mercapto, carboxyl, nitro, cyano, $C_1$–$C_4$-alkoxy, $C_1$–$C_4$-alkyl, $C_2$–$C_4$-alkenyl, $C_2$–$C_4$-alkynyl, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-alkyl-carbonylalkyl, NH($C_1$–$C_4$-alkyl), N($C_1$–$C_4$-alkyl)$_2$, or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl or naphthyl, each of which can be substituted by one or more of the following radicals: halogen, $R^{15}$, nitro, mercapto, carboxyl, cyano, hydroxyl, amino, $C_1$–$C_4$-alkyl, $C_2$–$C_4$-alkenyl, $C_2$–$C_4$-alkynyl, $C_3$–$C_6$-alkenyloxy, $C_1$–$C_4$-haloalkyl, $C_3$–$C_6$-alkynyloxy, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

a five- or six-membered heteroaromatic system containing one to three nitrogen atoms and/or one sulfur or oxygen atom, which may carry one to four halogen atoms and/or one to two of the following radicals: $C_1$–$C_4$-alkyl, $C_2$–$C_4$-alkenyl, $C_1$–$C_4$-haloalkyl, $C_1$–$C_4$-alkoxy, $C_1$–$C_4$-haloalkoxy, $C_1$–$C_4$-alkylthio, phenyl or phenoxy it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$R^{15}$ is $C_1$–$C_4$-alkyl, $C_1$–$C_4$-alkylthio or $C_1$–$C_4$-alkoxy which carry one of the following radicals: hydroxyl, carboxyl, amino, NH($C_1$–$C_4$-alkyl), N($C_1$–$C_4$-alkyl)$_2$, carboxamide [sic] or CON($C_1$–$C_4$-alkyl)$_2$;

W sulfur or oxygen.

Q a spacer whose length corresponds to that of a $C_2$–$C_4$ chain. The function of Q is to produce a defined distance between the groups $R^6$ and W in the compounds of the formula I. The distance should correspond to the length of a $C_2$–$C_4$-alkyl chain. This can be achieved by a large number of chemical radicals, for example with $C_2$–$C_4$-alkyl, $C_3$–$C_4$-alkenyl, $C_3$–$C_4$-alkynyl, —S—CH$_2$—CH$_2$—, —O—CH$_2$—CH$_2$—, —N—CO—CH$_2$—O—, it being possible for each of these radicals to be substituted one or more times by: halogen, hydroxyl, mercapto, $C_1$–$C_4$-alkyl, $C_2$–$C_4$-alkenyl, $C_2$–$C_4$-alkynyl, carboxyl, nitro, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-alkylcarbonylalkyl, NH($C_1$–$C_4$-alkyl), N($C_1$–$C_4$-alkyl)$_2$, phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio.

Or the spacer Q is part of a 5–7-membered heterocyclic or carbocyclic ring to which $R^6$ is fused.

The following definitions apply thereto and hereinafter:

An alkali metal is, for example, lithium, sodium, potassium;

An alkaline earth metal is, for example, calcium, magnesium, barium;

$C_3$–$C_8$-cycloalkyl is, for example, cyclopropyl, cyclobutyl, cyclopentyl, cyclohexyl, cycloheptyl or cyclooctyl;

$C_1$–$C_4$-haloalkyl can be linear or branched, such as, for example fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

$C_1$–$C_4$-haloalkoxy can be linear or branched, such as, for example, difluoromethoxy, trifluoromethoxy, chlorodifluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy, 2-fluoroethoxy or pentafluoroethoxy;

$C_1$–$C_4$-alkyl can be linear or branched, such as, for example, methyl, ethyl, 1-propyl, 2-propyl, 2-methyl-2-propyl, 2-methyl-1-propyl, 1-butyl or 2-butyl;

$C_2$–$C_4$-alkenyl can be linear or branched, such as, for example, ethenyl, 1-propen-3-yl, 1-propen-2-yl, 1-propen-1-yl, 2-methyl-1-propenyl, 1-butenyl or 2-butenyl;

$C_2$–$C_4$-alkynyl can be linear or branched, such as, for example, ethynyl, 1-propyn-1-yl, 1-propyn-3-yl, 1-butyn-4-yl or 2-butyn-4-yl;

$C_1$–$C_4$-alkoxy can be linear or branched, such as, for example, methoxy, ethoxy, propoxy, 1-methylethoxy, butoxy, 1-methylpropoxy, 2-methylpropoxy or 1,1-dimethylethoxy;

$C_3$–$C_6$-alkenyloxy can be linear or branched, such as, for example, allyloxy, 2-buten-1-yloxy or 3-buten-2-yloxy;

$C_1$–$C_4$-hydroxyalkyl can be linear or branched, such as, for example, hydroxymethyl, 1-hydroxyether-2-yl, $C_3$–$C_6$-alkynyloxy can be linear or branched, such as, for example, 2-propyn-1-yloxy, 2-butyn-1-yloxy or 3-butyn-2-yloxy;

$C_1$–$C_4$-alkylthio can be linear or branched, such as, for example, methylthio, ethylthio, propylthio, 1-methylethylthio, butylthio, 1-methylpropylthio, 2-methylpropylthio or 1,1-dimethylethylthio;

$C_1$–$C_4$-alkylcarbonyl can be linear or branched, such as, for example, acetyl, ethylcarbonyl or 2-propylcarbonyl;

$C_1$–$C_4$-alkoxycarbonyl can be linear or branched, such as, for example, methoxycarbonyl, ethoxycarbonyl, n-propoxycarbonyl, i-propoxycarbonyl or n-butoxycarbonyl;

$C_3$–$C_8$-alkylcarbonylalkyl can be linear or branched, such as, for example, 2-oxo-1-propyl, 3-oxo-1-butyl or 3-oxo-2-butyl $C_1$–$C_8$-alkyl can be linear or branched, such as, for example, $C_1$–$C_4$-alkyl, pentyl, hexyl, heptyl or octyl; halogen is, for example fluorine, chlorine, bromine, iodine.

The invention furthermore relates to those compounds from which compounds of the formula I can be liberated (called prodrugs).

Preferred prodrugs are those with which release takes place under conditions like those prevailing in certain compartments of the body, eg. in the stomach, intestine, bloodstream, liver.

The compounds, and the intermediates for preparing them, such as II, III and IV, may have one or more asymmetrically substituted carbon atoms. Such compounds can be in the form of pure enantiomers or pure diastereomers or mixture thereof. An enantiomerically pure compound is preferably used as active substance.

The invention furthermore relates to the use of the above-mentioned carboxylic acid derivatives for producing drugs, in particular for producing inhibitors of $ET_A$ and $ET_B$ receptors. The compounds according to the invention are particularly suitable as mixed antagonists as defined at the outset.

Compounds of the formula IV where Z is sulfur or oxygen can be prepared as described in WO 96/11914, also in enantiomerically pure form.

$$\underset{\text{II}}{\overset{R^4}{\underset{R^5}{\diagdown}}\!\!C\!\!\overset{O}{\diagup}\!\!\overset{R^1}{\diagup}} + R^6\!\!-\!\!Q\!\!-\!\!W\!\!-\!\!H \longrightarrow$$

$$\underset{\text{IV}}{R^6\!\!-\!\!Q\!\!-\!\!W\!\!-\!\!\overset{\overset{R^4}{|}}{\underset{\underset{R^4}{|}}{C}}\!\!-\!\!\overset{\overset{}{|}}{\underset{\underset{R^1}{|}}{CH}}\!\!-\!\!OH}$$

Compounds of the formula III are known or can be synthesized, for example, by reducing the corresponding carboxylic acids or esters thereof or by other conventional methods.

Carboxylic acid derivatives of the formula IV [sic] can also be prepared by reacting a compound of the formula IVa with an alcohol or thiol of the formula VII with acid catalysis.

$$\underset{\text{IVa}}{R^{18}\!\!-\!\!O\!\!-\!\!\overset{\overset{R^{16}}{|}}{\underset{\underset{R^{17}}{|}}{C}}\!\!\overset{H}{\underset{OH}{|}}\!\!-\!\!R^1} + \underset{\text{VII}}{R^{19}\!\!-\!\!W\!\!-\!\!H} \longrightarrow$$

$$\underset{\text{VI}}{R^{19}\!\!-\!\!W\!\!-\!\!\overset{\overset{R^{16}}{|}}{\underset{\underset{R^{17}}{|}}{C}}\!\!\overset{H}{\underset{OH}{|}}\!\!-\!\!R^1}$$

The indicated radicals have the following meanings:

$R^1$ has the meaning indicated for formula I $R^{16}$ and $R^{17}$, which may be identical or different, hydrogen or alkyl, alkenyl, alkynyl, phenyl, naphthyl, cycloalkyl, in each case unsubstituted or substituted, $R^{18}$ hydrogen or alkyl, alkenyl, alkynyl, phenyl, naphthyl, cycloalkyl, in each case unsubstituted or substituted, $R^{19}$ hydrogen or alkyl, alkenyl, alkynyl, phenyl, naphthyl, cycloalkyl, in each case unsubstituted or substituted, and the radicals preferably have the following meanings:

$R^1$ $COOR^7$ $R^{16}$ and $R^{17}$, which may be identical or different, alkyl, phenyl, naphthyl, cycloalkyl, in each case unsubstituted or substituted, $R^{18}$ alkyl, phenyl, cycloalkyl, in each case unsubstituted or substituted, $R^{19}$ alkyl, alkenyl, alkynyl, phenyl, cycloalkyl, in each case unsubstituted or substituted, and the following radicals are particularly preferred:

$R^1$ $COOCH_3$ $R^{16}$ $R^4$ $R^{17}$ $R^5$ $R^{18}$ alkyl, unsubstituted or substituted, in particular methyl $R^{19}$ $R^6$—Q.

The carboxylic acid derivatives of the formula IV can be prepared by this process by reacting a compound of the formula IVa with an alcohol or thiol of the formula III with acid catalysis

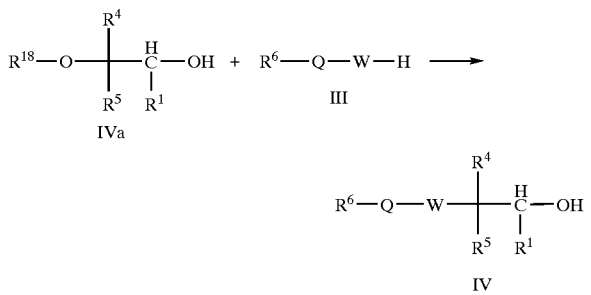

For this purpose, the compounds IVa and III are mixed without diluent or in a solvent which is inert for this reaction, and catalytic amounts of an acid such as p-toluenesulfonic acid are added. Examples of inert solvents are methylene chloride, benzene or toluene. Also suitable are those inert solvents which form an azeotrope with the alcohol $R^{18}OH$. In the case of methanol ($R^{18}=CH_3$), examples of these are chloroform or methyl acetate.

The reaction mixture is then stirred at from room temperature to the boiling point of the solvent. The resulting alcohol $R^{18}OH$ is removed by distilling out or reducing the pressure. This method is also suitable for preparing enantiomerically pure IV if the IVa starting material is enantiomerically pure.

Compounds of the formula IVa are known and are described, for example, in WO 96/11914.

The compounds according to the invention in which the substituents have the meanings stated for formula I can be prepared, for example, by reacting the carboxylic acid derivatives of the formula IV in which the substituents have the stated meanings with compounds of the formula V.

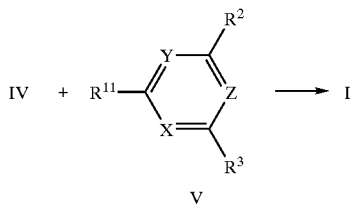

In formula V, $R^{11}$ is halogen or $R^{12}$—$SO_2$— where $R^{12}$ can be $C_1$–$C_4$-alkyl, $C_1$–$C_4$-haloalkyl or phenyl. In addition, at least one of the ring members X or Y or Z is nitrogen. The reaction preferably takes place in an inert solvent or diluent with the addition of a suitable base, ie. a base which deprotonates the intermediate IV, at a temperature in the range from room temperature to the boiling point of the solvent.

Compounds of type I with $R^1$=COOH can furthermore be obtained directly by deprotonating the intermediate IV where $R^1$ is COOH with two equivalents of a suitable base, and reacting with compounds of the formula V. This reaction also takes place in an inert solvent and at a temperature in the range from room temperature to the boiling point of the solvent.

Examples of such solvents and diluents are aliphatic, alicyclic and aromatic hydrocarbons, each of which may be chlorinated, such as hexane, cyclohexane, petroleum ether, naphtha, benzene, toluene, xylene, methylene chloride, chloroform, carbon tetrachloride, ethyl chloride and trichloroethylene, ethers such as diisopropyl ether, dibutyl ether, methyl tert-butyl ether, propylene oxide, dioxane and tetrahydrofuran, nitriles such as acetonitrile and propionitrile, amides such as dimethylformamide, dimethylacetamide and N-methylpyrrolidone, sulfoxides and sulfones, for example dimethyl sulfoxide and sulfolane.

Compounds of the formula V are known, and in some cases can be bought or prepared in a conventional way.

The base which can be used is an alkali metal or alkaline earth metal hydride such as sodium hydride, potassium hydride or calcium hydride, a carbonate such as an alkali metal carbonate, eg. sodium or potassium carbonate, an alkali metal or alkaline earth metal hydroxide such as sodium or potassium hydroxide, an organometallic compound such as butyllithium or an alkali metal amide such as lithium diisopropylamide or lithium amide.

Compounds of the formula I can also be prepared by starting from the corresponding carboxylic acids, ie. compounds of the formula I where $R^1$ is COOH, and converting first them in a conventional way into an activated form, such as a halide, an anhydride or imidazolide, and then reacting the latter with an appropriate hydroxyl compound $HOR^7$. This reaction can be carried out in conventional solvents and often requires the addition of a base, in which case those mentioned above are suitable. These two steps can also be simplified, for example, by allowing the carboxylic acid to act on the hydroxyl compound in the presence of a dehydrating agent such as a carbodiimide.

It is also possible to prepare compounds of the formula I by starting from the salts of the appropriate carboxylic acids, ie. from compounds of the formula I where $R^1$ is COR and R is OM [sic] where M can be an alkali metal cation or the equivalent of an alkaline earth metal cation. These salts can be reacted with many compounds of the formula R—A where A is a conventional nucleofugic leaving group, for example halogens such as chlorine, bromine, iodine, or aryl- or alkylsulfonyl which is unsubstituted or substituted by halogen, alkyl or haloalkyl, such as toluenesulfonyl and methylsulfonyl, or another equivalent leaving group. Compounds of the formula R—A with a reactive substituent A are known or can easily be obtained with general expert knowledge. This reaction can be carried out in conventional solvents and is advantageously undertaken with the addition of a base, in which case those mentioned above are suitable.

In some cases it is necessary to use generally known protective group techniques to prepare compounds I according to the invention. If, for example, $R^6$ is to be 4-hydroxyphenyl, it is possible first to protect the hydroxyl group as benzyl ether, which is then cleaved at a suitable stage in the reaction sequence.

Compounds of the formula I where $R^1$ is tetrazole [sic] can be prepared as described in WO 96/11914.

With a view to the biological effect, preferred carboxylic acid derivatives of the formula I, both as pure enantiomers or pure diastereomers or as mixture thereof, are those where the substituents have the following meanings:

$R^2$ hydrogen, hydroxyl, halogen, $N(C_1$–$C_4$-alkyl)$_2$, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, or $CR^2$ is linked to $CR^{10}$ as indicated below to give a 5- or 6-membered ring;

X nitrogen or methine;

Y nitrogen or methine;

Z nitrogen or $CR^{10}$, where $R^{10}$ is hydrogen or $C_1$–$C_4$-alkyl, or $CR^{10}$ forms together with $CR^2$ or $CR^3$ a 5- or 6-membered alkylene or alkenylene ring which can be substituted by one or two methyl groups and in which, in each case, one methylene group can be replaced by oxygen or sulfur, such as —$CH_2$—$CH_2$—O—, —$CH_2$—$CH_2$—$CH_2$—O—, —CH=CH—O—, —CH=CH—$CH_2$O—, —CH($CH_3$)—CH($CH_3$)—O—, —CH=C($CH_3$)—O—, —C($CH_3$)=C($CH_3$)—O—, or —C($CH_3$)=C($CH_3$)—S;

At least one of the ring members X, Y or Z is nitrogen.

$R^3$ hydrogen, hydroxyl, halogen, N($C_1$–$C_4$-alkyl)$_2$, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, or $CR^3$ is linked to $CR^{10}$ as indicated above to give a 5- or 6-membered ring;

$R^4$ and $R^5$ (which can be identical or different):
  phenyl or naphthyl, which can be substituted by one or more of the following radicals: halogen, nitro, cyano, hydroxyl, mercapto, amino, $C_1$–$C_4$-alkyl, $C_1$–$C_4$-haloalkyl, carboxyl, $C_1$–$C_4$-alkoxy, $C_1$–$C_4$-haloalkoxy, phenoxy, $C_1$–$C_4$-alkylthio, NH($C_1$–$C_4$-alkyl) or N($C_1$–$C_4$-alkyl)$_2$ or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or
  phenyl or naphthyl, which are connected together in the ortho positions by a direct linkage, a methylene, ethylene or ethenylene group, an oxygen or sulfur atom or an $SO_2$—, NH— or N-alkyl group, $C_3$–$C_8$-cycloalkyl;

$R^6$ $C_3$–$C_8$-cycloalkyl, it being possible for these radicals in each case to be substituted one or more times by: halogen, hydroxyl, mercapto, carboxyl, nitro, cyano, $C_1$–$C_4$-alkoxy, $C_1$–$C_4$-alkyl, $C_2$–$C_4$-alkenyl, $C_2$–$C_4$-alkynyl, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, NH($C_1$–$C_4$-alkyl), N($C_1$–$C_4$-alkyl)$_2$ or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  phenyl or naphthyl, each of which can be substituted by one or more of the following radicals: halogen, $R^{15}$, nitro, mercapto, carboxyl, cyano, hydroxyl, amino, $C_1$–$C_4$-alkyl, $C_2$–$C_4$-alkenyl, $C_2$–$C_4$-alkynyl, $C_3$–$C_6$-alkenyloxy, $C_1$–$C_4$-haloalkyl, $C_3$–$C_6$-alkynyloxy, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  a five- or six-membered heteroaromatic system containing one to three nitrogen atoms and/or one sulfur or oxygen atom, which can carry one to four halogen atoms and/or one to two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, where the phenyl radicals in turn can carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$R^{15}$ methyl, ethyl, methoxy or ethoxy which carry one of the following radicals: hydroxyl, carboxyl, amino, NH($C_1$–$C_4$-alkyl), N($C_1$–$C_4$-alkyl)$_2$, carboxamide [sic] or CON($C_1$–$C_4$-alkyl)$_2$;

W sulfur or oxygen;

Q $C_2$–$C_4$-alkyl, $C_3$–$C_4$-alkenyl, $C_3$–$C_4$-alkynyl, —S—$CH_2$—$CH_2$—, —O—$CH_2$—$CH_2$—, it being possible for each of these radicals to be substituted one or more times by: halogen, hydroxyl, mercapto, carboxyl, nitro, cyano, $C_1$–$C_4$-alkyl, $C_1$–$C_4$-alkoxy, $C_1$–$C_4$-alkylthio, $C_1$–$C_4$-haloalkoxy, $C_1$–$C_4$-alkoxycarbonyl, NH($C_1$–$C_4$-alkyl), N($C_1$–$C_4$-alkyl)$_2$ or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or Q forms together with $R^6$ the following ring systems: 2-indanyl, 3-indanyl, 1,2,3,4-tetrahydro-2-naphthyl, 1,2,3,4-tetrahydro-3-naphthyl, it being possible for the phenyl rings in each case to be substituted by: halogen, hydroxyl, mercapto, carboxyl, nitro, cyano, $C_1$–$C_4$-alkoxy, $C_1$–$C_4$-alkyl, $C_2$–$C_4$-alkenyl, $C_2$–$C_4$-alkynyl, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, amino, NH($C_1$–$C_4$-alkyl), N($C_1$–$C_4$-alkyl)$_2$ or phenyl.

Particularly preferred compounds of the formula I, both as pure enantiomers and pure diastereomers or mixtures thereof, are those where the substituents have the following meanings:

$R^2$ trifluoromethyl, $C_1$–$C_4$-alkyl, $C_1$–$C_4$-alkoxy, $C_1$–$C_4$-alkylthio, or $CR^2$ is linked to $CR^{10}$ as indicated below to give a 5- or 6-membered ring;

X nitrogen or methine;

Y nitrogen or methine;

Z nitrogen or $CR^{10}$ where $R^{10}$ is hydrogen or $C_1$–$C_4$-alkyl, or $CR^{10}$ forms together with $CR^2$ or $CR^3$ a 5- or 6-membered alkylene or alkenylene ring which can be substituted by one or two methyl groups and in which in each case a methylene group can be replaced by oxygen or sulfur, such as —$CH_2$—$CH_2$—O—, —$CH_2$—$CH_2$—$CH_2$—O—, —CH=CH—O—, —CH=CH—$CH_2$O—, —CH($CH_3$)—CH($CH_3$)—O—, —CH=C($CH_3$)—O—, —C($CH_3$)=C($CH_3$)—O—, or —C($CH_3$)=C($CH_3$)—S;

At least one of the ring members X, Y or Z is nitrogen $R^3$ trifluoromethyl, $C_1$–$C_4$-alkyl, $C_1$–$C_4$-alkoxy, $C_1$–$C_4$-alkylthio, or $CR^3$ is linked to $CR^{10}$ as indicated above to give a 5- or 6-membered ring;

$R^4$ and $R^5$ (which can be identical or different):
  phenyl or naphthyl, which can be substituted by one or more of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl) or N($C_1$–$C_4$-alkyl)$_2$ or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or
  phenyl or naphthyl, which are connected together in the ortho positions by a direct linkage, a methylene, ethylene or ethenylene group, an oxygen or sulfur atom or an $SO_2$—, NH— or N-alkyl group $C_5$–$C_7$-cycloalkyl;

$R^6$ $C_5$–$C_7$-cycloalkyl, it being possible for these radicals in each case to be substituted one or more times by: $C_1$–$C_4$-alkoxy, $C_1$–$C_4$-alkyl, $C_1$–$C_4$-alkylthio, halogen, hydroxyl, carboxyl, cyano, trifluoromethyl, acetyl, or phenyl which can be substituted one or more times, eg. one to three times, by halogen, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl or naphthyl, each of which can be substituted by one or more of the following radicals: halogen, $R^{15}$, nitro, mercapto, carboxyl, cyano, hydroxyl, amino, $C_1$–$C_4$-alkyl, $C_1$–$C_4$-haloalkyl, acetyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

a five- or six-membered heteroaromatic system containing one to three nitrogen atoms and/or one sulfur or oxygen atom, which can carry one to four halogen atoms and/or one to two of the following radicals: $C_1$–$C_4$-alkyl, $C_1$–$C_4$-haloalkyl, $C_1$–$C_4$-alkoxy, trifluoromethoxy, $C_1$–$C_4$-alkylthio, phenyl or phenoxy, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$R^{15}$ methoxy or ethoxy which carry one of the following radicals: hydroxyl, carboxyl, amino, NH($C_1$–$C_4$-alkyl), N($C_1$–$C_4$-alkyl)$_2$, carboxamide [sic] or CON($C_1$–$C_4$-alkyl)$_2$;

W sulfur or oxygen;

Q $C_2$–$C_4$-alkyl, $C_3$–$C_4$-alkenyl, $C_3$–$C_4$-alkynyl, —S—$CH_2$—$CH_2$—, —O—$CH_2$—$CH_2$—, it being possible for each of these radicals to be substituted one or more times by: halogen, hydroxyl, mercapto, carboxyl, $C_1$–$C_4$-alkyl, $C_1$–$C_4$-alkoxy, $C_1$–$C_4$-alkylthio, or phenyl which can be substituted one or more times, eg. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or Q forms together with $R^6$ the following ring systems: 2-indanyl, 3-indanyl, 1,2,3,4-tetrahydro-2-naphthyl, 1,2,3,4-tetrahydro-3-naphthyl, it being possible for the phenyl rings in each case to be substituted by: halogen, hydroxyl, mercapto, carboxyl, cyano, $C_1$–$C_4$-alkoxy, $C_1$–$C_4$-alkyl, $C_2$–$C_4$-alkenyl, $C_2$–$C_4$-alkynyl, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkoxycarbonyl, NH($C_1$–$C_4$-alkyl), N($C_1$–$C_4$-alkyl)$_2$ or phenyl.

The compounds of the present invention offer a novel therapeutic potential for the treatment of hypertension, pulmonary hypertension, myocardial infarct, chronic heart failure, angina pectoris, acute/chronic kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, kidney failure and hypertension caused by ischemia and intoxication, metastasis and growth of mesenchymal tumors, kidney failure induced by contrast agents, pancreatitis, gastrointestinal ulcers.

The compounds according to the invention surprisingly also show in some cases an antagonistic action on the neurokinin receptor.

This is particularly true of compounds of the formula I where $R^1$ is

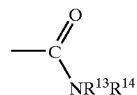

The invention furthermore relates to combination products consisting of endothelin receptor antagonists of the formula I and inhibitors of the renin-angiotensin system. Inhibitors of the renin-angiotensin system are renin inhibitors, angiotensin II antagonists and, in particular, angiotensin converting enzyme (ACE) inhibitors.

The invention further relates to combination products of β blockers and the abovementioned endothelin receptor antagonists, and of mixed ACE/neutral endopeptidase (NEP) inhibitors and the abovementioned endothelin receptor antagonists.

The combination products can be administered in a single pharmaceutical form or else in spatially separate forms. Administration may take place simultaneously or sequentially.

The dosage of the combination may be up to the maximum single dose in each case. However, it is also possible to employ lower doses than in the single therapy in each case.

These combination products are particularly suitable for the treatment and prevention of hypertension and its sequelae, and for the treatment of heart failure.

The good effect of the compounds can be shown in the following tests:

Receptor Binding Studies

Cloned human $ET_A$ or $ET_B$ receptor-expressing CHO cells were employed for binding studies.

Membrane Preparation

The $ET_A$ or $ET_B$ receptor-expressing CHO cells were grown in DMEM NUT MIX $F_{12}$ medium (Gibco, No. 21331-020) with 10% fetal calf serum (PAA Laboratories GmbH, Linz, No. A15-022), 1 mM glutamine (Gibco No. 25030-024), 100 U/ml penicillin and 100 μg/ml streptomycin (Gibco, Sigma No. P-0781). After 48 hours, the cells were washed with PBS and incubated with 0.05% trypsin-containing PBS at 37° C. for 5 minutes. Neutralization with medium was then carried out, and the cells were collected by centrifugation at 300×g.

For the membrane preparation, the cells were adjusted to a concentration of $10_8$ cells/ml of buffer (50 mM tris.HCL buffer, pH 7.4) and then disintegrated by ultrasound (Branson Sonifier 250, 40–70 seconds/constant/output 20).

Binding Assays

For the $ET_A$ and $ET_B$ receptor binding assays, the membranes were suspended in incubation buffer (50 mM tris-HCl, pH 7,4 with 5 mM $MnCl_2$, 40 μg/ml bacitracin and 0.2% BSA) at a concentration of 50 μg of protein per assay mixture, and incubated with 25 pM $^{125}$I-$ET_1$ ($ET_A$ receptor assay) or 25 pM $^{125}$I-$ET_3$ ($ET_B$ receptor assay) in the presence and absence of test substance at 25° C. The nonspecific binding was determined with $10^{-7}$ M $ET_1$. Filtration was carried out after 30 min through GF/B glass-fiber filters (Whatman, England) in a Skatron cell collector (Skatron, Lier, Norway) to separate free and bound radio ligands, and the filters were washed with ice-cold tris-HCl buffer, pH 7.4 with 0.2% BSA. The radioactivity collected on the filters was quantified using a Packard 2200 CA liquid scintillation counter.

Testing of the ET antagonists in vivo:

Male SD rats weighing 250–300 g were anesthetized with amobarbital, artificially ventilated, vagotomized and pithed. The carotid artery and jugular vein were catheterized.

Intravenous administration of 1 μg/kg ET1 to control animals led to a marked rise in blood pressure, which persisted for a lengthy period.

The test animals received i.v. injections of the test compounds (1 ml/kg) 30 min before administration of ET1. To determine the ET-antagonistic properties, the changes in blood pressure in the test animals were compared with those in the control animals.

Oral testing of the mixed $ET_A$ and $ET_B$ antagonists:

Normotensive male rats (Sprague Dawley, Janvier) weighing 250–350 g are pretreated orally with the test substances. 80 minutes later, the animals are anesthetized with urethane, and the carotid artery (for measuring the blood pressure) and the jugular vein (administration of big endothelin/endothelin 1) are catheterized.

After a stabilization period, big endothelin (20 μg/kg, administration volume 0.5 ml/kg) or ET1 (0.3 μg/kg, administration volume 0.5 ml/kg) is given intravenously. The blood pressure and heartrate are recorded continuously for 30 minutes. The marked and long-lasting changes in blood pressure are calculated as area under the curve (AUC). To determine the antagonistic effect of the test substances, the AUC for the animals treated with the substance is compared with the AUC for the control animals.

The compounds according to the invention can be administered orally or parenterally (subcutaneously, intravenously, intramuscularly, intraperitoneally) in a conventional way. Administration may also take place with vapors or sprays through the nasopharyngeal space.

The dosage depends on the age, condition and weight of the patient and on the mode of administration. As a rule, the daily dose of active substance is about 0.5–50 mg/kg of bodyweight on oral administration and about 0.1–10 mg/kg of bodyweight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. For this purpose, the active substances can be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of active substance.

SYNTHESIS EXAMPLES

Example 1

Methyl 2-Hydroxy-3-(2-(3,4-dimethoxyphenyl)ethoxy)-3,3-diphenylpropionate 7 g (27.5 mmol) of methyl 3,3-diphenyl-2,3-epoxypropionate and 5.5 g (30.2 mmol) of 2-(3,4-dimethoxyphenyl)ethanol were dissolved in 20 ml of dichloromethane and, at room temperature, 5 drops of boron trifluoride etherate were added. The solution was stirred for 2 hours. The solvent was then distilled off, and the residue (10.7 g, 89%) was immediately reacted further.

Example 2

2-Hydroxy-3-(2-(3,4-dimethoxyphenyl)ethoxy)-3,3-diphenylpropionic Acid 12 g (27.5 mmol) of methyl 2-hydroxy-3-(2-(3,4-dimethoxyphenyl)ethoxy)-3,3-diphenylpropionate were dissolved in 110 ml of dioxane, and 55 ml of 1 N NaOH solution were added. The mixture was stirred at 80° C. for 2 hours. Water was added to the mixture, and the aqueous phase was extracted twice with ether. The aqueous phase was acidified with 1 N aqueous HCl and extracted with ether, the organic phase was dried over magnesium sulfate, and the solvent was distilled off. The residue was recrystallized from ether/n-hexane, and 10.2 g (87%) of colorless crystals were isolated.

Melting point: 133–135° C.

Example 3

2-(4-Methoxy-6-methyl-2-pyrimidinyloxy)-3-(2-(3,4-dimethoxyphenyl)ethoxy)-3,3-diphenylpropionic Acid (I-482)

1 g (2.3 mmol) of 2-hydroxy-3-(2-(3,4-dimethoxyphenyl)ethoxy)-3,3-diphenylpropionic acid was introduced into 10 ml of DMF, and 340 mg of NaH (50% suspension) were added. After the mixture had been stirred for 15 minutes, 526 mg of 4-methoxy-6-methyl-2-methylsulfonylpyrimidine were added, and the mixture was stirred at room temperature for 3 hours. Water was added to the mixture, which was then extracted with ether. The aqueous phase was acidified with 1 N aqueous HCl, extracted with ether and dried over magnesium sulfate. The solvent was distilled off, the residue was purified by MPLC, and 655 mg (52%) of colorless powder were isolated after recrystallization from ether/n-hexane.

$^1$H-NMR (200 MHz): 7.2 ppm (10H, m), 6.8 (3H, m), 6.2 (1H, s), 6.18 (1H, s), 3.9 (9H, m), 3.8 (1H, m), 3.7 (1H, m), 2.85 (2H, tr), 2.2 (3H, s). EI-MS: $M^+$=544.

Example 4

Methyl 3,3-di(4-Ethylphenyl)-2,3-epoxypropionate

A solution of 15 ml (168 mmol) of methyl chloroacetate and 20 g (84 mmol) of 4,4'-diethylbenzophenone in 20 ml of THF was added dropwise to a suspension of 9.1 g (168 mmol) of sodium ethanolate in 80 ml of THF at −10° C. The mixture was warmed to room temperature and stirred for 2 hours. The mixture was added to water and extracted with ether. The organic phase was washed with sodium bicarbonate solution and citric acid solution and dried over magnesium sulfate, and the solvent was distilled off. 15.4 g of a crude oil were isolated and were immediately employed further.

Example 5

Methyl 2-Hydroxy-3-(2-(3,4-dimethoxyphenyl)ethoxy)-3,3-di-(4-ethyl-phenyl)propionate 6 g (19.3 mmol) of methyl 3,3-di(4-ethylphenyl)-2,3-epoxypropionate (crude) and 3.52 g (19.3 mmol) of 2-(3,4-dimethoxyphenyl)ethanol were dissolved in 20 ml of dichloromethane and, at room temperature, 5 drops of boron trifluoride etherate were added. The solution was stirred for 1.5 hours. The solvent was then distilled off, and the residue, a pale yellow oil (8.66 g, 91%), was immediately reacted further.

Example 6

2-Hydroxy-3-(2-(3,4-dimethoxyphenyl)ethoxy)-3,3-di(4-ethylphenyl)propionic Acid 9.2 g (19.3 mmol) of methyl 2-hydroxy-3-(2-(3,4-dimethoxyphenyl)ethoxy)-3,3-di(4-ethylphenyl)propionate were dissolved in 26 ml of dioxane, and 13 ml of 3 N NaOH solution were added. The mixture was stirred at 60° C. for 3 hours. Water was added to the mixture, and the aqueous phase was extracted twice with ether. The aqueous phase was acidified with 1 N aqueous HCl and extracted with ether, the organic phase was dried over magnesium sulfate, and the solvent was distilled off. 6.5 g (71%) of a yellowish oil were isolated and were immediately reacted further.

Example 7
2-(4-Methoxy-6-methyl-2-pyrimidinyloxy)-3-(2-(3,4-dimethoxyphenyl)ethoxy)-3,3-di(4-ethylphenyl)propionic Acid (I-116)

1.8 g (3.8 mmol) of 2-hydroxy-3-(2-(3,4-dimethoxyphenyl)ethoxy)-3,3-di(4-ethylphenyl)propionic acid were introduced into 20 ml of DMF, and 554 mg of NaH (50% suspension) were added. After the mixture had stirred for 15 minutes, 855 mg (4.2 mmol) of 4-methoxy-6-methyl-2-methylsulfonylpyrimidine were added, and the mixture was stirred at room temperature for 3 hours. Water was added to the mixture, which was then extracted with ether. The aqueous phase was acidified with 1 N aqueous HCl, extracted with ether and dried over magnesium sulfate. The solvent was distilled off and 540 mg (23%) of colorless powder were isolated after recrystallization from ether/n-hexane.

$^1$H-NMR (200 MHz): 7.0–7.4 ppm (10H, m), 6.8 (2H, d), 6.2 (1H, s), 6.15 (1H, s), 3.9 (3H, s), 3.8 (3H, s), 3.7 (1H, m), 3.5 (1H, m), 2.9 (2H, tr), 2.6 (4H, m), 2.3 (3H, s), 1.2 (6H, m). EI-MS: M$^+$=600.

Example 8
2-(4,6-Dimethyl-2-pyrimidinyloxy)-3-(3-phenyl-(2E)-propenoxy)-3,3-diphenylpropionic Acid (I-27)

1.12 g (3 mmol) of 2-hydroxy-3-(3-phenyl-(2E)-propenoxy)-3,3-diphenylpropionic acid were added to a suspension of 432 mg (9 mmol, 50%) of NaH in 20 ml of DMF, and the mixture was stirred at room temperature for 10 minutes. 614 mg (3.3 mmol) of 4,6-dimethyl-1-methylsulfonylpyrimidine were added, and the mixture was stirred for 16 hours, then diluted with 200 ml of water, acidified with 1 N hydrochloric acid and extracted with ether. The ether phase was extracted with 1 N sodium hydroxide solution, the aqueous phase was again acidified, and the product was extracted with ether. The organic phase was dried over magnesium sulfate and filtered, and the solvent was distilled off. The residue was recrystallized from ether/hexane, and 927 mg (65%) of crystalline product were isolated.

Melting point: 128–133° C.; $^1$H-NMR (200 MHz): 7.3 ppm (15H, m), 6.74 (1H, s), 6.7 (1H, d), 6.3 (1H, s), 6.2 (1H, dtr, 4.3 (1H, dd), 4.1 (1H, dd), 2.3 (6H, s). EI-MS: M$^+$=480.

Example 9
4,6-Dimethyl-1-methylthiopyrimidine 15 g (107 mmol) of 4,6-dimethyl-1-mercaptopyrimidine and 5.14 g of NaOH were dissolved in 175 ml of water. 12 ml (128 mmol) of dimethyl sulfate were added dropwise to this mixture at room temperature over the course of 10 minutes. After 1 hour, the aqueous phase was extracted 3 times with ether and dried over magnesium sulfate, and the solvent was distilled off. 15.9 g (97%) of crude product were isolated. $^1$H-NMR (270 MHz): 6.7 ppm (1H, s), 2.5 (3H, s), 2.3 (6H, s).

Example 10
4,6-Dimethyl-1-methylsulfonylpyrimidine 15.9 g (103 mmol) of 4,6-dimethyl-1-methylthiopyrimidine were introduced into 120 ml of dichloromethane and 110 ml of water. Chlorine gas was passed into saturation (yellow coloration) at 0° C. After the conversion was complete, excess chlorine was driven out with nitrogen, the aqueous phase was extracted with dichloromethane, and the collected organic phases were dried over magnesium sulfate. The solution was concentrated, and the product (14 g, 73%) was crystallized by adding ether.

Melting point: 79–80° C. $^1$H-NMR (270 MHz): 7.2 ppm (1H, s), 3.4 (3H, s), 2.6 (6H, s).

Example 11
Methyl (S)-2-Hydroxy-3-methoxy-3,3-diphenylpropionate 54.4 g (200 mmol) of (S)-2-hydroxy-3-methoxy-3,3-diphenylpropionic acid were introduced with 10.8 g (200 mmol) of sodium methoxide into 300 ml of DMF. 21 ml (210 mmol) of dimethylsulfate were added dropwise to this suspension over 15 minutes, during which the temperature rises to 50° C. and the suspension becomes mobile. The mixture was stirred overnight and then added to 1.5 l of water and ice. The aqueous phase was extracted twice with 500 ml of ether, and the ether phase was in turn washed with 200 ml of water twice. The organic phase was dried over magnesium sulfate, the desiccant was filtered off, and the solvent was distilled off. 55.8 g of an oil were isolated and were immediately processed further.

Example 12
Methyl (S)-2-Hydroxy-3-(2-(3,4-dimethoxyphenyl)ethoxy)-3,3-diphenylpropionate Variant A:

27.9 g of methyl (S)-2-hydroxy-3-methoxy-3,3-diphenylpropionate (100 mmol) were mixed with 1 g of p-toluenesulfonic acid and 18.2 g of 2-(3,4-dimethoxyphenyl)ethanol (100 mmol) in a flask and heated to 60° C. The pressure in the flask is reduced in order to distill out the methanol which is produced, and the mixture is stirred at 60° C. for a further 5 hours. For workup, the mixture is cooled and diluted with 300 ml of ether, and the organic phase is washed first with sodium bicarbonate solution and then several times with water. It is then dried with magnesium sulfate, and the desiccant is filtered off and the solvent is distilled off. A residue of 43 g of oil was isolated and could be employed immediately for the subsequent synthesis.

Variant B:

27.9 g of methyl (S)-2-hydroxy-3-methoxy-3,3-diphenylpropionate (100 mmol), 1 g of p-toluenesulfonic acid and 18.2 g (100 mmol) of 2-(3,4-dimethoxyphenyl)ethanol were dissolved in 75 ml of dichloromethane in a flask. The solution was heated and the dichloromethane was distilled out while simultaneously adding dichloromethane dropwise, in order to distill out the methanol which was produced, and the mixture was stirred at 60° C. for a further 5 hours. For workup, the mixture is cooled and diluted with 300 ml of ether, and the organic phase is washed first with sodium bicarbonate solution and then several times with water. It is then dried with magnesium sulfate, and the desiccant is filtered off and the solvent is distilled off. A residue of 43 g of oil was isolated and could be used immediately in the subsequent synthesis.

Example 13
(S)-2-Hydroxy-3-(2-(3,4-dimethoxyphenyl)ethoxy)-3,3-diphenylpropionic Acid 255 ml of 1 N sodium hydroxide solution were added to a solution of 74 g (170 mmol) of methyl (S)-2-hydroxy-3-(2-(3,4-dimethoxyphenyl)ethoxy-3,3-diphenylpropionate in 510 ml of dioxane, and the suspension was stirred at 50° C. for two hours. The mixture was diluted with 2.5 l of water and neutralized with citric acid. The aqueous phase was extracted twice with 500 ml of ether. The organic phase was then washed with water, dried over magnesium sulfate and filtered, and then the ether was distilled off. The residue was purified by crystallization from ether/n-hexane, and 70 g of crystals were isolated.

$^1$H-NMR (200 MHz): 7.3 ppm (10H, m), 6.8 (1H, dbr), 6.7 (1H, dbr), 6.6 (1H, sbr), 5.0 (1H, s), 3.9 (3H, s), 3.85 (3H, s), 3.6 (1H, dt), 3.4 (1H, OH), 3.2 (1H, dt), 2.8 (2H, t). $[\alpha]^{20}$=8.3 (1; ethanol).

Example 14

2-(4,6-(Dimethylpyrimidin-2-yloxy)-3-(2-(3,4-dimethoxyphenyl)ethoxy-3,3-diphenylpropionic Acid (I-445) and
(S)-2-(4,6-Dimethylpyrimidin-2-yloxy)-3-(2-(3,4-dimethoxyphenyl)ethoxy)-3,3-diphenylpropionic Acid (I-445 (S) Enantiomer) 55 g (130 mmol) of 2-hydroxy-3-(2-(3,4-dimethoxyphenyl)ethoxy-3,3-diphenylpropionic acid, dissolved in 150 ml of DMF, were added over the course of 15 minutes to 9 g (390 mmol) of lithium amide in 35 ml of DMF. 25 g (137 mmol) of 2-methylsulfone-4,6-dimethylpyrimidine [sic], dissolved in 75 ml of DMF, were slowly added dropwise to this, and the mixture was stirred at room temperature for 18 hours. For workup, the mixture was added to 2 l of ice-water and citric acid for neutralization. The crystals which separated out were filtered off with suction and washed with water. The moist crystals were dissolved in dichloromethane, the solution was dried over magnesium sulfate and filtered, and the solvent was distilled off. The oily residue was taken up in ether and extracted with 130 ml of 1 N sodium hydroxide solution, and the aqueous phase was neutralized with 130 ml of 1 N hydrochloric acid, whereupon crystals separated out. 64 g of product were isolated after drying.

$^1$H-NMR (200 MHz): 7.3 ppm (10H, m), 6.7 (4H, m), 6.3 (1H, s), 3.9 (3H, s), 3.85 (3H, s), 3.7 (1H, dt), 3.6 (1H, dt), 2.8 (2H, t), 2.3 (6H, s).

Melting point: 125–130° C. decomposition EI-MS: M$^+$=528.

(S)-2-(4,6-dimethylpyrimidin-2-yloxy)-3-(2-(3,4-dimethoxyphenyl)ethoxy)-3,3-diphenylpropionic acid was prepared in a similar way from (S)-2-hydroxy-3-(2-(3,4-dimethoxyphenyl)ethoxy)-3,3-diphenylpropionic acid and 2-methylsulfone-4,6-dimethylpyrimidine [sic] in the presence of lithium amide. $[\alpha]^{20}$=111 (1; ethanol).

Example 15

The following compounds were prepared as in Example 8
2-(4-Methoxy-6-methyl-2-pyrimidinyloxy)-3-(2-(4-methoxyphenyl)ethoxy)-3,3-di(4-ethylphenyl)propionic Acid (I-147)

Melting point: 150–155° C. EI-MS: M$^+$=570.
2-(4-Methoxy-5,6-dihydrofuro(2,3d)-2-pyrimidinyloxy)-3-(2-(4-chlorophenyl)ethoxy)-3,3-diphenylpropionic Acid (I-651)

Melting point: 150–152° C. EI-MS: M$^+$=546.
2-(4,6-Dimethyl-2-pyrimidinyloxy)-3-(2-(4-chlorophenyl) ethoxy)-3,3-diphenylpropionic Acid (I-713)

Melting point: 108° C. Decomposition EI-MS: M$^+$=502.
2-(4,6-Dimethoxy-2-pyrimidinyloxy)-3-(2-(4-chlorophenyl)ethoxy)-3,3-diphenylpropionic Acid Melting point: 165–167° C. EI-MS: M$^+$=534.
2-(4-Methoxy-6-methyl-2-pyrimidinyloxy)-3-(2-(4-chlorophenyl)ethoxy)-3,3-diphenylpropionic Acid (I-746)

Melting point: 93–98° C. EI-MS: M$^+$=518.
2-(4,6-Dimethyl-2-pyrimidinyloxy)-3-(2-(4-methoxyphenyl)ethoxy)-3,3-di(4-ethylphenyl)propionic Acid (I-148)

Melting point: 130–133° C. EI-MS: M$^+$=554.
2-(4-Methoxy-6-methyl-2-pyrimidinyloxy)-3-(2-(4-methylphenyl)ethoxy)-3,3-di(4-chlorophenyl)propionic Acid (I-710)

Melting point: 90–100° C. EI-MS: M$^+$=566.
2-(4-Methoxy-6-methyl-2-pyrimidinyloxy)-3-(3,3-diphenylpropoxy)-3,3-di(4-chlorophenyl)propionic Acid $^1$H-NMR(200 MHz): 7.3 ppm (18H, m), 6.25 (1H, s), 6.0 (1H, s), 4.0 (1H, tr), 3.8 (3H, s), 3.4 (2H, m), 2.2 (5H, m). EI-MS: M$^+$=642.

2-(4-Methoxy-6-methyl-2-pyrimidinyloxy)-3-(2-(3,4-dimethoxyphenyl)ethoxy)-3,3-di(4-chlorophenyl)propionic Acid (I-699)

Melting point: 100–110° C. EI-MS: M$^+$=612.
2-(4-Methoxy-6-methyl-2-pyrimidinyloxy)-3-(2-(2-methoxyphenyl)ethoxy)-3,3-di(4-chlorophenyl)propionic Acid (I-487)

Melting point: 85–90° C. EI-MS: M$^+$=582.
2-(4-Methoxy-5,6-dihydrofuro(2,3d)-2-pyrimidinyloxy)-3-(2-(3-methoxyphenyl)ethoxy)-3,3-di(4-chlorophenyl) propionic Acid (I-486)

Melting point: 190–195° C. EI-MS: M$^+$=610.
2-(4-Methoxy-5,6-dihydrofuro(2,3d)-2-pyrimidinyloxy)-3-(2-phenylethylthio)-3,3-di(4-chlorophenyl)propionic Acid Melting point: 173–175° C. $^1$H-NMR (200): 7.0–7.4 ppm (13H, m), 6.0 (1H, s), 4.7 (2H, tr), 3.8 (3H, s), 3.1 (2H, tr), 2.5 (4H, m).

2-(4-Methoxy-5,6-dihydrofuro(2,3d)-2-pyrimidinyloxy)-3-(2-(3,4-dimethoxyphenyl)ethoxy)-3,3-di(4-chlorophenyl) propionic Acid (I-635)

Melting point: 100–110° C. EI-MS: M$^+$=640.
2-(4-Methoxy-5,6-dihydrofuro(2,3d)-2-pyrimidinyloxy)-3-(2-(3,5-dimethoxyphenyl)ethoxy)-3,3-di(4-chlorophenyl) propionic Acid (1–593)

Melting point: 90–100° C. EI-MS: M$^+$=640.
2-(4-Methoxy-5,6-dihydrofuro(2,3d)-2-pyrimidinyloxy)-3-(2-(2-methoxyphenyl)ethoxy)-3,3-di(4-chlorophenyl) propionic Acid (I-164)

Melting point: 135–145° C. EI-MS: M$^+$=610.
2-(4-Methoxy-5,6-dihydrofuro(2,3d)-2-pyrimidinyloxy)-3-(3,3-diphenylpropoxy)-3,3-di(4-chlorophenyl)propionic Acid Melting point: 125–127° C. EI-MS: M$^+$=670.
2-(4-Methoxy-6,7-dihydro-5H-cyclopentapyrimidin-2-yloxy)-3-(3,3-diphenylpropoxy)-3,3-di(4-chlorophenyl) propionic Acid Melting point: 135–140° C. EI-MS: M$^+$=668.
2-(4-Methoxy-6,7-dihydro-5H-cyclopentapyrimidin-2-yloxy)-3-(2-phenylethylthio)-3,3-di(4-chlorophenyl) propionic Acid Melting point: 135–140° C. $^1$H-NMR (200): 7.0–7.5 ppm (13H, m), 5.9 (1H, s), 3.9 (3H, s), 2.6–2.8 (8H, m), 2.1 (2H, m).

2-(4-Methoxy-6,7-dihydro-5H-cyclopentapyrimidin-2-yloxy)-3-(2-(2-methoxyphenyl)ethoxy)-3,3-di(4-chlorophenyl)propionic Acid Melting point: 105–115° C. EI-MS: M$^+$=608.
2-(4-Methoxy-6,7-dihydro-5H-cyclopentapyrimidin-2-yloxy)-3-(2-(3-methoxyphenyl)ethoxy)-3,3-di(4-chlorophenyl)propionic Acid Melting point: 110–120° C. EI-MS: M$^+$=608.
2-(4-Methoxy-6,7-dihydro-5H-cyclopentapyrimidin-2-yloxy)-3-(2-(4-dimethylaminophenyl)ethoxy)-3,3-di(4-chlorophenyl)propionic Acid Melting point: 135–140° C. EI-MS: M⁺=621.

2-(4-Methoxy-6,7-dihydro-5H-cyclopentapyrimidin-2-yloxy)-3-(2-(3,4-dimethoxyphenyl)ethoxy)-3,3-di(4-chlorophenyl)propionic Acid Melting point: 125–130° C. EI-MS: M⁺=638.

2-(4-Methoxy-6,7-dihydro-5H-cyclopentapyrimidin-2-yloxy)-3-(2-(3,5-dimethoxyphenyl)ethoxy)-3,3-di(4-chlorophenyl)propionic Acid Melting point: 125–130° C. EI-MS: M⁺=638.

2-(4-Methoxy-5,6-dihydrofuro(2,3d)-2-pyrimidinyloxy)-3-(2-(4-methylphenyl)ethoxy)-3,3-diphenylpropionic Acid (I-370)

Melting point: 128–130° C. EI-MS: M⁺=526.

2-(4-Methoxy-6-methyl-2-pyrimidinyloxy)-3-(2-phenylethoxy)-3,3-diphenylpropionic Acid (I-719)

Melting point: 155° C. Decomposition EI-MS: M⁺=484.

2-(4,6-Dimethoxy-2-pyrimidinyloxy)-3-(2-phenylethoxy)-3,3-diphenylpropionic Acid Melting point: 203° C. Decomposition EI-MS: M⁺=500.

2-(4,6-Dimethyl-2-pyrimidinyloxy)-3-(2-phenylethoxy)-3,3-diphenyl propionic Acid (I-720)

Melting point: 130–133° C. EI-MS: M⁺=468.

2-(4-Methoxy-5,6-dihydrofuro(2,3d)-2-pyrimidinyloxy)-3-(2-phenylethoxy)-3,3-diphenylpropionic Acid (I-657)

Melting point: 138–142° C. EI-MS: M⁺=512.

2-(4,6-Dimethoxy-2-pyrimidinyloxy)-3-(2-(4-methylphenyl)ethoxy)-3,3-diphenylpropionic Acid Melting point: 155–158° C. EI-MS: M⁺=514.

2-(4-Methoxy-6-methyl-2-pyrimidinyloxy)-3-(2-(4-methylphenyl)ethoxy)-3,3-diphenylpropionic Acid (I-465)

Melting point: 145–147° C. EI-MS: M⁺=498.

2-(4-Methoxy-6-methyl-2-pyrimidinyloxy)-3-(3-(4-methoxyphenyl)propoxy)-3,3-diphenylpropionic Acid (I-554)

Melting point: 160–165° C. EI-MS: M⁺=528.

2-(4,6-Dimethyl-2-pyrimidinyloxy)-3-(3-(4-methoxyphenyl)propoxy)-3,3-diphenylpropionic Acid (I-555)

Melting point: 165–170° C. EI-MS: M⁺=512.

2-(4-Methoxy-6-methyl-2-pyrimidinyloxy)-3-(3-(3,4,5-trimethoxyphenyl)propoxy)-3,3-diphenylpropionic Acid (I-335)

¹H-NMR (200): 7.2–7.4 ppm (10H, m), 6.3 (2H, s), 6.2 (2H, s), 3.8 (3H, s), 3.75 (10H, s), 3.4 (2H, m), 2.6 (2H, m), 2.25 (3H, s), 1.9 (2H, m). EI-MS: M⁺=588.

2-(4,6-Dimethyl-2-pyrimidinyloxy)-3-(3-(3,4,5-trimethoxyphenyl)propoxy)-3,3-diphenylpropionic Acid (I-336)

¹H-NMR (200): 7.2–7.5 ppm (10H, m), 6.6 (1H, s), 6.3 (3H, S), 3.8 (9H, s), 3.4 (2H, m), 2.6 (2H, m), 2.3 (6H, s), 1.9 (2H, m). EI-MS: M⁺=572.

2-(4-Methoxy-6-methyl-2-pyrimidinyloxy)-3-(3-(2-chlorophenyl)propoxy)-3,3-diphenylpropionic Acid (I-383)

¹H-NMR (200): 7.1–7.5 ppm (14H, m), 6.24 (1H, s), 6.23 (1H, s), 3.8 (3H, s), 3.4 (2H, m), 2.75 (2H, m), 2.25 (3H, s), 1.9 (2H, m). EI-MS: M⁺=532.

2-(4,6-Dimethyl-2-pyrimidinyloxy)-3-(3-(2-chlorophenyl)propoxy)-3,3-diphenylpropionic Acid (I-384)

Melting point: 172–178° C. EI-MS: M⁺=516.

2-(4,6-Dimethyl-2-pyrimidinyloxy)-3-(3-(4-chlorophenyl)propoxy)-3,3-diphenylpropionic Acid (I-251)

¹H-NMR (200): 7.0–7.4 ppm (14H, m), 6.6 (1H, s), 6.3 (1H, s), 3.5 (2H, m), 2.7 (2H, m), 2.3 (6H, m), 1.9 (2H, m). EI-MS: M⁺=516.

2-(4,6-Dimethyl-2-pyrimidinyloxy)-3-(3-(3,4-dimethoxyphenyl)propoxy)-3,3-diphenylpropionic Acid (I-490))

¹H-NMR (200): 7.1–7.5 ppm (10H, m), 6.74 (1H, s), 6.7 (3H, S), 6.3 (1H, s), 3.8 (6H, s), 3.5 (2H, m), 2.7 (2H, m), 2.3 (6H, s), 1.9 (2H, m). EI-MS: M⁺=542.

2-(4-Methoxy-6-methyl-2-pyrimidinyloxy)-3-(2-(4-propoxyphenyl)ethoxy)-3,3-diphenylpropionic Acid (I-69)

Melting point: 115–119° C. EI-MS: M⁺=542.

2-(4-Methoxy-6-methyl-2-pyrimidinyloxy)-3-(2-(4-butoxyphenyl)ethoxy)-3,3-diphenylpropionic Acid (I-71)

Melting point: 118–122° C. EI-MS: M⁺=556.

2-(4,6-Dimethyl-2-pyrimidinyloxy)-3-(2-(4-butoxyphenyl)ethoxy)-3,3-diphenylpropionic Acid (I-70)

Melting point: 122–125° C. EI-MS: M⁺=540.

2-(4-Methoxy-6-methyl-2-pyrimidinyloxy)-3-(3-phenyl-(2E)-propenoxy)-3,3-diphenylpropionic Acid (I-44)

Melting point: 171–174° C. EI-MS: M⁺=496.

2-(4-Methoxy-6-methyl-2-pyrimidinyloxy)-3-(3-(2-methylphenyl)propoxy)-3,3-diphenylpropionic Acid (I-107)

Decomposition: 144–146° C. EI-MS: M⁺=512.

2-(4,6-Dimethyl-2-pyrimidinyloxy)-3-(3-(2-methylphenyl)propoxy)-3,3-diphenylpropionic Acid (I-90)

Decomposition: 173–176° C. EI-MS: M⁺=496.

2-(4-Methoxy-6-methyl-2-pyrimidinyloxy)-3-(3-(4-methylphenyl)propoxy)-3,3-diphenylpropionic Acid (1-363)

Decomposition: 158–161° C. EI-MS: M⁺=512.

2-(4,6-Dimethyl-2-pyrimidinyloxy)-3-(3-(4-methylphenyl)propoxy)-3,3-diphenylpropionic Acid (I-346)

Decomposition: 163–167° C. EI-MS: M⁺=496.

2-(4-Methoxy-6-methyl-2-pyrimidinyloxy)-3-(2-(4-methylthiophenyl)ethoxy)-3,3-diphenylpropionic Acid (I-246)

Decomposition: 136–138° C. EI-MS: M⁺=530.

2-(4,6-Dimethyl-2-pyrimidinyloxy)-3-(2-(4-methylthiophenyl)ethoxy)-3,3-diphenylpropionic Acid (I-217)

Decomposition: 166–169° C. EI-MS: M⁺=514.

2-(4-Methoxy-6-methyl-2-pyrimidinyloxy)-3-(2-(4-ethoxy-3-methoxyphenyl)ethoxy)-3,3-diphenylpropionic Acid (1-145)

Decomposition: 141–145° C. EI-MS: M⁺=558.

2-(4-Methoxy-6-methyl-2-pyrimidinyloxy)-3-(2-(4-ethoxyphenyl)ethoxy)-3,3-diphenylpropionic Acid (I-510)

Decomposition: 131–135° C. EI-MS: M⁺=528.

2-(4-Methoxy-6-methyl-2-pyrimidinyloxy)-3-(2-(4-i-propylphenyl)ethoxy)-3,3-diphenylpropionic Acid (I-705)

¹H-NMR (200 MHz, DMSO): 7.0–7.35 ppm (14H, m), 6.35 (1H, s), 6.1 (1H, s), 4.0 (1H, m), 3.9 (3H, s), 3.8 (3H, s), 3.7 (1H, m), 2.9 (3H, m), 2.2 (3H, s), 1.1 (6H, d). EI-MS: M⁺=526.

2-(4-Methoxy-6-methyl-2-pyrimidinyloxy)-3-(2-(3,4-methylenedioxyphenyl)ethoxy)-3,3-diphenylpropionic Acid (1-568)

Decomposition: 146–148° C. EI-MS: M⁺=528.

2-(4-Methoxy-5,6-dihydrofuro(2,3d)-2-pyrimidinyloxy)-3-(2-(3,4-methylenedioxyphenyl)ethoxy)-3,3-diphenylpropionic Acid (I-501)

Decomposition: 145–149° C. EI-MS: M⁺=556.

2-(4-Methoxy-5,6-dihydrofuro(2,3d)-2-pyrimidinyloxy)-3-(2-(4-ethoxy-3-methoxyphenyl)ethoxy)-3,3-diphenylpropionic Acid (I-735)

¹H-NMR (270 MHz, DMSO): 7.1–7.4 ppm (10H, m), 6.85 (2H, m), 6.7 (1H, d), 6.1 (1H, s), 4.6 (2H, tr), 4.0 (3H, m), 3.85 (3H, s), 3.75 (3H, s), 3.65 (1H, m), 3.05 (2H, tr), 2.8 (2H, m), 1.25 (3H, m). EI-MS: M⁺=586.

2-(4-Methoxy-5,6-dihydrofuro(2,3d)-2-pyrimidinyloxy)-3-(2-(4-ethoxyphenyl)ethoxy)-3,3-diphenylpropionic Acid (I-407)

¹H-NMR (270 MHz, DMSO): 7.1–7.4 ppm (12H, m), 6.8 (2H, d), 6.1 (1H, s), 4.65 (2H, tr), 3.95 (3H, m), 3.8 (3H, s), 3.65 (1H, m), 3.05 (2H, tr), 2.8 (2H, m), 1.25 (3H, m). EI-MS: M⁺=556.

2-(4,6-Dimethyl-2-pyrimidinyloxy)-3-(2-(4-ethoxy-3-methoxyphenyl)ethoxy)-3,3-diphenylpropionic Acid (I-146)

Decomposition: 129–134° C. EI-MS: M⁺=542.

2-(4,6-Dimethyl-2-pyrimidinyloxy)-3-(2-(3,4-methylenedioxyphenyl)ethoxy)-3,3-diphenylpropionic Acid (I-569)

¹H-NMR (270 MHz, DMSO): 7.1–7.4 ppm (10H, m), 6.9 (1H, s), 6.8 (2H, m), 6.7 (1H, d), 6.2 (1H, s), 6.0 (2H, s), 3.95 (3H, m), 3.65 (1H, m), 2.8 (2H, m), 2.3 (6H, s). EI-MS: M⁺=512.

2-(4,6-Dimethyl-2-pyrimidinyloxy)-3-(2-(4-ethoxyphenyl)ethoxy)-3,3-diphenylpropionic Acid (I-473)

Decomposition: 145–148° C. EI-MS: M⁺=512.

2-(4-Methoxy-5,6-dihydrofuro(2,3d)-2-pyrimidinyloxy)-3-(2-(4-i-propylphenyl)ethoxy)-3,3-diphenylpropionic Acid (I-604)

¹H-NMR (270 MHz, DMSO): 7.1–7.4 ppm (14H, m), 6.1 (1H, s), 4.6 (2H, tr), 3.9 (1H, m), 3.8 (3H, s), 3.6 (1H, m), 3.0 (2H, tr), 2.8 (3H, m), 1.1 (6H, d). EI-MS: M⁺=554.

2-(4,6-Dimethyl-2-pyrimidinyloxy)-3-(2-(4-i-propylphenyl)ethoxy)-3,3-diphenylpropionic Acid (I-672)

Decomposition: 156–160° C. EI-MS: M⁺=510.

2-(4-Methoxy-5,6-dihydrofuro(2,3d)-2-pyrimidinyloxy)-3-(2-(4-methoxyphenyl)ethoxy)-3,3-di(4-methylphenyl) propionic Acid (I-517)

¹H-NMR (200 MHz, DMSO): 7.0–7.3 ppm (10H, m), 6.8 (2H, d), 6.0 (1H, s), 4.6 (2H, tr), 3.85 (3H, s), 3.8 (1H, m), 3.7 (3H, s), 3.6 (1H, m), 3.0 (2H, tr), 2.8 (2H, tr), 1.1 (6H, d). EI-MS: M⁺=570.

2-(4-Methoxy-6-methyl-2-pyrimidinyloxy)-3-(2-(4-methoxyphenyl)ethoxy)-3,3-diphenylpropionic Acid (I-622)

¹H-NMR (270 MHz, DMSO): 7.1–7.4 ppm (12H, m), 6.8 (2H, d), 6.4 (1H, s), 6.1 (1H, s), 4.0 (1H, m), 3.7 (3H, s), 3.7 (1H, m), 2.8 (2H, tr), 2.3 (3H, s). EI-MS: M⁺=514.

2-(4,6-Dimethyl-2-pyrimidinyloxy)-3-(2-(4-methoxyphenyl)ethoxy)-3,3-diphenylpropionic Acid (I-585)

¹H-NMR (200 MHz, DMSO): 7.1–7.4 ppm (12H, m), 6.8 (3H, m), 6.1 (1H, s), 4.0 (1H, m), 3.7 (3H, s), 3.6 (1H, m), 2.8 (2H, r), 2.3 (6H, s). EI-MS: M⁺=498.

2-(4-Methoxy-6-methyl-2-pyrimidinyloxy)-3-(3-phenylpropoxy)-3,3-diphenylpropionic Acid (I-499)

Decomposition: 153–155° C. EI-MS: M⁺=498.

2-(4,6-Dimethyl-2-pyrimidinyloxy)-3-(3-phenylpropoxy)-3,3-diphenylpropionic Acid (I-500)

Decomposition: 148–151° C. EI-MS: M⁺=482.

The compounds listed in Table 1 can be prepared in a similar way or as described in the general part.

TABLE I

[sic]

$$R^6-Q-W-\underset{\underset{R^5}{|}}{\overset{\overset{R^4}{|}}{C}}-\underset{\underset{R^1}{|}}{CH}-O-\begin{array}{c}Y\\\phantom{}\\X\end{array}\begin{array}{c}R^2\\\\\\R^3\end{array}Z$$

I

| No. | R¹ | R⁴, R⁵ | Q | R⁶ | R² | R³ | Z | X | Y | W |
|---|---|---|---|---|---|---|---|---|---|---|
| I-1 | COOH | phenyl | —CH₂—CH₂— | phenyl | OMe | Me | CH | N | N | S |
| I-2 | COOMe | phenyl | —CH₂—CH₂— | phenyl | CF₃ | Me | CH | N | N | O |
| I-3 | COOH | 4-Br-phenyl | —CH₂—CH₂— | phenyl | OMe | OMe | CH | N | N | O |
| I-4 | COOH | phenyl | —CH₂—C(CH₃)₂— | phenyl | OMe | Me | CH | N | N | O |
| I-5 | COOH | 4-Cl-phenyl | —CH₂—CH₂—CH₂— | 3,4-di-OMe-phenyl | Me | Me | CH | N | N | O |
| I-6 | COOH | 4-Cl-phenyl | —CH₂—CH₂—CH₂— | 3,4-di-OMe-phenyl | Me | Me | N | N | N | O |
| I-7 | COOH | phenyl | —CH₂—CH₂— | 3,4-di-Cl-phenyl | Me | Me | CH | N | N | O |
| I-8 | COOH | phenyl | —CH₂—CH₂— | phenyl | Me | Me | N | N | CH | O |
| I-9 | COOH | phenyl | —CH₂—CH₂— | phenyl | ethyl | Me | N | N | N | O |
| I-10 | COOH | phenyl | —CH=CH—CH₂— | phenyl | ethyl | Me | CH | N | N | O |
| I-11 | COOH | phenyl | —CH=CH—CH₂— | phenyl | OMe | CH₂—CH₂—CH₂—C | N | N | O |
| I-12 | COOH | phenyl | —CH=CH—CH₂— | phenyl | OMe | O—CH₂—CH₂—C | N | N | O |
| I-13 | COOH | phenyl | —CH₂—CH₂— | phenyl | OMe | CH₂—CH₂—CH₂—C | N | N | S |
| I-14 | COOEt | phenyl | —CH₂—CH₂— | phenyl | OMe | O—CH₂—CH₂—C | N | N | O |
| I-15 | COOH | 4-Et-phenyl | —CH₂—CH₂— | 4-SMe-phenyl | Me | Me | CH | N | N | O |
| I-16 | COOH | 4-Et-phenyl | —CH₂—CH₂— | 4-SMe-phenyl | Me | Me | N | N | N | O |
| I-17 | COOMe | phenyl | —CH₂—CH₂— | 4-OMe-phenyl | OMe | Me | CH | N | N | O |
| I-18 | COOEt | phenyl | —CH₂—CH₂— | 4-OMe-phenyl | Me | Me | CH | N | N | S |
| I-19 | tetrazole [sic] | phenyl | —CH₂—CH₂— | 4-OMe-phenyl | OMe | O—CH₂—CH₂—C | N | N | N | O |
| I-20 | COOH | phenyl | —C(CH₃)₂—CH₂— | 4-OMe-phenyl | OMe | O—CH₂—CH₂—C | N | N | N | O |
| I-21 | COOH | phenyl | —CH₂—C(CH₃)₂— | 4-OMe-phenyl | OMe | O—CH₂—CH₂—C | N | N | N | O |
| I-22 | COOH | 4-Cl-phenyl | —CH₂—CH₂—CH₂— | 4-OMe-phenyl | OMe | O—CH₂—CH₂—C | N | N | N | O |
| I-23 | COOH | 4-Cl-phenyl | —CH₂—CH₂—CH₂— | 3,4-di-OMe-phenyl | OMe | Me | CH | N | N | O |
| I-24 | COOH | 4-Br-phenyl | —CH₂—CH₂— | 4-OMe-phenyl | OMe | OMe | CH | N | N | O |
| I-25 | COOH | phenyl | —CH₂—CH₂— | 4-OMe-phenyl | OMe | Me | N | N | N | O |
| I-26 | COOH | phenyl | —CH₂—CH₂— | 4-OMe-phenyl | Me | Me | N | N | CH | O |
| I-27 | COOH | phenyl | —CH=CH—CH₂— | phenyl | Me | Me | CH | N | N | O |
| I-28 | COOH | phenyl | —CH=CH—CH₂— | phenyl | Me | Me | N | N | N | O |
| I-29 | COOH | phenyl | —CH₂—CH₂— | 4-OMe-phenyl | ethyl | Me | N | N | N | O |
| I-30 | COOH | phenyl | —CH₂—CH₂— | 4-OMe-phenyl | OMe | CH₂—CH₂—CH₂—C | N | N | S |
| I-31 | COOH | 4-Et-phenyl | —CH₂—CH₂— | 3-OMe-phenyl | OMe | O—CH₂—CH₂—C | N | N | N | O |
| I-32 | COOH | 4-Et-phenyl | —CH₂—CH₂— | 4-SMe-phenyl | OMe | Me | CH | N | N | O |

TABLE I-continued

[sic]

$$R^6-Q-W-\underset{R^5}{\overset{R^4}{C}}-\underset{R^1}{\overset{}{CH}}-O-\underset{X}{\overset{Y}{\underset{}{\bigcirc}}}\overset{R^2}{\underset{R^3}{Z}}$$ I

| No. | R¹ | R⁴, R⁵ | Q | R⁶ | R² | R³ | Z | X | Y | W |
|---|---|---|---|---|---|---|---|---|---|---|
| I-33 | COOEt | phenyl | —CH₂—CH₂— | 4-OMe-phenyl | OMe | O—CH₂—CH₂—C | N | N | N | O |
| I-34 | COOH | phenyl | —CH₂—CH₂— | 3,4-di-OMe-phenyl | OMe | O—CH₂—CH₂—C | N | N | N | S |
| I-35 | COOMe | phenyl | —C(CH₃)₂—CH₂— | 3,4-di-OMe-phenyl | OMe | Me | N | N | CH | S |
| I-36 | COOH | phenyl | —C(CH₃)₂—CH₂— | 3,4-di-OMe-phenyl | ethyl | Me | CH | N | N | O |
| I-37 | COOH | 4-Br-phenyl | —CH₂—CH₂— | 3,4-di-OMe-phenyl | CF₃ | Me | CH | N | N | O |
| I-38 | COOH | 4-Cl-phenyl | —CH₂—CH₂—CH₂— | 4-OMe-phenyl | Me | Me | N | N | N | O |
| I-39 | COOH | 4-Cl-phenyl | —CH₂—CH₂—CH₂— | 4-OMe-phenyl | ethyl | Me | CH | N | N | O |
| I-40 | COOH | phenyl | —CH₂—CH₂— | 3,4-di-OMe-phenyl | OMe | Me | CH | N | N | O |
| I-41 | COOH | phenyl | —CH₂—CH₂— | 3,4-di-OMe-phenyl | SMe | Me | CH | N | N | O |
| I-42 | COOH | phenyl | —CH₂—CH₂— | 3,4-di-OMe-phenyl | Me | Me | N | N | CH | O |
| I-43 | COOH | phenyl | —CH═CH—CH₂— | phenyl | CF₃ | Me | CH | N | N | O |
| I-44 | COOH | phenyl | —CH═CH—CH₂— | phenyl | OMe | Me | CH | N | N | O |
| I-45 | COOH | phenyl | —CH₂—CH₂— | 3,4-di-OMe-phenyl | ethyl | Me | CH | N | N | S |
| I-46 | COOBzl | phenyl | —CH₂—CH₂— | 3,4-di-OMe-phenyl | OMe | CH₂—CH₂—CH₂—C | N | N | N | O |
| I-47 | COOH | 4-Et-phenyl | —CH₂—CH₂— | 3-OMe-phenyl | Me | Me | N | N | N | O |
| I-48 | COOH | 4-Et-phenyl | —CH₂—CH₂— | 3-OMe-phenyl | ethyl | Me | CH | N | N | O |
| I-49 | COOH | 4-F-phenyl | —CH₂—CH₂— | 3,4-di-OMe-phenyl | OMe | O—CH₂—CH₂—C | N | N | N | O |
| I-50 | COOH | phenyl | —C(CH₃)₂—CH₂— | 3,4,5-tri-OMe-phenyl | CF₃ | Me | CH | N | N | O |
| I-51 | COOH | phenyl | —CH₂—CH₂— | 3-Me-4-Et-phenyl | OMe | CF₃ | CH | N | N | O |
| I-52 | COOH | phenyl | —CH₂—CH₂— | 3-Me-4-Et-phenyl | OMe | Me | CH | N | N | O |
| I-53 | COOH | 4-F-phenyl | —CH₂—CH₂— | 4-Br-phenyl | Me | Me | N | N | N | O |
| I-54 | COOH | 4-Cl-phenyl | —CH₂—CH₂—CH₂— | 4-OMe-phenyl | OMe | Me | CH | N | N | O |
| I-55 | COOH | 4-Cl-phenyl | —CH₂—CH₂—CH₂— | 4-OMe-phenyl | Me | Me | CH | N | N | O |
| I-56 | COOH | phenyl | —CH₂—CH₂— | 4-Br-phenyl | Me | Me | N | N | CH | O |
| I-57 | COOH | phenyl | —CH₂—CH₂— | 3-Br-phenyl | ethyl | Me | CH | N | N | S |
| I-58 | COOH | phenyl | —CH₂—CH₂— | 2-Me-phenyl | OMe | CH₂—CH₂—CH₂—C | N | N | N | O |
| I-59 | COOH | phenyl | —CH═CH—CH₂— | 4-Me-phenyl | OMe | CH₂—CH₂—CH₂—C | N | N | N | O |
| I-60 | COOH | phenyl | —CH═CH—CH₂— | 4-Me-phenyl | OMe | O—CH₂—CH₂—C | N | N | N | O |
| I-61 | COOH | 4-F-phenyl | —CH₂—CH₂— | 3-Me-phenyl | OMe | O—CH₂—CH₂—C | N | N | N | O |
| I-62 | COOH | phenyl | —CH₂—CH₂— | 3-Me-4-SMe-phenyl | CF₃ | Me | CH | N | N | O |
| I-63 | COOH | 4-Et-phenyl | —CH₂—CH₂— | 3-OMe-phenyl | OMe | Me | CH | N | N | O |
| I-64 | COOH | 4-Et-phenyl | —CH₂—CH₂— | 3-OMe-phenyl | Me | Me | CH | N | N | O |
| I-65 | tetrazole [sic] | phenyl | —CH₂—CH₂— | 4-SMe-phenyl | Me | OMe | CH | N | N | O |
| I-66 | COOH | 3-OMe-phenyl | —CH₂—CH₂— | 4-SMe-phenyl | OMe | Me | CH | N | N | O |
| I-67 | COOH | phenyl | —O—CH₂—CH₂— | 4-SMe-phenyl | Me | Me | CH | N | N | O |
| I-68 | COOH | phenyl | —CH₂—CH₂— | 4-n-propoxy-phenyl | Me | Me | CH | N | N | O |
| I-69 | COOH | phenyl | —CH₂—CH₂— | 4-n-propoxy-phenyl | OMe | Me | CH | N | N | O |
| I-70 | COOH | phenyl | —CH₂—CH₂— | 4-n-butoxy-phenyl | Me | Me | CH | N | N | O |
| I-71 | COOH | phenyl | —CH₂—CH₂— | 4-n-butoxy-phenyl | OMe | Me | CH | N | N | O |
| I-72 | COOH | phenyl | —O—CH₂—CH₂— | 4-SMe-phenyl | Me | Me | CH | N | CH | O |
| I-73 | COOH | phenyl | —O—CH₂—CH₂— | 4-SMe-phenyl | ethyl | Me | CH | N | N | S |
| I-74 | COOH | phenyl | —CH₂—CH₂—CH₂— | 2-Me-phenyl | ethyl | Me | CH | N | N | O |
| I-75 | COOH | phenyl | —CH₂—CH₂—CH₂— | 2-Me-phenyl | OMe | CH₂—CH₂—CH₂—C | N | N | N | O |
| I-76 | COOH | phenyl | —CH₂—CH₂— | 2-Me-4-SMe-phenyl | OMe | CH₂—CH₂—CH₂—C | N | N | N | O |
| I-77 | COOH | phenyl | —C(CH₃)₂—CH₂— | 4-SMe-phenyl | OMe | O—CH₂—CH₂—C | N | N | N | O |
| I-78 | COOMe | phenyl | —CH₂—CH₂— | 4-OEt-3-OMe-phenyl | CF₃ | Me | CH | N | N | O |
| I-79 | COOH | phenyl | —CH═CH—CH₂— | 4-Me-phenyl | Me | Me | N | N | N | O |
| I-80 | COOH | phenyl | —CH═CH—CH₂— | 4-Me-phenyl | ethyl | Me | CH | N | N | O |
| I-81 | COOH | phenyl | —CH₂—CH₂— | 4-(di-Me-amino)-phenyl | OMe | O—CH₂—CH₂—C | N | N | N | O |
| I-82 | COOH | 4-Cl-phenyl | —CH₂—CH₂— | 4-OMe-phenyl | OMe | Me | CH | N | N | O |
| I-83 | COOH | 4-Et-phenyl | —CH₂—CH₂— | 3,4-di-OMe-phenyl | ethyl | Me | CH | N | N | O |
| I-84 | COOH | 4-Et-phenyl | —CH₂—CH₂— | 3,4-di-OMe-phenyl | OMe | O—CH₂—CH₂—C | N | N | N | O |
| I-85 | COOH | 3-OMe-phenyl | —CH₂—CH₂— | 4-OEt-3-OMe-phenyl | OMe | Me | CH | N | N | O |
| I-86 | COOH | phenyl | —O—CH₂—CH₂— | 4-OEt-3-OMe-phenyl | Me | Me | CH | N | N | O |
| I-87 | COOH | phenyl | —S—CH₂—CH₂— | 3-OMe-4-Cl-phenyl | Me | Me | CH | N | N | O |
| I-88 | COOH | phenyl | —CH₂—CH₂— | 3-OMe-4-Cl-phenyl | ethyl | Me | CH | N | N | O |
| I-89 | COOH | 3-Me-phenyl | —CH₂—CH₂— | 3-OMe-4-Cl-phenyl | OMe | CH₂—CH₂—CH₂—C | N | N | N | O |
| I-90 | COOH | phenyl | —CH₂—CH₂— | 2-Me-phenyl | Me | Me | CH | N | N | O |
| I-91 | COOH | phenyl | —CH₂—CH₂—CH₂— | 2-Me-phenyl | Me | Me | N | N | N | O |
| I-92 | COOH | phenyl | —CH₂—CH₂— | 4-OEt-3-OMe-phenyl | OMe | O—CH₂—CH₂—C | N | N | N | S |
| I-93 | COOMe | phenyl | —CH₂—CH₂— | 4-iPr-phenyl | CF₃ | Me | CH | N | N | O |
| I-94 | COOH | 2-Me-phenyl | —CH₂—CH₂— | 4-F-phenyl | OMe | Me | CH | N | N | O |
| I-95 | COOH | phenyl | —CH═CH—CH₂— | 4-Me-phenyl | OMe | Me | CH | N | N | O |
| I-96 | COOH | phenyl | —CH═CH—CH₂— | 4-Me-phenyl | Me | Me | CH | N | N | O |
| I-97 | COOH | 2-Me-phenyl | —CH₂—CH₂— | 4-iPr-phenyl | Me | Me | CH | N | N | O |

TABLE I-continued

I

| No. | R¹ | R⁴, R⁵ | Q | R⁶ | R² | R³ | Z | X | Y | W |
|---|---|---|---|---|---|---|---|---|---|---|
| I-98 | COOH | phenyl | —O—CH₂—CH₂— | phenyl | Me | Me | N | N | N | O |
| I-99 | COOH | 4-Et-phenyl | —CH₂—CH₂— | 3,4-di-OMe-phenyl | Me | Me | CH | N | N | O |
| I-100 | COOH | 4-Et-phenyl | —CH₂—CH₂— | 3,4-di-OMe-phenyl | Me | Me | N | N | N | O |
| I-101 | COOH | phenyl | —CH₂—CH₂— | 4-(di-Me-amino)-phenyl | Me | Me | N | N | N | O |
| I-102 | COOH | phenyl | —CH₂—CH₂— | 4-(di-Me-amino)-phenyl | ethyl | Me | CH | N | N | O |
| I-103 | COOH | 2-Me-phenyl | —CH₂—CH₂— | 4-Cl-phenyl | ethyl | Me | CH | N | N | O |
| I-104 | COOH | 4-F-phenyl | —CH₂—CH₂— | 4-OMe-phenyl | OMe | CH₂—CH₂—CH₂—C | N | N | N | O |
| I-105 | COOH | phenyl | —C(CH₃)₂—CH₂— | 3-Cl-phenyl | OMe | O—CH₂—CH₂—C | N | N | N | O |
| I-106 | COOH | phenyl | —CH₂—CH₂—CH₂— | 2-Me-phenyl | CF₃ | Me | CH | N | N | O |
| I-107 | COOH | phenyl | —CH₂—CH₂—CH₂— | 2-Me-phenyl | OMe | Me | CH | N | N | O |
| I-108 | COOH | phenyl | —CH₂—CH₂— | 3,4-methylenedioxyphenyl | Me | Me | N | N | CH | O |
| I-109 | COOMe | phenyl | —CH₂—CH₂— | 3,4-methylenedioxyphenyl | OMe | Me | CH | N | N | O |
| I-110 | COOH | phenyl | —CH₂—CH₂— | 3,4-methylenedioxyphenyl | Me | Me | CH | N | N | S |
| I-111 | COOH | phenyl | —CH=CH—CH₂— | 4-iPr-phenyl | OMe | O—CH₂—CH₂—C | N | N | N | O |
| I-112 | COOH | phenyl | —CH=CH—CH₂— | 4-Me-phenyl | CF₃ | Me | CH | N | N | O |
| I-113 | COOH | phenyl | —CH₂—CH₂— | 3,4-di-Me-phenyl | Me | Me | CH | N | N | O |
| I-114 | COOH | phenyl | —O—CH₂—CH₂— | 3,4-di-Me-phenyl | ethyl | Me | CH | N | N | O |
| I-115 | COOH | 4-Et-phenyl | —CH₂—CH₂— | 4-OMe-phenyl | OMe | O—CH₂—CH₂—C | N | N | N | O |
| I-116 | COOH | 4-Et-phenyl | —CH₂—CH₂— | 3,4-di-OMe-phenyl | OMe | Me | CH | N | N | O |
| I-117 | COO-i-Propyl | phenyl | —CH₂—CH₂— | 3,4-methylenedioxyphenyl | OMe | CH₂—CH₂—CH₂—C | N | N | N | O |
| I-118 | COOH | phenyl | —CH₂—CH₂— | 3,4-di-Me-phenyl | OMe | O—CH₂—CH₂—C | N | N | N | O |
| I-119 | COOH | phenyl | —CH₂—CH₂— | 4-(di-Me-amino)-phenyl | OMe | Me | CH | N | N | O |
| I-120 | COOH | phenyl | —CH₂—CH₂— | 4-(di-Me-amino)-phenyl | Me | Me | CH | N | N | O |
| I-121 | COOH | 4-F-phenyl | —CH₂—CH₂— | 4-Me-phenyl | CF₃ | Me | CH | N | N | O |
| I-122 | COOH | phenyl | —CH₂—CH₂—CH₂— | 3-OMe-phenyl | ethyl | Me | CH | N | N | O |
| I-123 | COOH | phenyl | —CH₂—CH₂—CH₂— | 3-OMe-phenyl | OMe | O—CH₂—CH₂—C | N | N | N | O |
| I-124 | COOH | phenyl | —S—CH₂—CH₂— | 4-Me-phenyl | OMe | Me | CH | N | N | O |
| I-125 | COOH | phenyl | —CH(OH)—CH₂— | 4-Me-phenyl | Me | Me | CH | N | N | O |
| I-126 | COOH | phenyl | —CH₂—CH₂— | 3-OMe-4-Me-phenyl | Me | Me | CH | N | N | O |
| I-127 | COOH | phenyl | —CH=CH—CH₂— | 4-iPr-phenyl | ethyl | Me | CH | N | N | O |
| I-128 | COOH | phenyl | —CH=CH—CH₂— | 4-iPr-phenyl | OMe | Me | CH | N | N | O |
| I-129 | COOH | phenyl | —CH₂—CH₂— | 4-Me-phenyl | ethyl | Me | N | N | CH | O |
| I-130 | COOH | phenyl | —CH₂—CH₂— | 3-OMe-4-Me-phenyl | OMe | CH₂—CH₂—CH₂—C | N | N | N | O |
| I-131 | COOH | 4-Et-phenyl | —CH₂—CH₂— | 4-OMe-phenyl | Me | Me | N | N | N | O |
| I-132 | COOH | 4-Et-phenyl | —CH₂—CH₂— | 4-OMe-phenyl | ethyl | Me | CH | N | N | O |
| I-133 | COOH | phenyl | —CH₂—CH₂— | 4-Me-phenyl | OMe | O—CH₂—CH₂—C | N | N | N | S |
| I-134 | COOButyl | phenyl | —CH₂—CH₂— | 4-Et-phenyl | CF₃ | Me | CH | N | N | O |
| I-135 | COOH | 4-I-phenyl | —CH₂—CH₂— | 4-Et-phenyl | OMe | Me | CH | N | N | O |
| I-136 | COOH | phenyl | —CH(OH)—CH₂— | 4-Et-phenyl | Me | Me | CH | N | N | O |
| I-137 | COOH | phenyl | —CH₂—CH₂— | 2-OMe-phenyl | OMe | CH₂—CH₂—CH₂—C | N | N | N | O |
| I-138 | COOH | phenyl | —CH₂—CH₂—CH₂— | 3-OMe-phenyl | Me | Me | CH | N | N | O |
| I-139 | COOH | phenyl | —CH₂—CH₂—CH₂— | 3-OMe-phenyl | Me | Me | N | N | N | O |
| I-140 | COOH | phenyl | —CH₂—CH₂— | 2-OMe-phenyl | OMe | O—CH₂—CH₂—C | N | N | N | O |
| I-141 | COOH | phenyl | —CH₂—CH₂— | 3-OMe-4-Et-phenyl | Me | Me | N | N | N | O |
| I-142 | COOH | phenyl | —CH₂—CH₂— | 4-Et-phenyl | ethyl | Me | N | N | N | O |
| I-143 | COOH | phenyl | —CH=CH—CH₂— | 4-Cl-phenyl | ethyl | Me | CH | N | N | O |
| I-144 | COOH | phenyl | —CH=CH—CH₂— | 4-Cl-phenyl | OMe | CH₂—CH₂—CH₂—C | N | N | N | O |
| I-145 | COOH | phenyl | —CH₂—CH₂— | 4-OEt-3-OMe-phenyl | OMe | Me | CH | N | N | O |
| I-146 | COOH | phenyl | —CH₂—CH₂— | 4-OEt-3-OMe-phenyl | Me | Me | CH | N | N | O |
| I-147 | COOH | 4-Et-phenyl | —CH₂—CH₂— | 4-OMe-phenyl | OMe | Me | CH | N | N | O |
| I-148 | COOH | 4-Et-phenyl | —CH₂—CH₂— | 4-OMe-phenyl | Me | Me | CH | N | N | O |
| I-149 | COOH | phenyl | —CH₂—CH₂— | 3-OMe-4-Et-phenyl | OMe | O—CH=CH—C | N | N | N | O |
| I-150 | COOH | phenyl | —CH₂—CH₂— | 3-OMe-4-Et-phenyl | OMe | O—CH₂—CH₂—C | N | N | N | O |
| I-151 | COOH | 4-Me-phenyl | —CH₂—CH₂— | cyclohexyl | CF₃ | Me | CH | N | N | O |
| I-152 | COOH | phenyl | —CH₂—CH₂— | cyclohexyl | OMe | ethyl | CH | N | N | O |
| I-153 | COOMe | phenyl | —CH₂—CH₂— | cyclohexyl | OMe | Me | CH | N | N | O |
| I-154 | COOH | phenyl | —CH₂—CH₂—CH₂— | 3-OMe-phenyl | CF₃ | Me | CH | N | N | O |
| I-155 | COOH | phenyl | —CH₂—CH₂—CH₂— | 3-OMe-phenyl | OMe | Me | CH | N | N | O |
| I-156 | COOH | phenyl | —CH₂—CH₂— | cyclohexyl | Me | Me | CH | N | CH | O |
| I-157 | COOH | phenyl | —CH₂—CH₂— | cyclohexyl | Me | Me | N | N | CH | O |
| I-158 | COOH | 4-Cl-phenyl | —CH₂—CH₂— | cyclohexyl | ethyl | Me | CH | N | N | O |
| I-159 | COOH | phenyl | —CH=CH—CH₂— | 4-Cl-phenyl | Me | Me | CH | N | N | O |
| I-160 | COOH | phenyl | —CH=CH—CH₂— | 4-Cl-phenyl | Me | Me | N | N | N | O |
| I-161 | COOH | phenyl | —CH₂—CH₂— | 2-OMe-phenyl | Me | Me | N | N | N | O |
| I-162 | COOH | phenyl | —CH₂—CH₂— | 2-OMe-phenyl | ethyl | Me | CH | N | N | O |

TABLE I-continued

[sic]

$$R^6-Q-W-\underset{R^5}{\overset{R^4}{C}}-\underset{R^1}{\overset{}{CH}}-O-\text{ring}(R^2, R^3, X, Y, Z)$$

I

| No. | R¹ | R⁴, R⁵ | Q | R⁶ | R² | R³ | Z | X | Y | W |
|---|---|---|---|---|---|---|---|---|---|---|
| I-163 | COOH | 4-Cl-phenyl | —CH₂—CH₂— | 2-OMe-phenyl | ethyl | Me | CH | N | N | O |
| I-164 | COOH | 4-Cl-phenyl | —CH₂—CH₂— | 2-OMe-phenyl | OMe | O—CH₂—CH₂—C | N | N | O |
| I-165 | COOH | 4-Et-phenyl | —CH₂—CH₂— | cyclohexyl | OMe | CH₂—CH₂—CH₂—C | N | N | O |
| I-166 | COOH | phenyl | —CH₂—CH₂— | cyclohexyl | OMe | O—CH₂—CH₂—C | N | N | S |
| I-167 | COOH | phenyl | —CH₂—CH₂— | 4-SMe-phenyl | OMe | O—CH₂—CH₂—C | N | N | O |
| I-168 | COOH | phenyl | —CH₂—CH₂— | 4-OEt-3-OMe-phenyl | CF₃ | Me | CH | N | N | O |
| I-169 | COOH | phenyl | —CH₂—CH₂— | 3-Me-4-Cl-phenyl | CF₃ | Me | CH | N | N | O |
| I-170 | COOH | phenyl | —CH₂—CH₂—CH₂— | 4-OEt-phenyl | ethyl | Me | CH | N | N | O |
| I-171 | COOH | phenyl | —CH₂—CH₂—CH₂— | 4-OEt-phenyl | OMe | CH₂—CH₂—CH₂—C | N | N | O |
| I-172 | COOH | phenyl | —CH₂—CH₂— | 4-Cl-phenyl | OMe | Me | CH | N | N | S |
| I-173 | COOH | 3-Me-phenyl | —CH₂—CH₂— | 4-Cl-phenyl | Me | Me | CH | N | N | O |
| I-174 | COOH | phenyl | —O—CH₂—CH₂— | 4-Cl-phenyl | ethyl | Me | N | N | N | O |
| I-175 | COOH | phenyl | —CH=CH—CH₂— | 4-Cl-phenyl | CF₃ | Me | CH | N | N | O |
| I-176 | COOH | phenyl | —CH=CH—CH₂— | 4-Cl-phenyl | OMe | Me | CH | N | N | O |
| I-177 | COOH | phenyl | —CH₂—CH₂— | 2-Me-4-Cl-phenyl | SMe | Me | CH | N | N | O |
| I-178 | COOH | phenyl | —CH₂—CH₂— | cyclohexyl | OMe | CH₂—CH₂—CH₂—C | N | N | O |
| I-179 | COOH | 4-CF₃-phenyl | —CH₂—CH₂— | 3-OMe-phenyl | Me | Me | CH | N | N | O |
| I-180 | COOH | 4-CF₃-phenyl | —CH₂—CH₂— | 3-OMe-phenyl | Me | Me | N | N | N | O |
| I-181 | COOH | phenyl | —CH₂—CH₂— | cyclohexyl | OMe | O—CH₂—CH₂—C | N | N | O |
| I-182 | COOBzl | phenyl | —CH₂—CH₂— | 4-Cl-phenyl | OMe | CH₂—CH₂—CH₂—C | N | N | O |
| I-183 | COOH | phenyl | —CH₂—CH₂— | 2-Me-4-Cl-phenyl | OMe | O—CH₂—CH₂—C | N | N | O |
| I-184 | COOH | phenyl | —CH(OH)—CH₂— | naphth-2-yl | CF₃ | Me | CH | N | N | O |
| I-185 | COOH | phenyl | —CH₂—CH₂— | 2-OMe-phenyl | OMe | Me | CH | N | N | O |
| I-186 | COOH | phenyl | —CH₂—CH₂—CH₂— | 4-OEt-phenyl | Me | Me | CH | N | N | O |
| I-187 | COOH | phenyl | —CH₂—CH₂—CH₂— | 4-OEt-phenyl | Me | Me | N | N | N | O |
| I-188 | COOH | phenyl | —CH₂—CH₂— | 2-OMe-phenyl | Me | Me | CH | N | N | O |
| I-189 | COOH | 2-Me-phenyl | —CH₂—CH₂— | naphth-2-yl | OMe | Me | CH | N | N | O |
| I-190 | COOH | phenyl | —CH₂—CH₂— | naphth-2-yl | Me | Me | CH | N | N | S |
| I-191 | COOH | phenyl | —CH=CH—CH₂— | 4-Cl-phenyl | OMe | O—CH₂—CH₂—C | N | N | O |
| I-192 | COOH | phenyl | —CH=CH—CH₂— | 4-iPr-phenyl | Me | Me | CH | N | N | O |
| I-193 | COOH | phenyl | —CH₂—CH₂— | 4-SMe-phenyl | ethyl | Me | CH | N | N | O |
| I-194 | COOH | phenyl | —CH₂—CH₂— | 4-SMe-phenyl | OMe | CH₂—CH₂—CH₂—C | N | N | O |
| I-195 | COOH | 4-CF₃-phenyl | —CH₂—CH₂— | 3,4-di-OMe-phenyl | OMe | O—CH₂—CH₂—C | N | N | O |
| I-196 | COOH | 4-CF₃-phenyl | —CH₂—CH₂— | 3-OMe-phenyl | OMe | Me | CH | N | N | O |
| I-197 | COOH | phenyl | —CH₂—CH₂— | naphth-2-yl | Me | Me | N | N | CH | O |
| I-198 | COOH | phenyl | —CH₂—CH₂— | 1-Me-naphth-2-yl | ethyl | Me | CH | N | N | O |
| I-199 | COOH | phenyl | —CH₂—CH₂— | 1-Me-naphth-2-yl | OMe | CH₂—CH₂—CH₂—C | N | N | O |
| I-200 | COOMe | phenyl | —CH₂—CH₂— | naphth-2-yl | OMe | O—CH₂—CH₂—C | N | N | O |
| I-201 | COOEt | phenyl | —CH₂—CH₂— | 4-OEt-phenyl | CF₃ | Me | CH | N | N | O |
| I-202 | COOH | phenyl | —CH₂—CH₂—CH₂— | 4-OEt-phenyl | CF₃ | Me | CH | N | N | O |
| I-203 | COOH | phenyl | —CH₂—CH₂—CH₂— | 4-OEt-phenyl | OMe | Me | CH | N | N | O |
| I-204 | COOH | phenyl | —CH₂—CH₂— | cyclohexyl | Me | Me | N | N | N | O |
| I-205 | COOH | phenyl | —CH₂—CH₂— | cyclohexyl | ethyl | Me | CH | N | N | O |
| I-206 | tetrazole [sic] | phenyl | —CH₂—CH₂— | 4-OEt-phenyl | OMe | Me | CH | N | N | O |
| I-207 | COOH | phenyl | —CH=CH—CH₂— | 3,4-di-OMe-phenyl | ethyl | Me | CH | N | N | O |
| I-208 | COOH | phenyl | —CH=CH—CH₂— | 3,4-di-OMe-phenyl | OMe | O—CH₂—CH₂—C | N | N | O |
| I-209 | COOH | phenyl | —CH₂—CH₂— | 4-OH-phenyl | Me | Me | CH | N | N | O |
| I-210 | COOH | phenyl | —CH₂—CH₂— | 4-OH-phenyl | ethyl | Me | N | N | CH | O |
| I-211 | COOH | 4-CF₃-phenyl | —CH₂—CH₂— | 3,4-di-OMe-phenyl | Me | Me | N | N | N | O |
| I-212 | COOH | 4-CF₃-phenyl | —CH₂—CH₂— | 3,4-di-OMe-phenyl | ethyl | Me | CH | N | N | O |
| I-213 | COOH | phenyl | —CH₂—CH₂— | 3-OMe-phenyl | OMe | O—CH₂—CH₂—C | N | N | O |
| I-214 | COOH | phenyl | —CH₂—CH₂— | 2-OMe-phenyl | CF₃ | Me | CH | N | N | O |
| I-215 | COOH | phenyl | —CH₂—CH₂— | 4-OEt-phenyl | ethyl | Me | CH | N | N | S |
| I-216 | COOH | phenyl | —C(CH₃)₂—CH₂— | 4-OEt-phenyl | OMe | CH₂—CH₂—CH₂—C | N | N | O |
| I-217 | COOH | phenyl | —CH₂—CH₂— | 4-SMe-phenyl | Me | Me | CH | N | N | O |
| I-218 | COOH | phenyl | —CH₂—CH₂—CH₂— | 4-Cl-phenyl | OMe | CH₂—CH₂—CH₂—C | N | N | O |
| I-219 | COOH | phenyl | —CH₂—CH₂—CH₂— | 4-Cl-phenyl | OMe | O—CH₂—CH₂—C | N | N | O |
| I-220 | COOH | phenyl | —CH₂—CH₂— | 4-SMe-phenyl | Me | Me | N | N | N | O |
| I-221 | COOH | phenyl | —O—CH₂—CH₂— | 4-OEt-phenyl | OMe | O—CH₂—CH₂—C | N | N | O |
| I-222 | COOH | 4-Br-phenyl | —CH₂—CH₂— | 3,5-di-OMe-phenyl | CF₃ | Me | N | N | CH | O |
| I-223 | COOH | phenyl | —CH=CH—CH₂— | 3,4-di-OMe-phenyl | Me | Me | CH | N | N | O |
| I-224 | COOH | phenyl | —CH=CH—CH₂— | 3,4-di-OMe-phenyl | Me | Me | N | N | N | O |
| I-225 | COOH | 4-I-phenyl | —CH₂—CH₂— | 3,5-di-OMe-phenyl | OMe | Me | CH | N | N | O |
| I-226 | COOH | phenyl | —CH₂—CH₂— | 3,5-di-OMe-phenyl | Me | Me | CH | N | CH | O |
| I-227 | COOH | 4-CF₃-phenyl | —CH₂—CH₂— | 3,4-di-OMe-phenyl | OMe | Me | CH | N | N | O |

TABLE I-continued

I

| No. | R¹ | R⁴, R⁵ | Q | R⁶ | R² | R³ | Z | X | Y | W |
|---|---|---|---|---|---|---|---|---|---|---|
| I-228 | COOH | 4-CF₃-phenyl | —CH₂—CH₂— | 3,4-di-OMe-phenyl | Me | Me | CH | N | N | O |
| I-229 | COOH | phenyl | —CH₂—CH₂— | 3,5-di-OMe-phenyl | ethyl | Me | N | N | N | O |
| I-230 | COOH | phenyl | —CH₂—CH₂— | cyclohexyl | OMe | Me | CH | N | N | O |
| I-231 | COOH | phenyl | —CH₂—CH₂— | cyclohexyl | Me | Me | CH | N | N | O |
| I-232 | COOH | phenyl | —CH(OH)—CH₂— | 3,5-di-OMe-phenyl | ethyl | Me | CH | N | N | O |
| I-233 | COOH | phenyl | —CH₂—CH₂— | 3,5-di-OMe-4-Cl-phenyl | OMe | CH₂—CH₂—CH₂—C | N | N | N | O |
| I-234 | COOH | phenyl | —CH₂—CH₂—CH₂— | 4-Cl-phenyl | Me | Me | N | N | N | O |
| I-235 | COOH | phenyl | —CH₂—CH₂—CH₂— | 4-Cl-phenyl | ethyl | Me | CH | N | N | O |
| I-236 | COOMe | phenyl | —CH₂—CH₂— | 3,5-di-OMe-phenyl | OMe | O—CH₂—CH₂—C | N | N | N | O |
| I-237 | COOH | phenyl | —CH₂—CH₂— | 3-OMe-phenyl | ethyl | Me | CH | N | N | O |
| I-238 | COOH | phenyl | —CH₂—CH₂— | 3-OMe-phenyl | OMe | CH₂—CH₂—CH₂—C | N | N | N | O |
| I-239 | COOH | phenyl | —CH=CH—CH₂— | 3,4-di-OMe-phenyl | CF₃ | Me | CH | N | N | O |
| I-240 | COOH | phenyl | —CH=CH—CH₂— | 3,4-di-OMe-phenyl | OMe | Me | CH | N | N | O |
| I-241 | COOH | phenyl | —CH₂—CH₂— | 2-Me-3-OMe-phenyl | CF₃ | Me | CH | N | N | O |
| I-242 | COOH | phenyl | —CH₂—CH₂— | 3-OMe-phenyl | OMe | Me | N | N | N | O |
| I-243 | COOH | 4-CF₃-phenyl | —CH₂—CH₂— | 4-OMe-phenyl | ethyl | Me | CH | N | N | O |
| I-244 | COOH | 4-CF₃-phenyl | —CH₂—CH₂— | 4-OMe-phenyl | OMe | O—CH₂—CH₂—C | N | N | N | O |
| I-245 | COOH | phenyl | —CH₂—CH₂— | 4-SMe-phenyl | OMe | OMe | CH | N | N | O |
| I-246 | COOH | phenyl | —CH₂—CH₂— | 4-SMe-phenyl | OMe | Me | CH | N | N | O |
| I-247 | COOH | phenyl | —CH₂—CH₂— | 3-OMe-phenyl | Me | Me | CH | N | CH | O |
| I-248 | COOH | phenyl | —CH₂—CH₂— | 3-OMe-phenyl | Me | Me | N | N | CH | O |
| I-249 | COOH | phenyl | —CH₂—CH₂— | 3-OMe-phenyl | ethyl | Me | CH | N | N | S |
| I-250 | COOH | phenyl | —CH₂—CH₂—CH₂— | 4-Cl-phenyl | OMe | Me | CH | N | N | O |
| I-251 | COOH | phenyl | —CH₂—CH₂—CH₂— | 4-Cl-phenyl | Me | Me | CH | N | N | O |
| I-252 | COOH | 4-F-phenyl | —CH₂—CH₂— | 3-OMe-phenyl | OMe | CH₂—CH₂—CH₂—C | N | N | N | O |
| I-253 | COOH | phenyl | —CH₂—CH(CH₃)— | 3-OMe-phenyl | OMe | O—CH₂—CH₂—C | N | N | N | O |
| I-254 | COOH | phenyl | —CH₂—CH₂— | cyclohexyl | CF₃ | Me | CH | N | N | O |
| I-255 | COOH | phenyl | —CH=CH—CH₂— | 4-OMe-phenyl | OMe | CH₂—CH₂—CH₂—C | N | N | N | O |
| I-256 | COOH | phenyl | —CH=CH—CH₂— | 4-OMe-phenyl | OMe | O—CH₂—CH₂—C | N | N | N | O |
| I-257 | COOH | phenyl | —CH₂—CH₂— | cyclohexyl | OMe | OMe | CH | N | N | O |
| I-258 | tetrazole [sic] | phenyl | —CH₂—CH₂— | 2-OMe-phenyl | CF₃ | Me | CH | N | N | O |
| I-259 | COOH | 4-CF₃-phenyl | —CH₂—CH₂— | 4-OMe-phenyl | Me | Me | CH | N | N | O |
| I-260 | COOH | 4-CF₃-phenyl | —CH₂—CH₂— | 4-OMe-phenyl | Me | Me | N | N | N | O |
| I-261 | COOH | phenyl | —CH(2-OMe-phenyl)-CH₂— | 2-OMe-phenyl | OMe | Me | CH | N | N | O |
| I-262 | COOH | phenyl | —CH₂—CH₂— | 2-OMe-4-Br-phenyl | Me | Me | CH | N | N | O |
| I-263 | COOH | phenyl | —CH₂—CH₂— | 3-OMe-phenyl | Me | Me | CH | N | N | O |
| I-264 | COOH | phenyl | —CH₂—CH₂— | 3-OMe-phenyl | Me | Me | N | N | N | O |
| I-265 | COOH | phenyl | —CH₂—CH₂— | 2-OMe-phenyl | Me | Me | N | N | CH | O |
| I-266 | COOH | phenyl | —CH₂—CH₂—CH₂— | 4-Et-phenyl | OMe | O—CH₂—CH₂—C | N | N | N | O |
| I-267 | COOH | phenyl | —CH₂—CH₂—CH₂— | 4-Cl-phenyl | CF₃ | Me | CH | N | N | O |
| I-268 | COOH | phenyl | —CH₂—CH₂— | 2-OMe-phenyl | ethyl | Me | CH | N | N | S |
| I-269 | COOH | phenyl | —CH₂—CH₂— | 3,4,5-tri-OMe-phenyl | OMe | O—CH₂—CH₂—C | N | N | N | O |
| I-270 | COOH | phenyl | —CH₂—CH₂— | 4-SMe-phenyl | CF₃ | Me | CH | N | N | O |
| I-271 | COOH | phenyl | —CH=CH—CH₂— | 4-OMe-phenyl | Me | Me | N | N | N | O |
| I-272 | COOH | phenyl | —CH=CH—CH₂— | 4-OMe-phenyl | ethyl | Me | CH | N | N | O |
| I-273 | COOH | 4-Br-phenyl | —CH₂—CH₂— | 2-OMe-phenyl | OMe | CH₂—CH₂—CH₂—C | N | N | N | O |
| I-274 | COOH | phenyl | —CH(OH)—CH₂— | 2-OMe-phenyl | OMe | O—CH₂—CH₂—C | N | N | N | O |
| I-275 | COOH | 4-Et-phenyl | —CH₂—CH₂— | 4-Me-phenyl | OMe | O—CH₂—CH₂—C | N | N | N | O |
| I-276 | COOH | 4-CF₃-phenyl | —CH₂—CH₂— | 4-OMe-phenyl | OMe | Me | CH | N | N | O |
| I-277 | COOH | 4-Cl-phenyl | —CH(4-OMe-phenyl)—CH₂— | 4-OMe-phenyl | OMe | Me | CH | N | N | O |
| I-278 | COOH | 4-Cl-phenyl | —CH₂—CH₂— | 3-Me-4-OMe-phenyl | Me | Me | CH | N | N | O |
| I-279 | COOH | 4-Cl-phenyl | —CH₂—CH₂— | 3,4-methylenedioxyphenyl | Me | Me | CH | N | N | O |
| I-280 | COOH | 4-Cl-phenyl | —CH₂—CH₂— | 3,4-methylenedioxyphenyl | Me | Me | N | N | N | O |
| I-281 | COOH | 4-Cl-phenyl | —CH₂—CH₂— | 4-OMe-phenyl | ethyl | Me | N | N | N | O |
| I-282 | COOH | phenyl | —CH₂—CH₂—CH₂— | 4-Et-phenyl | ethyl | Me | CH | N | N | O |
| I-283 | COOH | phenyl | —CH₂—CH₂—CH₂— | 4-Et-phenyl | OMe | CH₂—CH₂—CH₂—C | N | N | N | O |
| I-284 | COOH | phenyl | —CH₂—CH₂— | 4-Et-phenyl | OMe | CH₂—CH₂—CH₂—C | N | N | N | O |
| I-285 | COOH | phenyl | —CH₂—CH₂— | 4-Et-phenyl | OMe | O—CH₂—CH₂—C | N | N | N | O |
| I-286 | COOH | 4-Cl-phenyl | —CH₂—CH₂— | 4-OMe-phenyl | ethyl | Me | CH | N | N | S |
| I-287 | COOH | phenyl | —CH=CH—CH₂— | 4-OMe-phenyl | OMe | Me | CH | N | N | O |
| I-288 | COOH | phenyl | —CH=CH—CH₂— | 4-OMe-phenyl | Me | Me | CH | N | N | O |
| I-289 | COOH | 3,4-di-Cl-phenyl | —CH₂—CH₂— | 4-OMe-phenyl | OMe | O—CH₂—CH₂—C | N | N | N | O |
| I-290 | COOEt | 4-Cl-phenyl | —CH(OH)—CH₂— | 3,4-di-OMe-phenyl | OMe | Me | CH | N | N | O |
| I-291 | COOH | 4-Et-phenyl | —CH₂—CH₂— | 4-Me-phenyl | Me | Me | N | N | N | O |
| I-292 | COOH | 4-Et-phenyl | —CH₂—CH₂— | 4-Me-phenyl | ethyl | Me | CH | N | N | O |

TABLE I-continued

[sic]

I $$R^6-Q-W-\underset{R^5}{\overset{R^4}{C}}-\underset{R^1}{CH}-O-\text{pyrimidine ring with }R^2, R^3, X, Y, Z$$

| No. | $R^1$ | $R^4, R^5$ | Q | $R^6$ | $R^2$ | $R^3$ | Z | X | Y | W |
|---|---|---|---|---|---|---|---|---|---|---|
| I-293 | COOH | phenyl | —CH$_2$—CH$_2$— | 3-OMe-phenyl | CF$_3$ | Me | CH | N | N | O |
| I-294 | COOH | phenyl | —CH$_2$—CH$_2$— | 3-OMe-phenyl | OMe | Me | CH | N | N | O |
| I-295 | COOH | 4-Cl-phenyl | —CH$_2$—CH$_2$— | 3,4-di-OMe-phenyl | Me | Me | CH | N | CH | O |
| I-296 | COOH | 4-Cl-phenyl | —C(CH$_3$)$_2$—CH$_2$— | 3,4-di-OMe-phenyl | Me | Me | N | N | N | O |
| I-297 | COOH | phenyl | —CH$_2$—CH$_2$— | 3,4,5-tri-OMe-phenyl | ethyl | Me | CH | N | N | O |
| I-298 | COOH | phenyl | —CH$_2$—CH$_2$—CH$_2$— | 4-Et-phenyl | Me | Me | CH | N | N | O |
| I-299 | COOH | phenyl | —CH$_2$—CH$_2$—CH$_2$— | 4-Et-phenyl | Me | Me | N | N | N | O |
| I-300 | COOH | phenyl | —CH$_2$—CH$_2$— | 3,4,5-tri-OMe-phenyl | OMe | CH$_2$—CH$_2$—CH$_2$—C | N | N | N | O |
| I-301 | COOH | 4-Cl-phenyl | —CH$_2$—CH$_2$— | 3,4-di-OMe-phenyl | ethyl | Me | N | N | N | O |
| I-302 | COOH | 3,4-di-Cl-phenyl | —CH$_2$—CH$_2$— | 3,4-di-OMe-phenyl | OMe | O—CH$_2$—CH$_2$—C | N | N | N | O |
| I-303 | COOH | phenyl | —CH$_2$—CH$_2$—CH$_2$— | 3,4,5-tri-OMe-phenyl | OMe | CH$_2$—CH$_2$—CH$_2$—C | N | N | N | O |
| I-304 | COOH | phenyl | —CH=CH—CH$_2$— | 4-OMe-phenyl | CF$_3$ | Me | CH | N | N | O |
| I-305 | COOH | 4-Cl-phenyl | —CH$_2$—CH$_2$— | 3-Me-4-Et-phenyl | OMe | Me | CH | N | N | O |
| I-306 | COOH | 4-Cl-phenyl | —CH$_2$—CH$_2$— | 3-Me-4-Et-phenyl | SMe | Me | CH | N | N | O |
| I-307 | COOH | 4-Et-phenyl | —CH$_2$—CH$_2$— | 4-Me-phenyl | OMe | Me | CH | N | N | O |
| I-308 | COOH | 4-Et-phenyl | —CH$_2$—CH$_2$— | 4-Me-phenyl | Me | Me | CH | N | N | O |
| I-309 | COOH | 4-Cl-phenyl | —CH$_2$—CH$_2$— | 4-iPr-phenyl | OMe | O—CH$_2$—CH$_2$—C | N | N | N | O |
| I-310 | COOH | 4-Cl-phenyl | —CH$_2$—CH$_2$— | 3,4-methylenedioxyphenyl | OMe | Me | CH | N | N | O |
| I-311 | COOH | 4-Cl-phenyl | —CH$_2$—CH$_2$— | 4-Br-phenyl | Me | Me | N | N | N | O |
| I-312 | COOH | phenyl | —CH$_2$—CH$_2$— | 4-Et-phenyl | Me | Me | N | N | N | O |
| I-313 | COOH | phenyl | —CH$_2$—CH$_2$— | 4-Et-phenyl | ethyl | Me | CH | N | N | O |
| I-314 | COOH | phenyl | —CH$_2$—CH$_2$—CH$_2$— | 4-Et-phenyl | CF$_3$ | Me | CH | N | N | O |
| I-315 | COOH | phenyl | —CH$_2$—CH$_2$—CH$_2$— | 4-Et-phenyl | OMe | Me | CH | N | N | O |
| I-316 | COOH | 4-Cl-phenyl | —CH$_2$—CH$_2$— | 4-Br-phenyl | ethyl | Me | CH | N | N | O |
| I-317 | COOH | 4-Cl-phenyl | —CH(4-Br-phenyl)—CH$_2$— | 4-Br-phenyl | OMe | O—CH$_2$—CH$_2$—C | N | N | N | O |
| I-318 | COOH | 4-Cl-phenyl | —CH(OH)—CH$_2$— | 4-SMe-phenyl | OMe | Me | CH | N | N | O |
| I-319 | COOH | phenyl | —CH$_2$—CH$_2$—CH$_2$— | 3,4,5-tri-OMe-phenyl | Me | Me | N | N | N | O |
| I-320 | COOH | phenyl | —CH$_2$—CH$_2$—CH$_2$— | 3,4,5-tri-OMe-phenyl | ethyl | Me | CH | N | N | O |
| I-321 | COOH | phenyl | —CH$_2$—CH$_2$— | 3,5-di-OMe-phenyl | OMe | CH$_2$—CH$_2$—CH$_2$—C | N | N | N | O |
| I-322 | COOH | phenyl | —CH$_2$—CH$_2$— | 3,5-di-OMe-phenyl | OMe | O—CH$_2$—CH$_2$—C | N | N | N | O |
| I-323 | COOH | 4-Et-phenyl | —CH$_2$—CH$_2$— | 4-SMe-phenyl | ethyl | Me | CH | N | N | O |
| I-324 | COOH | 4-Et-phenyl | —CH$_2$—CH$_2$— | 4-SMe-phenyl | OMe | O—CH$_2$—CH$_2$—C | N | N | N | O |
| I-325 | COOH | 4-Cl-phenyl | —C(CH$_3$)$_2$—CH$_2$— | 4-SMe-phenyl | Me | Me | CH | N | CH | O |
| I-326 | COOH | 4-Cl-phenyl | —CH$_2$—CH$_2$— | 4-SMe-phenyl | Me | Me | N | N | N | S |
| I-327 | COOH | phenyl | —CH$_2$—CH$_2$— | 3,4,5-tri-OMe-phenyl | Me | Me | CH | N | N | O |
| I-328 | COOH | phenyl | —CH$_2$—CH$_2$— | 3,4,5-tri-OMe-phenyl | Me | Me | N | N | N | O |
| I-329 | COOH | 4-Cl-phenyl | —O—CH$_2$—CH$_2$— | 4-SMe-phenyl | ethyl | Me | CH | N | N | O |
| I-330 | COOH | phenyl | —CH$_2$—CH$_2$—CH$_2$— | 4-Me-phenyl | ethyl | Me | CH | N | N | O |
| I-331 | COOH | phenyl | —CH$_2$—CH$_2$—CH$_2$— | 4-Me-phenyl | OMe | O—CH$_2$—CH$_2$—C | N | N | N | O |
| I-332 | COOH | 4-Cl-phenyl | —CH$_2$—CH$_2$— | 4-SMe-phenyl | OMe | O—CH=CH—C | N | N | N | O |
| I-333 | COOH | 4-Cl-phenyl | —CH(OH)—CH$_2$— | 4-OEt-3-OMe-phenyl | OMe | Me | CH | N | N | O |
| I-334 | COOH | 4-Cl-phenyl | —CH(4-SMe-phenyl)—CH$_2$— | 4-SMe-phenyl | Me | Me | CH | N | N | O |
| I-335 | COOH | phenyl | —CH$_2$—CH$_2$—CH$_2$— | 3,4,5-tri-OMe-phenyl | OMe | Me | CH | N | N | O |
| I-336 | COOH | phenyl | —CH$_2$—CH$_2$—CH$_2$— | 3,4,5-tri-OMe-phenyl | Me | Me | CH | N | N | O |
| I-337 | COOH | 4-Cl-phenyl | —CH$_2$—CH$_2$— | 4-iPr-phenyl | Me | Me | N | N | N | O |
| I-338 | COOH | 4-Cl-phenyl | —CH$_2$—CH$_2$— | 4-iPr-phenyl | ethyl | Me | CH | N | N | O |
| I-339 | COOH | 4-Me-phenyl | —CH$_2$—CH$_2$— | 3,4-di-OMe-phenyl | Me | Me | CH | N | N | O |
| I-340 | COOH | 4-Me-phenyl | —CH$_2$—CH$_2$— | 3,4-di-OMe-phenyl | Me | Me | N | N | N | O |
| I-341 | COOH | 3,4-di-Cl-phenyl | —CH$_2$—CH$_2$— | 4-OEt-3-OMe-phenyl | Me | Me | N | N | N | O |
| I-342 | COOH | phenyl | —CH$_2$—CH$_2$— | 4-Et-phenyl | OMe | Me | CH | N | N | O |
| I-343 | COOH | phenyl | —CH$_2$—CH$_2$— | 4-Et-phenyl | Me | Me | CH | N | N | O |
| I-344 | COOH | 4-Cl-phenyl | —CH$_2$—CH$_2$— | 4-OEt-3-OMe-phenyl | ethyl | Me | CH | N | N | S |
| I-345 | COOH | 4-Cl-phenyl | —CH(4-Me-phenyl)—CH$_2$— | 4-Me-phenyl | OMe | Me | CH | N | N | O |
| I-346 | COOH | phenyl | —CH$_2$—CH$_2$—CH$_2$— | 4-Me-phenyl | Me | Me | CH | N | N | O |
| I-347 | COOH | phenyl | —CH$_2$—CH$_2$—CH$_2$— | 4-Me-phenyl | Me | Me | N | N | N | O |
| I-348 | COOMe | 4-Cl-phenyl | —CH$_2$—CH$_2$— | 4-Me-phenyl | Me | Me | CH | N | CH | O |
| I-349 | COOH | phenyl | —CH$_2$—CH$_2$— | 3,5-di-OMe-phenyl | Me | Me | N | N | N | O |
| I-350 | COOH | phenyl | —CH$_2$—CH$_2$— | 3,5-di-OMe-phenyl | ethyl | Me | CH | N | N | O |
| I-351 | COOH | phenyl | —CH$_2$—CH$_2$— | 2-Cl-phenyl | OMe | CH$_2$—CH$_2$—CH$_2$—C | N | N | N | O |
| I-352 | COOH | phenyl | —CH$_2$—CH$_2$—CH$_2$— | 3,4,5-tri-OMe-phenyl | CF$_3$ | Me | CH | N | N | O |
| I-353 | COOH | 4-Cl-phenyl | —CH(OH)—CH$_2$— | 4-Me-phenyl | Me | Me | N | N | N | O |
| I-354 | COOH | 4-Cl-phenyl | —CH$_2$—CH$_2$— | 3,4-di-Me-phenyl | ethyl | Me | CH | N | N | O |
| I-355 | COOH | 4-Me-phenyl | —CH$_2$—CH$_2$— | 4-OMe-phenyl | OMe | O—CH$_2$—CH$_2$—C | N | N | N | O |
| I-356 | COOH | 4-Me-phenyl | —CH$_2$—CH$_2$— | 3,4-di-OMe-phenyl | OMe | Me | CH | N | N | O |
| I-357 | COOH | phenyl | —CH$_2$—CH$_2$— | 3,4,5-tri-OMe-phenyl | OMe | OMe | CH | N | N | O |
| I-358 | COOH | phenyl | —CH$_2$—CH$_2$— | 3,4,5-tri-OMe-phenyl | OMe | Me | CH | N | N | O |

TABLE I-continued

I $$R^6-Q-W-\underset{\underset{R^5}{|}}{\overset{\overset{R^4}{|}}{C}}-\underset{\underset{R^1}{|}}{CH}-O-\text{(ring: Y, Z, X with } R^2, R^3\text{)}$$

| No. | R¹ | R⁴, R⁵ | Q | R⁶ | R² | R³ | Z | X | Y | W |
|---|---|---|---|---|---|---|---|---|---|---|
| I-359 | COOH | 4-Cl-phenyl | —CH₂—CH₂— | 4-Me-phenyl | OMe | O—CH₂—CH₂—C | N | N | S | |
| I-360 | COOH | 4-Cl-phenyl | —CH₂—CH₂— | 4-Et-phenyl | OMe | Me | CH | N | N | S |
| I-361 | COOH | 4-Cl-phenyl | —CH₂—CH₂— | 4-Et-phenyl | Me | Me | CH | N | CH | O |
| I-362 | COOH | phenyl | —CH₂—CH₂—CH₂— | 4-Me-phenyl | CF₃ | Me | CH | N | N | O |
| I-363 | COOH | phenyl | —CH₂—CH₂—CH₂— | 4-Me-phenyl | OMe | Me | CH | N | N | O |
| I-364 | COOH | 4-Cl-phenyl | —CH₂—CH₂— | 4-Et-phenyl | ethyl | Me | N | N | N | O |
| I-365 | COOH | 4-Cl-phenyl | —CH₂—CH₂— | 4-iPr-phenyl | OMe | Me | CH | N | N | O |
| I-366 | COOH | 4-Cl-phenyl | —CH₂—CH₂— | 4-iPr-phenyl | Me | Me | CH | N | N | O |
| I-367 | COOH | phenyl | —CH₂—CH₂—CH₂— | 2-Cl-phenyl | Me | Me | N | N | N | O |
| I-368 | COOH | phenyl | —CH₂—CH₂—CH₂— | 2-Cl-phenyl | ethyl | Me | CH | N | N | O |
| I-369 | COOH | 4-Cl-phenyl | —CH₂—CH₂— | 4-Et-phenyl | SMe | Me | CH | N | N | O |
| I-370 | COOH | phenyl | —CH₂—CH₂— | 4-Me-phenyl | OMe | O—CH₂—CH₂—C | N | N | N | O |
| I-371 | COOH | 4-Me-phenyl | —CH₂—CH₂— | 4-OMe-phenyl | Me | Me | N | N | N | O |
| I-372 | COOH | 4-Me-phenyl | —CH₂—CH₂— | 4-OMe-phenyl | ethyl | Me | CH | N | N | O |
| I-373 | COOH | phenyl | —CH₂—CH₂— | 4-Et-phenyl | CF₃ | Me | CH | N | N | O |
| I-374 | COOH | 4-Cl-phenyl | —C(CH₃)₂—CH₂— | 4-Et-phenyl | OMe | O—CH₂—CH₂—C | N | N | N | O |
| I-375 | COOH | 4-Cl-phenyl | —CH₂—CH₂— | 4-Cl-phenyl | OMe | Me | CH | N | N | S |
| I-376 | COOH | 4-Cl-phenyl | —CH₂—CH₂— | 1-Me-naphth-2-yl | OMe | Me | CH | N | N | O |
| I-377 | COOH | phenyl | —CH₂—CH₂— | 3,5-di-OMe-phenyl | OMe | Me | CH | N | N | O |
| I-378 | COOH | phenyl | —CH₂—CH₂—CH₂— | 3,4-methylenedioxyphenyl | ethyl | Me | CH | N | N | O |
| I-379 | COOH | phenyl | —CH₂—CH₂—CH₂— | 3,4-methylenedioxyphenyl | OMe | O—CH₂—CH₂—C | N | N | N | O |
| I-380 | COOH | phenyl | —CH₂—CH₂— | 3,5-di-OMe-phenyl | Me | Me | CH | N | N | O |
| I-381 | COOH | 4-Cl-phenyl | —CH(4-OEt-phenyl)—CH₂— | 4-OEt-phenyl | OMe | Me | CH | N | N | O |
| I-382 | COOH | 4-Cl-phenyl | —CH(OH)—CH₂— | 4-OEt-phenyl | Me | Me | CH | N | N | O |
| I-383 | COOH | phenyl | —CH₂—CH₂— | 2-Cl-phenyl | OMe | Me | CH | N | N | O |
| I-384 | COOH | phenyl | —CH₂—CH₂—CH₂— | 2-Cl-phenyl | Me | Me | CH | N | N | O |
| I-385 | COOH | phenyl | —CH₂—CH₂— | 3,4-di-OMe-phenyl | OMe | O—CH₂—CH₂—C | N | N | N | O |
| I-386 | COOH | phenyl | —CH₂—CH₂— | 3,4,5-tri-OMe-phenyl | CF₃ | Me | CH | N | N | O |
| I-387 | COOH | 4-Me-phenyl | —CH₂—CH₂— | 4-OMe-phenyl | OMe | Me | CH | N | N | O |
| I-388 | COOH | 4-Me-phenyl | —CH₂—CH₂— | 4-OMe-phenyl | Me | Me | CH | N | N | O |
| I-389 | COOH | 4-Cl-phenyl | —CH₂—CH₂— | 4-OEt-phenyl | ethyl | Me | N | N | CH | O |
| I-390 | COOH | 3,4-di-Cl-phenyl | —CH₂—CH₂— | 3,5-di-OMe-phenyl | OMe | Me | CH | N | N | O |
| I-391 | COOH | 4-Cl-phenyl | —CH₂—CH₂— | 3,5-di-OMe-4-Cl-phenyl | Me | Me | CH | N | N | O |
| I-392 | COOH | 4-Cl-phenyl | —CH₂—CH₂— | 3,5-di-OMe-phenyl | Me | Me | N | N | CH | O |
| I-393 | COOH | 4-Cl-phenyl | —CH₂—CH₂— | 4-OEt-3-OMe-phenyl | ethyl | Me | CH | N | N | O |
| I-394 | COOH | phenyl | —CH₂—CH₂—CH₂— | 3,4-methylenedioxyphenyl | Me | Me | CH | N | N | O |
| I-395 | COOH | phenyl | —CH₂—CH₂—CH₂— | 3,4-methylenedioxyphenyl | Me | Me | N | N | N | O |
| I-396 | COOH | 4-Cl-phenyl | —CH₂—CH₂— | 4-OEt-3-OMe-phenyl | OMe | O—CH₂—CH₂—C | N | N | N | O |
| I-397 | COOH | 4-Cl-phenyl | —C(CH₃)₂—CH₂— | 3-OMe-phenyl | CF₃ | Me | CH | N | N | O |
| I-398 | COOH | phenyl | —CH₂—CH₂— | 4-Me-phenyl | ethyl | Me | CH | N | N | O |
| I-399 | COOH | 4-Me-phenyl | —CH₂—CH₂— | 4-Me-phenyl | ethyl | Me | CH | N | N | O |
| I-400 | COOH | phenyl | —CH₂—CH₂—CH₂— | 2-Cl-phenyl | CF₃ | Me | CH | N | N | O |
| I-401 | COOH | phenyl | —CH₂—CH₂— | 4-Me-phenyl | OMe | CH₂—CH₂—CH₂—C | N | N | N | O |
| I-402 | COOH | 4-Cl-phenyl | —C(CH₃)₂—CH₂— | 3-OMe-phenyl | Me | Me | CH | N | N | O |
| I-403 | COOH | 4-CF₃-phenyl | —CH₂—CH₂— | 4-Me-phenyl | ethyl | Me | CH | N | N | O |
| I-404 | COOH | 4-CF₃-phenyl | —CH₂—CH₂— | 4-Me-phenyl | OMe | O—CH₂—CH₂—C | N | N | N | O |
| I-405 | COOH | 4-Et-phenyl | —CH₂—CH₂— | 4-OMe-phenyl | OMe | Me | CH | N | N | S |
| I-406 | COOH | 4-Et-phenyl | —CH₂—CH₂— | 3-Me-4-OMe-phenyl | Me | Me | CH | N | N | O |
| I-407 | COOH | phenyl | —CH₂—CH₂— | 4-OEt-phenyl | OMe | O—CH₂—CH₂—C | N | N | N | O |
| I-408 | COOH | phenyl | —CH₂—CH₂— | 3,5-di-OMe-phenyl | CF₃ | Me | CH | N | N | O |
| I-409 | COOH | 4-Et-phenyl | —CH₂—CH₂— | 3-Me-4-OMe-phenyl | Me | Me | N | N | CH | O |
| I-410 | COOH | phenyl | —CH₂—CH₂—CH₂— | 3,4-methylenedioxyphenyl | CF₃ | Me | CH | N | N | O |
| I-411 | COOH | phenyl | —CH₂—CH₂—CH₂— | 3,4-methylenedioxyphenyl | OMe | Me | CH | N | N | O |
| I-412 | COOH | 4-Et-phenyl | —CH₂—CH₂— | 4-OMe-phenyl | ethyl | Me | CH | CH | N | O |
| I-413 | COOH | phenyl | —CH₂—CH₂— | 3,4-di-OMe-phenyl | ethyl | Me | CH | N | N | O |
| I-414 | COOH | phenyl | —CH₂—CH₂— | 3,4-di-OMe-phenyl | OMe | CH₂—CH₂—CH₂—C | N | N | N | O |
| I-415 | COOH | 4-Me-phenyl | —CH₂—CH₂—CH₂— | 4-Me-phenyl | Me | Me | CH | N | N | O |
| I-416 | COOH | 4-Me-phenyl | —CH₂—CH₂—CH₂— | 4-Me-phenyl | Me | Me | N | N | N | O |
| I-417 | COOH | 4-Et-phenyl | —CH₂—CH₂— | 3,4-di-OMe-phenyl | SMe | Me | CH | N | N | O |
| I-418 | COOMe | 4-Et-phenyl | —CH₂—CH₂— | 3,4-di-OMe-phenyl | Me | Me | CH | N | N | O |
| I-419 | COOH | 4-CF₃-phenyl | —CH₂—CH₂— | 4-Me-phenyl | Me | Me | CH | N | N | O |
| I-420 | COOH | 4-CF₃-phenyl | —CH₂—CH₂— | 4-Me-phenyl | Me | Me | N | N | N | O |
| I-421 | COOH | 4-Et-phenyl | —CH₂—CH₂— | 3,4-di-OMe-phenyl | Me | Me | N | N | N | S |
| I-422 | COOH | 4-Et-phenyl | —CH₂—CH₂— | 3,4-di-OMe-phenyl | ethyl | Me | CH | CH | N | O |
| I-423 | COOH | 4-Cl-phenyl | —CH₂—CH₂— | 4-OEt-3-OMe-phenyl | Me | Me | CH | N | N | O |
| I-424 | COOH | 4-Cl-phenyl | —CH₂—CH₂— | 4-OEt-3-OMe-phenyl | Me | Me | N | N | N | O |

TABLE I-continued

[sic]

$$R^6-Q-W-\underset{R^5}{\overset{R^4}{C}}-\underset{R^1}{\overset{}{CH}}-O-\underset{X}{\overset{Y}{\diagup}}\overset{R^2}{\underset{R^3}{\diagdown}}Z$$

I

| No. | R¹ | R⁴, R⁵ | Q | R⁶ | R² | R³ | Z | X | Y | W |
|---|---|---|---|---|---|---|---|---|---|---|
| I-425 | COOH | 4-Et-phenyl | —CH₂—CH₂— | 3,4-di-OMe-phenyl | OMe | O—CH=CH—C | N | N | O |
| I-426 | COOH | phenyl | —CH₂—CH₂—CH₂— | 4-SMe-phenyl | ethyl | Me | CH | N | N | O |
| I-427 | COOH | phenyl | —CH₂—CH₂—CH₂— | 4-SMe-phenyl | OMe | O—CH₂—CH₂—C | N | N | O |
| I-428 | COOH | phenyl | —CH₂—CH₂— | 4-Me-phenyl | Me | Me | CH | N | N | O |
| I-429 | COOH | phenyl | —CH₂—CH₂— | 4-Me-phenyl | Me | Me | N | N | N | O |
| I-430 | COOH | 4-Et-phenyl | —CH₂—CH₂— | 3-OMe-phenyl | OMe | CF₃ | CH | N | N | O |
| I-431 | COOH | 4-Me-phenyl | —CH₂—CH₂—CH₂— | 4-SMe-phenyl | OMe | Me | CH | N | N | O |
| I-432 | COOH | 4-Me-phenyl | —CH₂—CH₂—CH₂— | 4-SMe-phenyl | OMe | O—CH₂—CH₂—C | N | N | O |
| I-433 | COOH | 4-Et-phenyl | —CH(3-OMe-phenyl)—CH₂— | 3-OMe-phenyl | Me | Me | CH | N | N | O |
| I-434 | COOH | 4-Cl-phenyl | —CH₂—CH₂— | naphth-2-yl | Me | Me | CH | N | N | O |
| I-435 | COOH | 4-CF₃-phenyl | —CH₂—CH₂— | 4-SMe-phenyl | OMe | O—CH₂—CH₂—C | N | N | O |
| I-436 | COOH | 4-CF₃-phenyl | —CH₂—CH₂— | 4-Me-phenyl | OMe | Me | CH | N | N | O |
| I-437 | COOH | 4-Cl-phenyl | —CH₂—CH₂— | naphth-2-yl | Me | Me | N | N | N | O |
| I-438 | COOH | 4-Et-phenyl | —CH(OH)—CH₂— | 3-OMe-phenyl | Me | Me | N | N | N | O |
| I-439 | COOH | phenyl | —CH₂—CH₂— | 4-OEt-phenyl | ethyl | Me | CH | N | N | O |
| I-440 | COOH | phenyl | —CH₂—CH₂— | 4-OEt-phenyl | OMe | CH₂—CH₂—CH₂—C | N | N | O |
| I-441 | COOH | 4-Et-phenyl | —CH₂—CH₂— | 3-OMe-phenyl | Me | Me | CH | N | CH | O |
| I-442 | COOH | phenyl | —CH₂—CH₂—CH₂— | 4-SMe-phenyl | Me | Me | CH | N | N | O |
| I-443 | COOH | phenyl | —CH₂—CH₂—CH₂— | 4-SMe-phenyl | Me | Me | N | N | N | O |
| I-444 | COOH | 4-Et-phenyl | —C(CH₃)₂—CH₂— | 3-OMe-phenyl | OMe | O—CH₂—CH₂—C | N | N | O |
| I-445 | COOH | phenyl | —CH₂—CH₂— | 3,4-di-OMe-phenyl | Me | Me | CH | N | N | O |
| I-446 | COOH | phenyl | —CH₂—CH₂— | 3,4-di-OMe-phenyl | Me | Me | N | N | N | O |
| I-447 | COOH | 4-Me-phenyl | —CH₂—CH₂—CH₂— | 3,4-di-OMe-phenyl | ethyl | Me | CH | N | N | O |
| I-448 | COOH | 4-Me-phenyl | —CH₂—CH₂—CH₂— | 3-OMe-phenyl | OMe | O—CH₂—CH₂—C | N | N | O |
| I-449 | COOH | 4-Et-phenyl | —CH₂—CH₂— | 4-SMe-phenyl | OMe | Me | CH | N | N | S |
| I-450 | COOH | 4-Cl-phenyl | —CH₂—CH₂— | 2-OMe-phenyl | Me | Me | CH | N | N | O |
| I-451 | COOH | 4-CF₃-phenyl | —CH₂—CH₂— | 4-SMe-phenyl | Me | Me | N | N | N | O |
| I-452 | COOH | 4-CF₃-phenyl | —CH₂—CH₂— | 4-SMe-phenyl | ethyl | Me | CH | N | N | O |
| I-453 | COOH | 4-Cl-phenyl | —CH₂—CH₂— | 2-OMe-phenyl | Me | Me | N | N | N | O |
| I-454 | COOBzl | 4-Et-phenyl | —CH₂—CH₂— | 4-SMe-phenyl | Me | Me | CH | N | N | O |
| I-455 | COOH | 4-Et-phenyl | —CH₂—CH₂— | 4-SMe-phenyl | ethyl | Me | CH | CH | N | O |
| I-456 | COOH | 4-Et-phenyl | —CH₂—CH₂— | 4-Me-phenyl | OMe | Me | N | N | N | O |
| I-457 | COOH | 4-Cl-phenyl | —CH₂—CH₂— | 4-SMe-phenyl | OMe | O—CH₂—CH₂—C | N | N | O |
| I-458 | COOH | phenyl | —CH₂—CH₂—CH₂— | 4-SMe-phenyl | CF₃ | Me | CH | N | N | O |
| I-459 | COOH | phenyl | —CH₂—CH₂—CH₂— | 4-SMe-phenyl | OMe | Me | CH | N | N | O |
| I-460 | COOH | 4-Cl-phenyl | —CH₂—CH₂— | 4-OEt-3-OMe-phenyl | OMe | Me | CH | N | N | O |
| I-461 | COOH | 4-CF₃-phenyl | —CH₂—CH₂— | 4-OMe-phenyl | Me | Me | N | CH | N | O |
| I-462 | COOH | phenyl | —CH₂—CH₂— | 4-Me-phenyl | CF₃ | Me | CH | N | N | O |
| I-463 | COOH | 4-Me-phenyl | —CH₂—CH₂—CH₂— | 3,4-di-OMe-phenyl | OMe | Me | CH | N | N | O |
| I-464 | COOH | 4-Me-phenyl | —CH₂—CH₂—CH₂— | 3,4-di-OMe-phenyl | Me | Me | CH | N | N | O |
| I-465 | COOH | phenyl | —CH₂—CH₂— | 4-Me-phenyl | OMe | Me | CH | N | N | O |
| I-466 | COOH | 4-CF₃-phenyl | —C(CH₃)₂—CH₂— | 4-OMe-phenyl | ethyl | Me | CH | N | N | O |
| I-467 | COOH | 4-CF₃-phenyl | —CH₂—CH₂— | 4-SMe-phenyl | Me | Me | CH | N | N | O |
| I-468 | COOH | 4-CF₃-phenyl | —CH₂—CH₂— | 4-SMe-phenyl | Me | Me | CH | N | N | O |
| I-469 | COOH | 4-CF₃-phenyl | —CH₂—CH₂— | 3,4-di-OMe-phenyl | ethyl | Me | CH | CH | N | O |
| I-470 | COOH | 4-Cl-phenyl | —CH₂—CH₂— | 4-Cl-phenyl | OMe | O—CH₂—CH₂—C | N | N | O |
| I-471 | COOH | 4-Cl-phenyl | —CH₂—CH₂— | naphth-2-yl | OMe | Me | CH | N | N | O |
| I-472 | COOH | 4-CF₃-phenyl | —CH₂—CH₂— | 3,4-di-OMe-phenyl | OMe | O—CH₂—CH₂—C | N | N | S |
| I-473 | COOH | phenyl | —CH₂—CH₂— | 4-OEt-phenyl | Me | Me | CH | N | N | O |
| I-474 | COOH | phenyl | —CH₂—CH₂—CH₂— | 3,4-di-OMe-phenyl | ethyl | Me | CH | N | N | O |
| I-475 | COOH | phenyl | —CH₂—CH₂—CH₂— | 3,4-di-OMe-phenyl | OMe | O—CH₂—CH₂—C | N | N | O |
| I-476 | COOH | phenyl | —CH₂—CH₂— | 4-OEt-phenyl | Me | Me | N | N | N | O |
| I-477 | COOH | 4-CF₃-phenyl | —CH₂—CH₂— | 3-OMe-phenyl | ethyl | Me | N | N | N | O |
| I-478 | COOH | 4-CF₃-phenyl | —CH₂—CH₂— | 2-Me-3-OMe-phenyl | OMe | O—CH₂—CH₂—C | N | N | O |
| I-479 | COOH | 4-Me-phenyl | —CH₂—CH₂—CH₂— | 4-OMe-phenyl | ethyl | Me | CH | N | N | O |
| I-480 | COOH | 4-Me-phenyl | —CH₂—CH₂—CH₂— | 4-OMe-phenyl | OMe | O—CH₂—CH₂—C | N | N | O |
| I-481 | COOH | phenyl | —CH₂—CH₂— | 3,4-di-OMe-phenyl | OMe | OMe | CH | N | N | O |
| I-482 | COOH | phenyl | —CH₂—CH₂— | 3,4-di-OMe-phenyl | Me | Me | CH | N | N | O |
| I-483 | COOH | 4-CF₃-phenyl | —CH₂—CH₂— | 3-OMe-phenyl | ethyl | Me | CH | N | N | O |
| I-484 | COOH | 4-CF₃-phenyl | —CH₂—CH₂— | 3-OMe-phenyl | OMe | O—CH₂—CH₂—C | N | N | O |
| I-485 | COOH | 4-CF₃-phenyl | —CH₂—CH₂— | 3-Me-4-SMe-phenyl | OMe | Me | CH | N | N | O |
| I-486 | COOH | 4-Cl-phenyl | —CH₂—CH₂— | 3-OMe-phenyl | OMe | O—CH₂—CH₂—C | N | N | O |
| I-487 | COOH | 4-Cl-phenyl | —CH₂—CH₂— | 2-OMe-phenyl | OMe | Me | CH | N | N | O |
| I-488 | COOH | 4-CF₃-phenyl | —CH₂—CH₂— | cyclohexyl | OMe | Me | CH | N | N | O |
| I-489 | COOH | 4-CF₃-phenyl | —CH₂—CH₂— | 4-Me-phenyl | Me | Me | CH | N | N | S |
| I-490 | COOH | phenyl | —CH₂—CH₂—CH₂— | 3,4-di-OMe-phenyl | Me | Me | CH | N | N | O |

TABLE I-continued

I $$R^6-Q-W-\underset{R^5}{\overset{R^4}{C}}-\underset{R^1}{\overset{}{CH}}-O-\underset{X}{\overset{Y}{\underset{}{\bigcirc}}}\overset{R^2}{\underset{R^3}{Z}}$$

| No. | R$^1$ | R$^4$, R$^5$ | Q | R$^6$ | R$^2$ | R$^3$ | Z | X | Y | W |
|---|---|---|---|---|---|---|---|---|---|---|
| I-491 | COOH | phenyl | —CH$_2$—CH$_2$—CH$_2$— | 3,4-di-OMe-phenyl | Me | Me | N | N | N | O |
| I-492 | COOH | 4-Me-phenyl | —CH$_2$—CH$_2$— | cyclohexyl | OMe | Me | CH | N | N | O |
| I-493 | COOH | 4-Cl-phenyl | —CH$_2$—CH$_2$— | 4-SMe-phenyl | Me | Me | N | N | N | O |
| I-494 | COOH | 4-Cl-phenyl | —CH$_2$—CH$_2$— | 4-SMe-phenyl | ethyl | Me | CH | N | N | O |
| I-495 | COOH | 4-CF$_3$-phenyl | —CH$_2$—CH$_2$—CH$_2$— | 4-Me-phenyl | OMe | O—CH$_2$—CH$_2$—C | N | N | N | O |
| I-496 | COOH | 4-Me-phenyl | —CH$_2$—CH$_2$—CH$_2$— | 4-OMe-phenyl | OMe | Me | CH | N | N | O |
| I-497 | COOH | 4-Me-phenyl | —CH$_2$—CH$_2$— | 4-OMe-phenyl | Me | Me | CH | N | N | S |
| I-498 | COOH | phenyl | —CH$_2$—CH$_2$— | 3,4-methylenedioxyphenyl | OMe | CH$_2$—CH$_2$—CH$_2$—C | N | N | N | O |
| I-499 | COOH | phenyl | —CH$_2$—CH$_2$—CH$_2$— | phenyl | OMe | Me | CH | N | N | O |
| I-500 | COOH | phenyl | —CH$_2$—CH$_2$—CH$_2$— | phenyl | Me | Me | CH | N | N | O |
| I-501 | COOH | phenyl | —CH$_2$—CH$_2$— | 3,4-methylenedioxyphenyl | OMe | O—CH$_2$—CH$_2$—C | N | N | N | O |
| I-502 | COOH | 4-Me-phenyl | —CH$_2$—CH$_2$— | 3,4-di-OMe-phenyl | Me | Me | N | CH | N | O |
| I-503 | COOH | 4-Me-phenyl | —CH$_2$—CH$_2$— | 3,4-di-OMe-phenyl | ethyl | Me | CH | N | N | S |
| I-504 | COOH | 4-Cl-phenyl | —CH$_2$—CH$_2$— | 4-Cl-phenyl | Me | Me | N | N | N | O |
| I-505 | COOH | 4-Cl-phenyl | —CH$_2$—CH$_2$— | 4-Cl-phenyl | ethyl | Me | CH | N | N | O |
| I-506 | COOH | phenyl | —CH$_2$—CH$_2$—CH$_2$— | 3,4-di-OMe-phenyl | CF$_3$ | Me | CH | N | N | O |
| I-507 | COOH | phenyl | —CH$_2$—CH$_2$—CH$_2$— | 3,4-di-OMe-phenyl | OMe | Me | CH | N | N | O |
| I-508 | COOH | 4-Me-phenyl | —CH$_2$—CH$_2$— | cyclopentyl | OMe | Me | CH | N | N | O |
| I-509 | COOH | phenyl | —CH$_2$—CH$_2$— | 4-OEt-phenyl | CF$_3$ | Me | CH | N | N | O |
| I-510 | COOH | phenyl | —CH$_2$—CH$_2$— | 4-OEt-phenyl | OMe | Me | CH | N | N | O |
| I-511 | COOH | 4-CF$_3$-phenyl | —CH$_2$—CH$_2$—CH$_2$— | 4-Me-phenyl | Me | Me | N | N | N | O |
| I-512 | COOH | 4-CF$_3$-phenyl | —CH$_2$—CH$_2$—CH$_2$— | 4-Me-phenyl | ethyl | Me | CH | N | N | O |
| I-513 | COOH | 4-Me-phenyl | —CH$_2$—CH$_2$— | 4-SMe-phenyl | OMe | Me | CH | N | N | S |
| I-514 | COOH | 4-Me-phenyl | —CH$_2$—CH$_2$— | 4-SMe-phenyl | ethyl | Me | N | N | N | O |
| I-515 | COOH | 4-Me-phenyl | —CH$_2$—CH$_2$— | 4-Me-phenyl | OMe | O—CH$_2$—CH$_2$—C | N | N | N | O |
| I-516 | COOH | phenyl | —CH$_2$—CH$_2$—CH$_2$— | phenyl | CF$_3$ | Me | CH | N | N | O |
| I-517 | COOH | phenyl | —CH$_2$—CH$_2$— | 4-OMe-phenyl | OMe | O—CH$_2$—CH$_2$—C | N | N | N | O |
| I-518 | COOH | phenyl | —CH$_2$—CH$_2$— | 3,4-di-OMe-phenyl | CF$_3$ | Me | CH | N | N | O |
| I-519 | COOH | 4-Me-phenyl | —CH$_2$—CH$_2$— | 4-SMe-phenyl | ethyl | Me | CH | CH | N | O |
| I-520 | COOH | 4-Cl-phenyl | —CH$_2$—CH$_2$— | 3-OMe-phenyl | Me | Me | N | N | N | O |
| I-521 | COOH | 4-Cl-phenyl | —CH$_2$—CH$_2$— | 3-OMe-phenyl | ethyl | Me | CH | N | N | O |
| I-522 | COOH | phenyl | —CH$_2$—CH$_2$—CH$_2$— | 4-OMe-phenyl | OMe | CH$_2$—CH$_2$—CH$_2$—C | N | N | N | O |
| I-523 | COOH | phenyl | —CH$_2$—CH$_2$— | 4-OMe-phenyl | OMe | O—CH$_2$—CH$_2$—C | N | N | N | O |
| I-524 | COOMe | 4-Me-phenyl | —CH$_2$—CH$_2$— | 4-Me-phenyl | OMe | O—CH$_2$—CH$_2$—C | N | N | N | O |
| I-525 | COOMe | phenyl | —CH$_2$—CH$_2$—CH$_2$— | phenyl | CF$_3$ | Me | CH | N | N | O |
| I-526 | COOH | phenyl | —CH$_2$—CH$_2$—CH$_2$— | phenyl | OMe | Me | CH | N | N | S |
| I-527 | COOH | 4-CF$_3$-phenyl | —CH$_2$—CH$_2$—CH$_2$— | 4-SMe-phenyl | ethyl | Me | CH | N | N | O |
| I-528 | COOH | 4-CF$_3$-phenyl | —CH$_2$—CH$_2$—CH$_2$— | 4-SMe-phenyl | OMe | O—CH$_2$—CH$_2$—C | N | N | N | O |
| I-529 | COOH | 4-Cl-phenyl | —CH$_2$—CH$_2$— | 4-SMe-phenyl | OMe | Me | CH | N | N | O |
| I-530 | COOH | 4-Cl-phenyl | —CH$_2$—CH$_2$— | 4-SMe-phenyl | Me | Me | CH | N | N | O |
| I-531 | COOH | 4-Me-phenyl | —CH$_2$—CH$_2$— | 4-Me-phenyl | Me | Me | N | N | N | O |
| I-532 | COOH | 4-Me-phenyl | —CH$_2$—CH$_2$— | 4-Me-phenyl | ethyl | Me | CH | N | N | O |
| I-533 | COOH | phenyl | —CH$_2$—CH$_2$— | 4-F-phenyl | Me | Me | CH | N | N | O |
| I-534 | COOH | phenyl | —CH$_2$—CH$_2$— | 3,4-methylenedioxyphenyl | Me | Me | N | N | N | O |
| I-535 | COOH | phenyl | —CH$_2$—CH$_2$— | 3,4-methylenedioxyphenyl | ethyl | Me | CH | N | N | O |
| I-536 | COOH | phenyl | —CH$_2$—CH$_2$—CH$_2$— | phenyl | Me | Me | N | N | CH | O |
| I-537 | COOH | 4-Br-phenyl | —CH$_2$—CH$_2$—CH$_2$— | phenyl | ethyl | Me | CH | N | N | O |
| I-538 | COOH | phenyl | —CH$_2$—CH$_2$—CH$_2$— | 4-OMe-phenyl | Me | Me | N | N | N | O |
| I-539 | COOH | phenyl | —CH$_2$—CH$_2$—CH$_2$— | 4-OMe-phenyl | ethyl | Me | CH | N | N | O |
| I-540 | COOH | 4-Cl-phenyl | —CH$_2$—CH$_2$— | 4-Cl-phenyl | OMe | Me | CH | N | N | O |
| I-541 | COOH | 4-Cl-phenyl | —CH$_2$—CH$_2$— | 4-Cl-phenyl | Me | Me | CH | N | N | O |
| I-542 | COOH | 4-F-phenyl | —CH$_2$—CH$_2$—CH$_2$— | phenyl | OMe | O—CH$_2$—CH$_2$—C | N | N | N | O |
| I-543 | COOH | 4-CF$_3$-phenyl | —CH$_2$—CH$_2$—CH$_2$— | 3-OMe-phenyl | OMe | O—CH$_2$—CH$_2$—C | N | N | N | O |
| I-544 | COOH | 4-CF$_3$-phenyl | —CH$_2$—CH$_2$—CH$_2$— | 4-SMe-phenyl | OMe | Me | CH | N | N | O |
| I-545 | COOH | phenyl | —CH$_2$—CH$_2$— | naphth-2-yl | OMe | CH$_2$—CH$_2$—CH$_2$—C | N | N | N | O |
| I-546 | COOH | phenyl | —CH$_2$—CH$_2$— | naphth-2-yl | OMe | O—CH$_2$—CH$_2$—C | N | N | N | O |
| I-547 | COOH | 4-Me-phenyl | —CH$_2$—CH$_2$— | 4-Me-phenyl | OMe | Me | CH | N | N | O |
| I-548 | COOH | 4-Me-phenyl | —CH$_2$—CH$_2$— | 4-Me-phenyl | Me | Me | CH | N | N | O |
| I-549 | COOMe | phenyl | —CH(phenyl)—CH$_2$—CH$_2$— | phenyl | CF$_3$ | Me | CH | N | N | O |
| I-550 | COOH | 4-F-phenyl | —CH(phenyl)—CH$_2$—CH$_2$— | phenyl | OMe | Me | CH | N | N | O |
| I-551 | COOH | phenyl | —CH$_2$—CH$_2$— | 4-OMe-phenyl | ethyl | Me | CH | N | N | O |
| I-552 | COOH | phenyl | —CH$_2$—CH$_2$— | 4-OMe-phenyl | OMe | CH$_2$—CH$_2$—CH$_2$—C | N | N | N | O |
| I-553 | COOH | phenyl | —CH(phenyl)—CH$_2$—CH$_2$— | phenyl | Me | Me | CH | CH | N | O |
| I-554 | COOH | phenyl | —CH$_2$—CH$_2$—CH$_2$— | 4-OMe-phenyl | OMe | Me | CH | N | N | O |
| I-555 | COOH | phenyl | —CH$_2$—CH$_2$—CH$_2$— | 4-OMe-phenyl | Me | Me | CH | N | N | O |
| I-556 | COOH | 4-Cl-phenyl | —CH$_2$—CH$_2$— | 3-OMe-phenyl | OMe | Me | CH | N | N | O |

TABLE I-continued

[sic]

$$R^6-Q-W-\underset{\underset{R^5}{|}}{\overset{\overset{R^4}{|}}{C}}-\underset{\underset{R^1}{|}}{CH}-O-\text{(ring with Y, Z, X, R}^2\text{, R}^3\text{)}$$

| No. | R¹ | R⁴, R⁵ | Q | R⁶ | R² | R³ | Z | X | Y | W |
|---|---|---|---|---|---|---|---|---|---|---|
| I-557 | COOH | 4-Cl-phenyl | —CH₂—CH₂— | 3-OMe-phenyl | Me | Me | CH | N | N | O |
| I-558 | COOH | phenyl | —CH(phenyl)—CH₂—CH₂— | phenyl | OMe | Me | N | N | N | O |
| I-559 | COOH | 4-CF₃-phenyl | —CH₂—CH₂—CH₂— | 3,4-di-OMe-phenyl | OMe | O—CH₂—CH₂—C | N | N | N | O |
| I-560 | COOH | 4-CF₃-phenyl | —CH₂—CH₂—CH₂— | 3-OMe-phenyl | ethyl | Me | CH | N | N | O |
| I-561 | COOH | phenyl | —CH(phenyl)—CH₂—CH₂— | phenyl | ethyl | Me | N | N | N | O |
| I-562 | COOMe | phenyl | —CH₂—CH₂—CH₂— | 4-OMe-phenyl | CF₃ | Me | CH | N | N | O |
| I-563 | COOH | 4-Me-phenyl | —CH₂—CH₂— | 4-SMe-phenyl | ethyl | Me | CH | N | N | O |
| I-564 | COOH | 4-Me-phenyl | —CH₂—CH₂— | 4-SMe-phenyl | OMe | O—CH₂—CH₂—C | N | N | N | O |
| I-565 | COOH | 4-Cl-phenyl | —CH₂—CH₂— | 3,4,5-tri-OMe-phenyl | ethyl | Me | CH | N | N | O |
| I-566 | COOH | 4-Cl-phenyl | —CH₂—CH₂— | 3,4,5-tri-OMe-phenyl | OMe | O—CH₂—CH₂—C | N | N | N | O |
| I-567 | COOH | phenyl | —CH₂—CH₂—CH₂— | 4-OMe-phenyl | OMe | Me | CH | N | N | S |
| I-568 | COOH | phenyl | —CH₂—CH₂— | 3,4-methylenedioxyphenyl | OMe | Me | CH | N | N | O |
| I-569 | COOH | phenyl | —CH₂—CH₂— | 3,4-methylenedioxyphenyl | Me | Me | CH | N | N | O |
| I-570 | COOH | phenyl | —CH(phenyl)—CH₂—CH₂— | phenyl | OMe | O—CH₂—CH₂—C | N | N | N | O |
| I-571 | COOH | phenyl | —CH₂—CH₂—CH₂— | 4-OMe-phenyl | CF₃ | Me | CH | N | N | O |
| I-572 | COOH | phenyl | —CH₂—CH₂— | 4-OMe-phenyl | Me | Me | CH | N | CH | O |
| I-573 | COOH | phenyl | —CH₂—CH₂—CH₂— | 4-OMe-phenyl | ethyl | Me | N | N | N | O |
| I-574 | COOH | 4-Cl-phenyl | —CH₂—CH₂—CH₂— | 4-Et-phenyl | ethyl | Me | CH | N | N | O |
| I-575 | COOH | 4-CF₃-phenyl | —CH₂—CH₂—CH₂— | 3,4-di-OMe-phenyl | OMe | Me | CH | N | N | O |
| I-576 | COOH | 4-CF₃-phenyl | —CH₂—CH₂—CH₂— | 3,4-di-OMe-phenyl | ethyl | Me | CH | N | N | O |
| I-577 | COOH | 4-Cl-phenyl | —CH₂—CH₂— | 4-Et-phenyl | OMe | O—CH₂—CH₂—C | N | N | N | O |
| I-578 | COOH | phenyl | —CH₂—CH₂—CH₂— | 3-Cl-4-OMe-phenyl | ethyl | Me | CH | N | N | O |
| I-579 | COOH | 4-Me-phenyl | —CH₂—CH₂— | 4-SMe-phenyl | Me | Me | CH | N | N | O |
| I-580 | COOH | 4-Me-phenyl | —CH₂—CH₂— | 4-SMe-phenyl | Me | Me | N | N | N | O |
| I-581 | COOH | phenyl | —CH₂—CH₂— | naphth-2-yl | Me | Me | N | N | N | O |
| I-582 | COOH | phenyl | —CH₂—CH₂— | naphth-2-yl | ethyl | Me | CH | N | N | O |
| I-583 | COOH | 4-F-phenyl | —CH₂—CH₂—CH₂— | 4-OMe-phenyl | OMe | CH₂—CH₂—CH₂—C | N | N | N | O |
| I-584 | COOH | 4-F-phenyl | —CH₂—CH₂—CH₂— | 4-OMe-phenyl | OMe | O—CH₂—CH₂—C | N | N | N | O |
| I-585 | COOH | phenyl | —CH₂—CH₂— | 4-OMe-phenyl | Me | Me | CH | N | N | O |
| I-586 | COOH | phenyl | —CH(phenyl)—CH₂—CH₂— | phenyl | Me | Me | N | N | N | O |
| I-587 | COOH | phenyl | —CH(phenyl)—CH₂—CH₂— | phenyl | ethyl | Me | CH | N | N | O |
| I-588 | COOH | phenyl | —CH₂—CH₂— | 4-OMe-phenyl | Me | Me | N | N | N | O |
| I-589 | COOH | 4-F-phenyl | —CH₂—CH₂— | 3,4-di-OMe-phenyl | CF₃ | Me | CH | N | N | O |
| I-590 | COOH | 4-Cl-phenyl | —CH₂—CH₂— | 3,5-di-OMe-phenyl | ethyl | Me | CH | N | N | O |
| I-591 | COOH | 4-Et-phenyl | —CH₂—CH₂—CH₂— | 4-Me-phenyl | OMe | O—CH₂—CH₂—C | N | N | N | O |
| I-592 | COOH | 4-CF₃-phenyl | —CH₂—CH₂—CH₂— | 4-OMe-phenyl | OMe | O—CH₂—CH₂—C | N | N | N | O |
| I-593 | COOH | 4-Cl-phenyl | —CH₂—CH₂— | 3,5-di-OMe-phenyl | OMe | O—CH₂—CH₂—C | N | N | N | O |
| I-594 | COOH | phenyl | —CH(OH)—CH(OH)—CH₂— | 3,4-di-OMe-phenyl | OMe | Me | CH | N | N | O |
| I-595 | COOH | 4-Me-phenyl | —CH₂—CH₂— | 3-OMe-phenyl | OMe | O—CH₂—CH₂—C | N | N | N | O |
| I-596 | COOH | 4-Me-phenyl | —CH₂—CH₂— | 4-SMe-phenyl | OMe | Me | CH | N | N | O |
| I-597 | COOH | phenyl | —CH₂—CH₂—CH₂— | 3,4-di-OMe-phenyl | Me | Me | CH | N | N | S |
| I-598 | COOH | phenyl | —CH₂—CH₂—CH₂— | 3,4-di-OMe-phenyl | Me | Me | N | CH | N | O |
| I-599 | COOH | 4-Cl-phenyl | —CH₂—CH₂— | 3,4,5-tri-OMe-phenyl | Me | Me | CH | N | N | O |
| I-600 | COOH | 4-Cl-phenyl | —CH₂—CH₂— | 3,4,5-tri-OMe-phenyl | Me | Me | N | N | N | O |
| I-601 | COOEt | phenyl | —CH₂—CH₂—CH₂— | 3,4-di-OMe-phenyl | ethyl | Me | CH | N | N | O |
| I-602 | COOH | phenyl | —CH(phenyl)—CH₂— | phenyl | OMe | Me | CH | N | N | O |
| I-603 | COOH | phenyl | —CH(phenyl)—CH₂—CH₂— | phenyl | Me | Me | CH | N | N | O |
| I-604 | COOH | phenyl | —CH₂—CH₂— | 4-iPr-phenyl | OMe | O—CH₂—CH₂—C | N | N | N | O |
| I-605 | COOH | phenyl | —CH₂—CH₂— | 3,4-methylenedioxyphenyl | CF₃ | Me | CH | N | N | O |
| I-606 | COOH | phenyl | —CH₂—CH₂—CH₂— | 3,4-di-OMe-phenyl | OMe | O—CH₂—CH₂—C | N | N | N | S |
| I-607 | COOH | 4-Et-phenyl | —CH₂—CH₂—CH₂— | 4-SMe-phenyl | OMe | O—CH₂—CH₂—C | N | N | N | O |
| I-608 | COOH | 4-Et-phenyl | —CH₂—CH₂—CH₂— | 4-Me-phenyl | OMe | Me | CH | N | N | O |
| I-609 | COOH | 4-Br-phenyl | —CH₂—CH₂—CH₂— | 4-SMe-phenyl | OMe | Me | CH | N | N | O |
| I-610 | COOH | 4-Cl-phenyl | —CH₂—CH₂— | 4-Et-phenyl | Me | Me | CH | N | N | O |
| I-611 | COOH | 4-Me-phenyl | —CH₂—CH₂— | 3-OMe-phenyl | Me | Me | N | N | N | O |
| I-612 | COOH | 4-Me-phenyl | —CH₂—CH₂— | 3-OMe-phenyl | ethyl | Me | CH | N | N | O |
| I-613 | COOH | 4-Cl-phenyl | —CH₂—CH₂— | 4-Et-phenyl | Me | Me | N | N | N | O |
| I-614 | COOH | phenyl | —CH₂—CH₂—CH₂— | 4-SMe-phenyl | ethyl | Me | N | CH | N | O |
| I-615 | COOH | phenyl | —CH₂—CH₂— | naphth-2-yl | OMe | Me | CH | N | N | O |
| I-616 | COOH | phenyl | —CH₂—CH₂— | naphth-2-yl | Me | Me | CH | N | N | O |
| I-617 | COOH | phenyl | —CH(OH)—CH(OH)—CH₂— | 4-SMe-phenyl | OMe | O—CH₂—CH₂—C | N | N | N | O |
| I-618 | COOH | phenyl | —CH₂—CH₂—CH₂— | phenyl | OMe | O—CH₂—CH₂—C | N | N | N | O |
| I-619 | COOH | phenyl | —CH(phenyl)—CH₂—CH₂— | phenyl | CF₃ | Me | CH | N | N | O |
| I-620 | COOH | phenyl | —CH₂—CH₂—CH₂— | 4-Me-phenyl | Me | Me | N | N | CH | O |
| I-621 | COOH | phenyl | —CH₂—CH₂— | 4-OMe-phenyl | OMe | OMe | CH | N | N | O |
| I-622 | COOH | phenyl | —CH₂—CH₂— | 4-OMe-phenyl | OMe | Me | CH | N | N | O |

TABLE I-continued

[sic]

I

| No. | R¹ | R⁴, R⁵ | Q | R⁶ | R² | R³ | Z | X | Y | W |
|---|---|---|---|---|---|---|---|---|---|---|
| I-623 | COOH | 4-Et-phenyl | —CH₂—CH₂—CH₂— | 4-SMe-phenyl | Me | Me | CH | N | N | O |
| I-624 | COOH | 4-Et-phenyl | —CH₂—CH₂—CH₂— | 4-SMe-phenyl | ethyl | Me | CH | N | N | O |
| I-625 | COOH | phenyl | —CH₂—CH₂—CH₂— | 4-Me-phenyl | CF₃ | Me | CH | N | N | S |
| I-626 | COOH | 4-Cl-phenyl | —CH₂—CH₂—CH₂— | 3,5-di-OMe-phenyl | Me | Me | CH | N | N | O |
| I-627 | COOH | 4-Me-phenyl | —CH₂—CH₂— | 3-OMe-phenyl | OMe | Me | CH | N | N | O |
| I-628 | COOH | 4-Me-phenyl | —CH₂—CH₂— | 3-OMe-phenyl | Me | Me | CH | N | N | O |
| I-629 | COOH | 4-Cl-phenyl | —CH₂—CH₂— | 3,5-di-OMe-phenyl | Me | Me | N | N | N | O |
| I-630 | COOH | phenyl | —CH₂—CH₂—CH₂— | 4-Me-phenyl | OMe | Me | N | N | N | O |
| I-631 | COOH | phenyl | —CH(OH)—CH(OH)—CH₂— | 4-Me-phenyl | Me | Me | CH | N | N | O |
| I-632 | COOH | 4-Cl-phenyl | —CH₂—CH₂—CH₂— | 4-Et-phenyl | ethyl | Me | CH | N | N | O |
| I-633 | COOH | 4-Cl-phenyl | —CH₂—CH₂—CH₂— | 4-Et-phenyl | OMe | O—CH₂—CH₂—C | N | N | N | O |
| I-634 | COOH | 4-F-phenyl | —CH₂—CH₂—CH₂— | 4-Me-phenyl | Me | Me | N | N | N | O |
| I-635 | COOH | 4-Cl-phenyl | —CH₂—CH₂— | 3,4-di-OMe-phenyl | OMe | O—CH₂—CH₂—C | N | N | N | O |
| I-636 | COOH | phenyl | —CH₂—CH₂—CH₂— | phenyl | Me | Me | N | N | N | O |
| I-637 | COOH | phenyl | —CH₂—CH₂—CH₂— | phenyl | ethyl | Me | CH | N | N | O |
| I-638 | COOH | 4-Cl-phenyl | —CH₂—CH₂— | 3,4,5-tri-OMe-phenyl | OMe | Me | CH | N | N | O |
| I-639 | COOH | 4-F-phenyl | —CH₂—CH₂—CH₂— | 4-Me-phenyl | ethyl | Me | CH | N | N | O |
| I-640 | COOH | phenyl | —CH₂—CH₂— | 4-iPr-phenyl | ethyl | Me | CH | N | N | O |
| I-641 | COOH | 4-Et-phenyl | —CH₂—CH₂—CH₂— | 3-OMe-phenyl | ethyl | Me | CH | N | N | O |
| I-642 | COOH | 4-Et-phenyl | —CH₂—CH₂—CH₂— | 3-OMe-phenyl | OMe | Me | CH | N | N | O |
| I-643 | COOH | phenyl | —CH₂—CH₂— | 4-iPr-phenyl | OMe | CH₂—CH₂—CH₂—C | N | N | N | O |
| I-644 | COOH | 4-F-phenyl | —CH₂—CH₂—CH₂— | 4-Me-phenyl | OMe | O—CH₂—CH₂—C | N | N | N | O |
| I-645 | COOH | 4-Me-phenyl | —CH₂—CH₂— | 3,4-di-OMe-phenyl | ethyl | Me | CH | N | N | O |
| I-646 | COOH | 4-Me-phenyl | —CH₂—CH₂— | 3,4-di-OMe-phenyl | OMe | O—CH₂—CH₂—C | N | N | N | O |
| I-647 | COOH | 4-F-phenyl | —CH₂—CH₂— | 4-Et-phenyl | CF₃ | Me | CH | N | N | O |
| I-648 | COOH | 4-Cl-phenyl | —CH₂—CH₂— | 4-Me-phenyl | OMe | O—CH₂—CH₂—C | N | N | N | O |
| I-649 | COOH | 4-Cl-phenyl | —CH₂—CH₂— | 4-Et-phenyl | OMe | Me | CH | N | N | O |
| I-650 | COOMe | phenyl | —CH₂—CH₂—CH₂— | 4-Et-phenyl | OMe | Me | CH | N | N | O |
| I-651 | COOH | phenyl | —CH₂—CH₂— | 4-Cl-phenyl | OMe | O—CH₂—CH₂—C | N | N | N | O |
| I-652 | COOH | 4-Cl-phenyl | —CH₂—CH₂—CH₂— | 4-Me-phenyl | ethyl | Me | CH | N | N | O |
| I-653 | COOH | 4-Cl-phenyl | —CH₂—CH₂—CH₂— | 4-Et-phenyl | OMe | Me | CH | N | N | O |
| I-654 | COOH | phenyl | —CH₂—CH₂— | naphth-2-yl | CF₃ | Me | CH | N | N | O |
| I-655 | COOH | phenyl | —CH₂—CH₂—CH₂— | 3,4-di-Cl-phenyl | Me | Me | N | N | N | O |
| I-656 | COOH | 4-F-phenyl | —CH₂—CH₂—CH₂— | 4-Cl-phenyl | ethyl | Me | CH | N | N | O |
| I-657 | COOH | phenyl | —CH₂—CH₂— | phenyl | OMe | O—CH₂—CH₂—C | N | N | N | O |
| I-658 | COOH | phenyl | —CH₂—CH₂— | 4-OMe-phenyl | CF₃ | Me | CH | N | N | O |
| I-659 | COOH | 4-Et-phenyl | —CH₂—CH₂—CH₂— | 3,4-di-OMe-phenyl | OMe | O—CH₂—CH₂—C | N | N | N | O |
| I-660 | COOH | 4-Et-phenyl | —CH₂—CH₂—CH₂— | 3-OMe-phenyl | OMe | Me | CH | N | N | O |
| I-661 | COOH | phenyl | —CH₂—CH₂—CH₂— | 4-Cl-phenyl | OMe | CH₂—CH₂—CH₂—C | N | N | N | S |
| I-662 | COOH | 4-Cl-phenyl | —CH₂—CH₂— | 4-OEt-phenyl | OMe | O—CH₂—CH₂—C | N | N | N | O |
| I-663 | COOH | 4-Cl-phenyl | —CH₂—CH₂— | 3,5-di-OMe-phenyl | OMe | Me | CH | N | N | O |
| I-664 | COOH | phenyl | —CH₂—CH₂—CH₂— | 3-OMe-phenyl | ethyl | Me | N | CH | N | O |
| I-665 | COOH | phenyl | —CH₂—CH₂—CH₂— | 3-OMe-phenyl | OMe | Me | N | N | N | O |
| I-666 | COOH | 4-Cl-phenyl | —CH₂—CH₂—CH₂— | 4-Me-phenyl | OMe | Me | CH | N | N | O |
| I-667 | COOH | 4-Cl-phenyl | —CH₂—CH₂— | 4-Me-phenyl | Me | Me | N | N | N | O |
| I-668 | COOH | phenyl | —CH₂—CH₂—CH₂— | 2,3-di-OMe-phenyl | OMe | O—CH₂—CH₂—C | N | N | N | O |
| I-669 | COOH | 4-Cl-phenyl | —CH₂—CH₂— | 3,4-di-OMe-phenyl | Me | Me | N | N | N | O |
| I-670 | COOH | 4-Cl-phenyl | —CH₂—CH₂— | 3,4-di-OMe-phenyl | ethyl | Me | CH | N | N | O |
| I-671 | COOH | 3,4-di-Cl-phenyl | —CH₂—CH₂—CH₂— | 4-OMe-phenyl | OMe | Me | CH | N | N | O |
| I-672 | COOH | phenyl | —CH₂—CH₂— | 4-iPr-phenyl | Me | Me | CH | N | N | O |
| I-673 | COOH | 4-Et-phenyl | —CH₂—CH₂—CH₂— | 3,4-di-OMe-phenyl | Me | Me | CH | N | N | O |
| I-674 | COOH | 4-Et-phenyl | —CH₂—CH₂—CH₂— | 3,4-di-OMe-phenyl | ethyl | Me | CH | N | N | O |
| I-675 | COOH | phenyl | —CH₂—CH₂— | 4-iPr-phenyl | Me | Me | N | N | N | O |
| I-676 | COOH | 3,4-di-Cl-phenyl | —CH₂—CH₂—CH₂— | 4-OMe-phenyl | Me | Me | CH | N | N | O |
| I-677 | COOH | 3,4-di-Cl-phenyl | —CH₂—CH₂—CH₂— | 4-OMe-phenyl | ethyl | Me | CH | N | N | O |
| I-678 | COOH | 4-Cl-phenyl | —CH₂—CH₂— | 4-Me-phenyl | Me | Me | N | N | N | O |
| I-679 | COOH | 4-Cl-phenyl | —CH₂—CH₂— | 4-Me-phenyl | ethyl | Me | CH | N | N | O |
| I-680 | COOH | 4-Cl-phenyl | —CH₂—CH₂—CH₂— | 3,4-methylenedioxyphenyl | Me | Me | CH | N | N | O |
| I-681 | COOH | 4-Cl-phenyl | —CH₂—CH₂—CH₂— | 3,4-methylenedioxyphenyl | OMe | O—CH₂—CH₂—C | N | N | N | O |
| I-682 | COOH | 3,4-di-Cl-phenyl | —CH₂—CH₂—CH₂— | 4-OMe-phenyl | OMe | O—CH₂—CH₂—C | N | N | N | O |
| I-683 | COOH | phenyl | —CH₂—CH₂— | 4-Cl-phenyl | ethyl | Me | CH | N | N | O |
| I-684 | COOH | phenyl | —CH₂—CH₂— | 4-Cl-phenyl | OMe | CH₂—CH₂—CH₂—C | N | N | N | O |
| I-685 | COOH | phenyl | —CH(OH)—CH(OH)—CH₂— | 2-Cl-phenyl | OMe | Me | CH | N | N | O |
| I-686 | COOH | phenyl | —CH₂—CH₂—CH₂— | 2-Cl-phenyl | Me | Me | N | CH | N | O |
| I-687 | COOH | 4-Et-phenyl | —CH₂—CH₂—CH₂— | 4-OMe-phenyl | OMe | O—CH₂—CH₂—C | N | N | N | O |
| I-688 | COOH | 4-Et-phenyl | —CH₂—CH₂—CH₂— | 3,4-di-OMe-phenyl | OMe | Me | CH | N | N | O |

TABLE I-continued

[sic]

$$R^6-Q-W-\underset{R^5}{\overset{R^4}{C}}-\underset{R^1}{CH}-O-\text{(ring with Y, Z, X, R}^2\text{, R}^3\text{)}$$

I

| No. | R¹ | R⁴, R⁵ | Q | R⁶ | R² | R³ | Z | X | Y | W |
|---|---|---|---|---|---|---|---|---|---|---|
| I-689 | COOH | phenyl | —CH₂—CH₂— | phenyl | Me | Me | N | N | N | O |
| I-690 | COOH | phenyl | —CH₂—CH₂— | phenyl | ethyl | Me | CH | N | N | O |
| I-691 | COOH | phenyl | —CH₂—CH₂—CH₂— | 2-Cl-phenyl | Me | Me | N | N | N | S |
| I-692 | COOH | 4-Cl-phenyl | —CH₂—CH₂— | 4-OEt-phenyl | Me | Me | N | N | N | O |
| I-693 | COOH | 4-Cl-phenyl | —CH₂—CH₂— | 4-OEt-phenyl | ethyl | Me | CH | N | N | O |
| I-694 | COOH | 4-Cl-phenyl | —CH₂—CH₂—CH₂— | 4-iPr-phenyl | ethyl | Me | CH | N | N | O |
| I-695 | COOH | 4-Cl-phenyl | —CH₂—CH₂—CH₂— | 3,4-methylenedioxyphenyl | OMe | Me | CH | N | N | O |
| I-696 | COOH | phenyl | —CH₂—CH₂—CH₂— | 2-Cl-phenyl | ethyl | Me | CH | N | N | S |
| I-697 | COOMe | phenyl | —CH₂—CH₂—CH₂— | 2-Cl-phenyl | OMe | CH₂—CH₂—CH₂—C | N | N | N | O |
| I-698 | COOH | phenyl | —CH₂—CH₂—CH₂— | 3,5-di-OMe-4-Cl-phenyl | OMe | Me | CH | N | N | O |
| I-699 | COOH | 4-Cl-phenyl | —CH₂—CH₂— | 3,4-di-OMe-phenyl | OMe | Me | CH | N | N | O |
| I-700 | COOH | 4-Cl-phenyl | —CH₂—CH₂— | 3,4-di-OMe-phenyl | Me | Me | CH | N | N | O |
| I-701 | COOH | 4-Cl-phenyl | —CH₂—CH₂—CH₂— | 3-OMe-phenyl | OMe | O—CH₂—CH₂—C | N | N | N | O |
| I-702 | COOH | 4-Et-phenyl | —CH₂—CH₂—CH₂— | 4-OMe-phenyl | ethyl | Me | CH | N | N | O |
| I-703 | COOH | phenyl | —CH₂—CH₂—CH₂— | 3,5-di-OMe-4-Cl-phenyl | Me | Me | CH | N | N | O |
| I-704 | COOH | phenyl | —CH₂—CH₂— | 4-iPr-phenyl | CF₃ | Me | CH | N | N | O |
| I-705 | COOH | phenyl | —CH₂—CH₂— | 4-iPr-phenyl | OMe | Me | CH | N | N | O |
| I-706 | COOH | phenyl | —CH=CH—CH₂— | 4-OMe-phenyl | OMe | Me | CH | N | N | S |
| I-707 | COOMe | phenyl | —CH=CH—CH₂— | 4-OMe-phenyl | Me | Me | CH | N | N | O |
| I-708 | COOH | 4-Cl-phenyl | —CH₂—CH₂—CH₂— | 4-OEt, 3-OMe-phenyl | OMe | O—CH₂—CH₂—C | N | N | N | O |
| I-709 | COOH | 4-Cl-phenyl | —CH₂—CH₂—CH₂— | 4-iPr-phenyl | Me | Me | N | N | N | O |
| I-710 | COOH | 4-Cl-phenyl | —CH₂—CH₂— | 4-Me-phenyl | OMe | Me | CH | N | N | O |
| I-711 | COOH | 4-Cl-phenyl | —CH₂—CH₂— | 4-Me-phenyl | Me | Me | CH | N | N | O |
| I-712 | COOH | phenyl | —CH=CH—CH₂— | 4-OMe-phenyl | Me | Me | N | CH | N | O |
| I-713 | COOH | phenyl | —CH₂—CH₂— | 4-Cl-phenyl | Me | Me | CH | N | N | O |
| I-714 | COOH | phenyl | —CH₂—CH₂— | 4-Cl-phenyl | Me | Me | N | N | N | O |
| I-715 | COOH | 4-Cl-phenyl | —CH₂—CH₂—CH₂— | 3-OMe-phenyl | Me | Me | N | N | N | O |
| I-716 | COOH | 4-Cl-phenyl | —CH₂—CH₂—CH₂— | 3-OMe-phenyl | ethyl | Me | CH | N | N | O |
| I-717 | COOH | phenyl | —CH=CH—CH₂— | 3-Cl-4-OMe-phenyl | ethyl | Me | CH | N | N | O |
| I-718 | COOH | phenyl | —CH=CH—CH₂— | 3-Cl-4-OMe-phenyl | OMe | O—CH₂—CH₂—C | N | N | N | O |
| I-719 | COOH | phenyl | —CH₂—CH₂— | phenyl | OMe | Me | CH | N | N | O |
| I-720 | COOH | phenyl | —CH₂—CH₂— | phenyl | Me | Me | CH | N | N | O |
| I-721 | COOH | 4-F-phenyl | —CH=CH—CH₂— | 3,4-di-OMe-phenyl | OMe | Me | CH | N | N | O |
| I-722 | COOH | 4-Cl-phenyl | —CH₂—CH₂—CH₂— | 4-SMe-phenyl | OMe | O—CH₂—CH₂—C | N | N | N | O |
| I-723 | COOH | 4-Cl-phenyl | —CH₂—CH₂—CH₂— | 4-OEt, 3-OMe-phenyl | OMe | Me | CH | N | N | O |
| I-724 | COOH | 4-Cl-phenyl | —CH₂—CH₂— | 4-OEt-phenyl | OMe | Me | CH | N | N | O |
| I-725 | COOH | 4-Cl-phenyl | —CH₂—CH₂— | 4-OEt-phenyl | Me | Me | CH | N | N | O |
| I-726 | COOMe | phenyl | —CH=CH—CH₂— | 3,4-di-OMe-phenyl | Me | Me | CH | N | N | O |
| I-727 | COOH | phenyl | —CH=CH—CH₂— | 3,4-di-OMe-phenyl | Me | Me | N | CH | N | O |
| I-728 | COOH | phenyl | —CH=CH—CH₂— | 3,4-di-OMe-phenyl | OMe | O—CH₂—CH₂—C | N | N | N | S |
| I-729 | COOH | 4-Cl-phenyl | —CH₂—CH₂—CH₂— | 3-OMe-phenyl | OMe | Me | CH | N | N | O |
| I-730 | COOH | 4-Cl-phenyl | —CH₂—CH₂—CH₂— | 3-OMe-phenyl | Me | Me | CH | N | N | O |
| I-731 | COOH | 4-Cl-phenyl | —CH₂—CH₂— | 4-OMe-phenyl | ethyl | Me | CH | N | N | O |
| I-732 | COOH | 4-Cl-phenyl | —CH₂—CH₂— | 4-OMe-phenyl | OMe | O—CH₂—CH₂—C | N | N | N | O |
| I-733 | COOH | phenyl | —CH=CH—CH₂— | cyclohexyl | OMe | Me | CH | N | N | O |
| I-734 | COOH | phenyl | —CH₂—CH₂— | 4-OEt-3-OMe-phenyl | OMe | CH₂—CH₂—CH₂—C | N | N | N | O |
| I-735 | COOH | phenyl | —CH₂—CH₂— | 4-OEt-3-OMe-phenyl | OMe | O—CH₂—CH₂—C | N | N | N | O |
| I-736 | COOH | 4-Cl-phenyl | —CH₂—CH₂—CH₂— | 4-SMe-phenyl | Me | Me | N | N | N | O |
| I-737 | COOH | 4-Cl-phenyl | —CH₂—CH₂—CH₂— | 4-SMe-phenyl | ethyl | Me | CH | N | N | O |
| I-738 | COOH | phenyl | —CH=CH—CH₂— | cyclohexyl | Me | Me | CH | N | N | O |
| I-739 | COOH | phenyl | —CH=CH—CH₂— | 4-Me-phenyl | Me | Me | N | N | N | S |
| I-740 | COOH | 4-Cl-phenyl | —CH₂—CH₂— | 3,4-methylenedioxyphenyl | ethyl | Me | CH | N | N | O |
| I-741 | COOH | 4-Cl-phenyl | —CH₂—CH₂— | 3,4-methylenedioxyphenyl | OMe | O—CH₂—CH₂—C | N | N | N | O |
| I-742 | COOH | phenyl | —C(phenyl)=CH—CH₂— | phenyl | OMe | Me | CH | N | N | O |
| I-743 | COOH | 4-Cl-phenyl | —CH₂—CH₂—CH₂— | 3,5-di-OMe-phenyl | OMe | Me | CH | N | N | O |
| I-744 | COOH | 4-Cl-phenyl | —CH₂—CH₂—CH₂— | 3,5-di-OMe-phenyl | Me | Me | CH | N | N | O |
| I-745 | COOH | phenyl | —CH₂—CH₂— | 4-Cl-phenyl | CF₃ | Me | CH | N | N | O |
| I-746 | COOH | phenyl | —CH₂—CH₂— | 4-Cl-phenyl | OMe | Me | CH | N | N | O |
| I-747 | COOH | 4-F-phenyl | —CH=CH—CH₂— | phenyl | Me | Me | CH | N | N | O |
| I-748 | COOH | 4-F-phenyl | —CH=CH—CH₂— | phenyl | Me | Me | N | N | N | O |
| I-749 | COOH | phenyl | —CH₂—CH₂— | 4-OEt-3-OMe-phenyl | Me | Me | N | N | N | O |
| I-750 | COOH | 4-Cl-phenyl | —CH₂—CH₂—CH₂— | 4-SMe-phenyl | OMe | Me | CH | N | N | O |
| I-751 | COOH | 4-Cl-phenyl | —CH₂—CH₂—CH₂— | 4-SMe-phenyl | Me | Me | CH | N | N | O |
| I-752 | COOH | phenyl | —CH₂—CH₂— | 4-OEt-3-OMe-phenyl | ethyl | Me | CH | N | N | O |
| I-753 | COOH | phenyl | —C(phenyl)=CH—CH₂— | phenyl | ethyl | Me | CH | N | N | O |
| I-754 | COOH | 4-Cl-phenyl | —CH₂—CH₂— | naphth-2-yl | ethyl | Me | CH | N | N | O |

TABLE I-continued

[sic]

I

R⁶—Q—W—C(R⁴)(R⁵)—CH(R¹)—O—[pyrimidine ring with R², R³, X, Y, Z]

| No. | R¹ | R⁴, R⁵ | Q | R⁶ | R² | R³ | Z | X | Y | W |
|---|---|---|---|---|---|---|---|---|---|---|
| I-755 | COOH | 4-Cl-phenyl | —CH$_2$—CH$_2$— | naphth-2-yl | OMe | O—CH$_2$—CH$_2$—C | N | N | O |
| I-756 | COOH | phenyl | —CH=CH—CH$_2$— | phenyl | OMe | O—CH$_2$—CH$_2$—C | N | N | S |
| I-757 | COOH | 4-Cl-phenyl | —CH$_2$—CH$_2$—CH$_2$— | 4-OEt-phenyl | Me | Me | CH | N | N | O |
| I-758 | COOH | 4-Cl-phenyl | —CH$_2$—CH$_2$—CH$_2$— | 4-OEt-phenyl | ethyl | Me | CH | N | N | O |
| I-759 | COOH | phenyl | —CH$_2$—CH$_2$—CH$_2$— | 4-OEt-phenyl | CF$_3$ | Me | CH | N | N | O |
| I-760 | COOH | phenyl | —CH$_2$—CH$_2$—CH$_2$— | 4-OEt-phenyl | OMe | Me | CH | N | N | O |
| I-761 | COOH | 4-Cl-phenyl | —CH$_2$—CH$_2$— | 4-OMe-phenyl | Me | Me | CH | N | N | O |
| I-762 | COOH | 4-Cl-phenyl | —CH$_2$—CH$_2$— | 4-OMe-phenyl | Me | Me | N | N | N | O |
| I-763 | COOH | 4-Cl-phenyl | —CH$_2$—CH$_2$—CH$_2$— | 3,4-di-OMe-phenyl | ethyl | Me | CH | N | N | O |
| I-764 | COOH | 4-Cl-phenyl | —CH$_2$—CH$_2$—CH$_2$— | 3,4-di-OMe-phenyl | OMe | O—CH$_2$—CH$_2$—C | N | N | O |
| I-765 | COOH | phenyl | —CH$_2$—CH$_2$—CH$_2$— | 4-OEt-phenyl | Me | Me | CH | N | N | O |

Example 16

Receptor binding data were measured by the binding assay described above for the compounds listed hereinafter.

The results are shown in Table 2.

TABLE 2

| | Receptor binding data ($K_i$ values) | |
|---|---|---|
| Compound | ET$_A$ [nM/l] [sic] | ET$_B$ [nM/l] [sic] |
| I-116 | 35 | 35 |
| I-140 | 575 | 460 |
| I-146 | 4 | 29 |
| I-321 | 340 | 290 |
| I-355 | 132 | 82 |
| I-370 | 11 | 54 |
| I-445 | 3.5 | 7.2 |
| I-445 (S) enantiomer | 1.3 | 4.1 |
| I-445 (R) enantiomer | 65 | 140 |
| I-482 | 2 | 14 |
| I-499 | 31 | 135 |
| I-585 | 6 | 23 |
| I-593 | 300 | 160 |
| I-622 | 3 | 23 |
| I-635 | 210 | 126 |
| I-672 | 60 | 185 |
| I-699 | 230 | 130 |
| I-713 | 20 | 96 |

We claim:

1. A carboxylic acid compound of the formula I

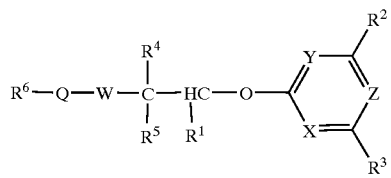

I where R¹ is a group $$-\overset{O}{\underset{\|}{C}}-R$$

where R is
- a radical OR⁷ where R⁷ is hydrogen, the cation of an alkali metal, the cation of an alkaline earth metal or a physiologically tolerated organic ammonium ion;
- R² is hydrogen, hydroxyl, NH$_2$, NH(C$_1$–C$_4$-alkyl), N(C$_1$–C$_4$-alkyl)$_2$, halogen, C$_1$–C$_4$-alkyl, C$_2$–C$_4$-alkenyl, C$_2$–C$_4$-alkynyl, C$_1$–C$_4$-haloalkyl, C$_1$–C$_4$-alkoxy, C$_1$–C$_4$-haloalkoxy or C$_1$–C$_4$-alkylthio;
- X is nitrogen;
- Y is nitrogen;
- Z is CR¹⁰, where R¹⁰ is hydrogen or C$_1$–C$_4$-alkyl;
- R³ is hydrogen, hydroxyl, NH$_2$, NH(C$_1$–C$_4$-alkyl), N(C$_1$–C$_4$-alkyl)$_2$, halogen, C$_1$–C$_4$-alkyl, C$_2$–C$_4$-alkenyl, C$_2$–C$_4$-alkynyl, C$_1$–C$_4$-hydroxyalkyl, C$_1$–C$_4$-haloalkyl, C$_1$–C$_4$-alkoxy, C$_1$–C$_4$-haloalkoxy or C$_1$–C$_4$-alkylthio, or CR³ is linked to CR¹⁰ as indicated above to give a 5- or 6-membered ring;
- R⁴ and R⁵, which may be identical or different, are phenyl or naphthyl, unsubstituted or substituted;
- R⁶ is substituted phenyl;
- W is oxygen;
- Q is a spacer whose length corresponds to that of a C$_2$–C$_4$ chain, or the physiologically tolerated salts, and the enantiomerically pure and diastereoisomerically pure forms thereof wherein the compound has an ET$_A$:ET$_B$ affinity ratio of greater than 0.1 and less than 20.

2. A pharmaceutical preparation for peroral, parenteral or intraparenteral use, comprising at least one carboxylic acid compound as claimed in claim 1, and conventional pharmaceutical ancillary substances.

3. The method of treating a disease selected from the group consisting of chronic heart failure, restenosis, high blood pressure, pulmonary hypertension, acute/chronic kidney failure, cerebral ischemia, asthma, benign prostate hyperplasia and prostate cancer comprising administering an effective amount of a compound of claim 1 to a patient in need of such treatment.

4. The method of claim 3 further comprising administering inhibitors of the rennin-angiotensin system mixed ACE/ neutral endopeptidase (NEP) inhibitors and/or β blockers.

5. The carboxylic acid derivative of claim 1, wherein Q is $C_2$–$C_4$-alkyl, $C_3$–$C_4$-alkenyl, $C_3$–$C_4$-alkynyl, —S—$CH_2$—$CH_2$—, or —O—$CH_2$—$CH_2$—, each of these radicals being unsubstituted or substituted one or more times by halogen, hydroxyl, mercapto, carboxyl, $C_1$–$C_4$-alkyl, $C_1$–$C_4$-alkoxy, $C_1$–$C_4$-alkylthio, or phenyl which is unsubstituted or substituted one or more times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

or Q forms together with $R^6$ 2-indanyl, 3-indanyl, 1,2,3,4-tetrahydro-2-naphthyl, or 1,2,3,4-tetrahydro-3-naphthyl, it being possible for the phenyl rings in each case to be substituted by halogen, hydroxyl, mercapto, carboxyl, cyano, $C_1$–$C_4$-alkoxy, $C_1$–$C_4$-alkyl, $C_2$–$C_4$-alkynyl, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkoxycarbonyl, NH($C_1$–$C_4$-alkyl), N($C_1$–$C_4$-alkyl)$_2$ or phenyl.

\* \* \* \* \*

UNITED STATES PATENT AND TRADEMARK OFFICE
CERTIFICATE OF CORRECTION

PATENT NO. : 6,670,367 B1
DATED : December 30, 2003
INVENTOR(S) : Wilhelm Amberg et al.

It is certified that error appears in the above-identified patent and that said Letters Patent is hereby corrected as shown below:

<u>Title page,</u>
Item [22], change "Mar. 2, 1997" to -- Sept. 2, 1997 --.

Signed and Sealed this

Sixth Day of April, 2004

JON W. DUDAS
*Acting Director of the United States Patent and Trademark Office*